US012084430B2

(12) United States Patent
Taylor et al.

(10) Patent No.: US 12,084,430 B2
(45) Date of Patent: Sep. 10, 2024

(54) TRICYCLIC UREA COMPOUNDS AS JAK2 V617F INHIBITORS

(71) Applicant: Incyte Corporation, Wilmington, DE (US)

(72) Inventors: Cooper Taylor, Kennett Square, PA (US); Yanran Ai, West Chester, PA (US); Chunhong He, Boothwyn, PA (US); Ke Zhang, Garnet Valley, PA (US); Eddy W. Yue, Landenberg, PA (US)

(73) Assignee: Incyte Corporation, Wilmington, DE (US)

( * ) Notice: Subject to any disclaimer, the term of this patent is extended or adjusted under 35 U.S.C. 154(b) by 0 days.

(21) Appl. No.: 18/122,323

(22) Filed: Mar. 16, 2023

(65) Prior Publication Data

US 2023/0295124 A1 Sep. 21, 2023

Related U.S. Application Data

(60) Provisional application No. 63/396,826, filed on Aug. 10, 2022, provisional application No. 63/320,909, filed on Mar. 17, 2022.

(51) Int. Cl.
*C07D 401/14* (2006.01)
*A61P 35/00* (2006.01)
*A61P 35/02* (2006.01)
*C07D 471/14* (2006.01)

(52) U.S. Cl.
CPC .................. *C07D 401/14* (2013.01)

(58) Field of Classification Search
CPC ..... C07D 401/14; C07D 471/14; A61P 35/00; A61P 35/02
See application file for complete search history.

(56) References Cited

U.S. PATENT DOCUMENTS

| 4,698,341 | A | 10/1987 | Satzinger et al. |
| 6,339,099 | B1 | 1/2002 | Lam et al. |
| 6,951,865 | B2 | 10/2005 | Hibi et al. |
| 7,429,456 | B2 | 9/2008 | Vainchenker et al. |
| 7,781,199 | B2 | 8/2010 | Vainchenker et al. |
| 7,879,844 | B2 | 2/2011 | Inoue et al. |
| 8,163,767 | B2 | 4/2012 | Inoue et al. |
| 8,524,867 | B2 | 9/2013 | Bernett et al. |
| 8,637,235 | B2 | 1/2014 | Vainchenker et al. |
| 8,785,639 | B2 | 7/2014 | Wishart et al. |
| 8,852,931 | B2 | 10/2014 | Vainchenker et al. |
| 9,115,133 | B2 | 8/2015 | Barawkar et al. |
| 9,233,985 | B2 | 1/2016 | Van Zandt et al. |
| 9,321,730 | B2 | 4/2016 | Chan et al. |
| 9,493,419 | B2 | 11/2016 | Tang et al. |
| 10,065,974 | B2 | 9/2018 | Sjogren et al. |
| 10,155,987 | B2 | 12/2018 | Sattler et al. |
| 10,287,303 | B2 | 4/2019 | Sjogren et al. |
| 10,377,759 | B2 | 8/2019 | Yamamoto et al. |
| 11,661,422 | B2 | 5/2023 | Liu et al. |
| 11,691,971 | B2 | 7/2023 | Shepard et al. |
| 11,753,413 | B2 | 9/2023 | Yu et al. |
| 11,767,323 | B2 | 9/2023 | Liu et al. |
| 11,780,840 | B2 * | 10/2023 | Ai .................. A61P 37/00 514/210.16 |
| 11,919,908 | B2 | 3/2024 | Buesking et al. |
| 2003/0139431 | A1 | 7/2003 | Kawakami et al. |
| 2004/0209902 | A1 | 10/2004 | Lin et al. |
| 2005/0182060 | A1 | 8/2005 | Kelly et al. |
| 2006/0004043 | A1 | 1/2006 | Bhagwat et al. |
| 2007/0049610 | A1 | 3/2007 | Dillon et al. |
| 2007/0161670 | A1 | 7/2007 | Staab et al. |
| 2008/0004297 | A1 | 1/2008 | Cai et al. |
| 2008/0004318 | A1 | 1/2008 | Chelliah et al. |
| 2008/0188467 | A1 | 8/2008 | Wong et al. |
| 2008/0280879 | A1 | 11/2008 | Brickner et al. |
| 2008/0293739 | A1 | 11/2008 | Trede |
| 2009/0246198 | A1 | 10/2009 | Dong et al. |
| 2010/0105661 | A1 | 4/2010 | Shirakami et al. |
| 2010/0160355 | A1 | 6/2010 | DeGoey et al. |
| 2011/0182812 | A1 | 7/2011 | Szardenings et al. |
| 2011/0269740 | A1 | 11/2011 | Sunny et al. |
| 2011/0313003 | A1 | 12/2011 | Shi et al. |
| 2012/0065188 | A1 | 3/2012 | Brickner et al. |
| 2012/0165370 | A1 | 7/2012 | Tang et al. |
| 2012/0214842 | A1 | 8/2012 | Donello et al. |
| 2012/0282233 | A1 | 11/2012 | Rolshausen et al. |
| 2013/0267521 | A1 | 10/2013 | Castro et al. |
| 2013/0281399 | A1 | 10/2013 | McLure et al. |

(Continued)

FOREIGN PATENT DOCUMENTS

| CN | 102838600 | 12/2012 |
| CN | 102838601 | 12/2012 |

(Continued)

OTHER PUBLICATIONS

Alcock et al., "Development of Potent and Selective Janus Kinase 2/3 Directing PG-PROTACs," ACS Med. Chem. Lett., 2022, 13(3): 475-482.
Atzrodt et al., "The Renaissance of H/D Exchange," Angew. Chem. Int. Ed., 2007, 7744-7765.
Baxter et al., "Acquired mutation of the tyrosine kinase JAK2 in human myeloproliferative disorders," Lancet, 2005, 365:1054-1061.
Bennett et al., "Proposals for the classification of the myelodysplastic syndromes," Br. J. Haematol., 1982, 51:189-199.
Berge et al., "Pharmaceutical Salts," J. of Pharm. Sci., 1977, 66(1):1-19.

(Continued)

*Primary Examiner* — Deepak R Rao
*Assistant Examiner* — Kevin S Martin
(74) *Attorney, Agent, or Firm* — Fish & Richardson P.C.

(57) ABSTRACT

The present application provides tricyclic urea compounds that modulate the activity of the V617F variant of JAK2, which are useful in the treatment of various diseases, including cancer.

12 Claims, No Drawings

(56) References Cited

U.S. PATENT DOCUMENTS

| | | |
|---|---|---|
| 2013/0302248 A1 | 11/2013 | Gangadharmath et al. |
| 2014/0142102 A1 | 4/2014 | Fairfax et al. |
| 2014/0225082 A1 | 8/2014 | Park et al. |
| 2014/0249204 A1 | 9/2014 | Vainchenker et al. |
| 2014/0286964 A1 | 9/2014 | Hubbard et al. |
| 2014/0288048 A1 | 9/2014 | Castro et al. |
| 2016/0016914 A1 | 1/2016 | Ladziata et al. |
| 2016/0118600 A1 | 4/2016 | Kim et al. |
| 2016/0220592 A1 | 8/2016 | Franz et al. |
| 2017/0107216 A1 | 4/2017 | Wu et al. |
| 2017/0121346 A1 | 5/2017 | Sprengler et al. |
| 2017/0145025 A1 | 5/2017 | Li et al. |
| 2017/0174671 A1 | 6/2017 | Wu et al. |
| 2017/0174679 A1 | 6/2017 | Lajkiewicz et al. |
| 2017/0226095 A1 | 8/2017 | Tazi et al. |
| 2017/0298040 A1 | 10/2017 | Bennett et al. |
| 2017/0320875 A1 | 11/2017 | Li et al. |
| 2017/0342060 A1 | 11/2017 | Lu et al. |
| 2017/0362253 A1 | 12/2017 | Xiao et al. |
| 2018/0016260 A1 | 1/2018 | Yu et al. |
| 2018/0031557 A1 | 2/2018 | Scherrer et al. |
| 2018/0086719 A1 | 3/2018 | Chandrasekhar et al. |
| 2018/0104245 A1 | 4/2018 | Hansen |
| 2018/0179159 A1 | 6/2018 | Becknell et al. |
| 2018/0237797 A1 | 8/2018 | Loh |
| 2019/0152913 A1 | 5/2019 | Becknell et al. |
| 2019/0152988 A1 | 5/2019 | Sprengler et al. |
| 2019/0256492 A1 | 8/2019 | Tu et al. |
| 2021/0395251 A1 | 12/2021 | Shepard et al. |
| 2021/0395257 A1 | 12/2021 | Yu et al. |
| 2022/0002299 A1 | 1/2022 | Liu et al. |
| 2022/0064165 A1 | 3/2022 | Liu et al. |
| 2022/0169649 A1 | 6/2022 | Ai et al. |
| 2022/0213108 A1 | 7/2022 | Buesking et al. |
| 2022/0281887 A1 | 9/2022 | Shepard et al. |
| 2023/0093099 A1 | 3/2023 | Plewe et al. |

FOREIGN PATENT DOCUMENTS

| | | |
|---|---|---|
| CN | 104311426 | 1/2015 |
| CN | 104725249 | 6/2015 |
| CN | 105461714 | 4/2016 |
| CN | 105481765 | 4/2016 |
| CN | 105732591 | 7/2016 |
| CN | 109575022 | 4/2019 |
| CN | 109608504 | 4/2019 |
| CN | 111484480 | 8/2020 |
| EP | 0329012 | 8/1989 |
| EP | 0481448 | 4/1992 |
| EP | 0652218 | 5/1995 |
| EP | 1692281 | 10/2005 |
| EP | 2309567 | 10/2010 |
| EP | 3277293 | 2/2018 |
| EP | 3277820 | 2/2018 |
| EP | 3578555 | 12/2019 |
| FR | 2996129 | 4/2014 |
| JP | 62209062 | 9/1987 |
| JP | 07089957 | 4/1995 |
| JP | 2000123973 | 4/2000 |
| JP | 2003107641 | 4/2003 |
| JP | 2004196702 | 7/2004 |
| KR | 20140111166 | 9/2014 |
| KR | 20150002266 | 1/2015 |
| KR | 20160123112 | 10/2016 |
| KR | 20170003469 | 6/2017 |
| WO | WO 1993/17681 | 9/1993 |
| WO | WO 1993/17682 | 9/1993 |
| WO | WO 1995/18127 | 7/1995 |
| WO | WO 1997/34893 | 9/1997 |
| WO | WO 1997/47601 | 12/1997 |
| WO | WO 1998/16184 | 4/1998 |
| WO | WO 1998/40373 | 9/1998 |
| WO | WO 1999/61444 | 12/1999 |
| WO | WO 1999/64400 | 12/1999 |
| WO | WO 2000/041695 | 7/2000 |
| WO | WO 2000/067754 | 11/2000 |
| WO | WO 2000/068230 | 11/2000 |
| WO | WO 2001/023389 | 4/2001 |
| WO | WO 2001/042247 | 6/2001 |
| WO | WO 2001/047891 | 7/2001 |
| WO | WO 2001/058899 | 8/2001 |
| WO | WO 2001/070229 | 9/2001 |
| WO | WO 2002/000196 | 1/2002 |
| WO | WO 2002/091830 | 11/2002 |
| WO | WO 2003/062209 | 7/2003 |
| WO | WO 2003/074045 | 9/2003 |
| WO | WO 2004/014866 | 2/2004 |
| WO | WO 2004/024693 | 3/2004 |
| WO | WO 2004/030635 | 4/2004 |
| WO | WO 2004/031161 | 4/2004 |
| WO | WO 2004/039806 | 5/2004 |
| WO | WO 2004/055004 | 7/2004 |
| WO | WO 2004/080463 | 9/2004 |
| WO | WO 2005/003100 | 1/2005 |
| WO | WO 2005/007658 | 1/2005 |
| WO | WO 2005/009967 | 2/2005 |
| WO | WO 2005/028478 | 3/2005 |
| WO | WO 2005/061460 | 7/2005 |
| WO | WO 2005/072412 | 8/2005 |
| WO | WO 2005/080377 | 9/2005 |
| WO | WO 2005/082367 | 9/2005 |
| WO | WO 2005/110410 | 11/2005 |
| WO | WO 2005/112932 | 12/2005 |
| WO | WO 2005/117890 | 12/2005 |
| WO | WO 2005/121138 | 12/2005 |
| WO | WO 2006/021448 | 3/2006 |
| WO | WO 2006/032470 | 3/2006 |
| WO | WO 2006/039718 | 4/2006 |
| WO | WO 2006/045096 | 4/2006 |
| WO | WO 2006/045827 | 5/2006 |
| WO | WO 2006/065842 | 6/2006 |
| WO | WO 2006/072828 | 7/2006 |
| WO | WO 2006/074147 | 7/2006 |
| WO | WO 2006/108107 | 10/2006 |
| WO | WO 2006/122156 | 11/2006 |
| WO | WO 2007/002781 | 1/2007 |
| WO | WO 2007/007919 | 1/2007 |
| WO | WO 2007/016525 | 2/2007 |
| WO | WO 2007/022946 | 3/2007 |
| WO | WO 2007/038209 | 4/2007 |
| WO | WO 2007/047653 | 4/2007 |
| WO | WO 2007/051062 | 5/2007 |
| WO | WO 2007/076092 | 5/2007 |
| WO | WO 2007/077949 | 7/2007 |
| WO | WO 2007/110868 | 10/2007 |
| WO | WO 2007/112347 | 10/2007 |
| WO | WO 2007/113565 | 10/2007 |
| WO | WO 2007/125405 | 11/2007 |
| WO | WO 2007/133637 | 11/2007 |
| WO | WO 2007/136465 | 11/2007 |
| WO | WO 2007/140222 | 12/2007 |
| WO | WO 2007/147217 | 12/2007 |
| WO | WO 2008/000409 | 1/2008 |
| WO | WO 2008/005956 | 1/2008 |
| WO | WO 2008/007127 | 1/2008 |
| WO | WO 2008/011109 | 1/2008 |
| WO | WO 2008/011174 | 1/2008 |
| WO | WO 2008/021924 | 2/2008 |
| WO | WO 2008/024977 | 2/2008 |
| WO | WO 2008/046919 | 4/2008 |
| WO | WO 2008/060090 | 5/2008 |
| WO | WO 2008/064107 | 5/2008 |
| WO | WO 2008/079965 | 7/2008 |
| WO | WO 2008/084861 | 7/2008 |
| WO | WO 2008/092231 | 8/2008 |
| WO | WO 2008/112217 | 9/2008 |
| WO | WO 2008/113558 | 9/2008 |
| WO | WO 2008/124083 | 10/2008 |
| WO | WO 2008/135524 | 11/2008 |
| WO | WO 2008/151184 | 12/2008 |
| WO | WO 2009/024095 | 2/2009 |
| WO | WO 2009/042970 | 4/2009 |
| WO | WO 2009/114512 | 9/2009 |
| WO | WO 2010/006130 | 1/2010 |

(56) References Cited

FOREIGN PATENT DOCUMENTS

| | | |
|---|---|---|
| WO | WO 2010/026771 | 3/2010 |
| WO | WO 2010/039518 | 4/2010 |
| WO | WO 2010/042684 | 4/2010 |
| WO | WO 2010/077947 | 7/2010 |
| WO | WO 2010/078229 | 7/2010 |
| WO | WO 2010/080537 | 7/2010 |
| WO | WO 2010/101949 | 9/2010 |
| WO | WO 2010/106436 | 9/2010 |
| WO | WO 2010/107765 | 9/2010 |
| WO | WO 2010/107768 | 9/2010 |
| WO | WO 2010/123975 | 10/2010 |
| WO | WO 2010/125350 | 11/2010 |
| WO | WO 2010/129816 | 11/2010 |
| WO | WO 2010/141062 | 12/2010 |
| WO | WO 2010/143168 | 12/2010 |
| WO | WO 2010/143169 | 12/2010 |
| WO | WO 2010/143170 | 12/2010 |
| WO | WO 2011/004276 | 1/2011 |
| WO | WO 2011/022439 | 2/2011 |
| WO | WO 2011/028864 | 3/2011 |
| WO | WO 2011/047432 | 4/2011 |
| WO | WO 2011/050245 | 4/2011 |
| WO | WO 2011/053861 | 5/2011 |
| WO | WO 2011/068899 | 6/2011 |
| WO | WO 2011/072275 | 6/2011 |
| WO | WO 2011/075630 | 6/2011 |
| WO | WO 2011/078143 | 6/2011 |
| WO | WO 2011/078369 | 6/2011 |
| WO | WO 2011/086053 | 7/2011 |
| WO | WO 2011/097717 | 8/2011 |
| WO | WO 2011/103557 | 8/2011 |
| WO | WO 2011/112687 | 9/2011 |
| WO | WO 2011/123693 | 10/2011 |
| WO | WO 2011/137428 | 11/2011 |
| WO | WO 2011/146882 | 11/2011 |
| WO | WO 2012/061696 | 5/2012 |
| WO | WO 2012/066578 | 5/2012 |
| WO | WO 2012/078902 | 6/2012 |
| WO | WO 2012/085176 | 6/2012 |
| WO | WO 2012/089828 | 7/2012 |
| WO | WO 2012/097479 | 7/2012 |
| WO | WO 2012/116237 | 8/2012 |
| WO | WO 2012/127506 | 9/2012 |
| WO | WO 2013/007765 | 1/2013 |
| WO | WO 2013/033093 | 3/2013 |
| WO | WO 2013/033268 | 3/2013 |
| WO | WO 2013/033270 | 3/2013 |
| WO | WO 2013/033981 | 3/2013 |
| WO | WO 2013/049352 | 4/2013 |
| WO | WO 2013/062987 | 5/2013 |
| WO | WO 2013/067036 | 5/2013 |
| WO | WO 2013/086229 | 6/2013 |
| WO | WO 2013/156869 | 10/2013 |
| WO | WO 2013/158928 | 10/2013 |
| WO | WO 2013/167653 | 11/2013 |
| WO | WO 2013/175281 | 11/2013 |
| WO | WO 2013/191112 | 12/2013 |
| WO | WO 2014/018891 | 1/2014 |
| WO | WO 2014/023377 | 2/2014 |
| WO | WO 2014/051653 | 4/2014 |
| WO | WO 2014/074580 | 5/2014 |
| WO | WO 2014/087165 | 6/2014 |
| WO | WO 2014/120764 | 8/2014 |
| WO | WO 2014/203152 | 12/2014 |
| WO | WO 2014/204263 | 12/2014 |
| WO | WO 2015/001518 | 1/2015 |
| WO | WO 2015/009812 | 1/2015 |
| WO | WO 2015/025228 | 2/2015 |
| WO | WO 2015/036560 | 3/2015 |
| WO | WO 2015/049022 | 4/2015 |
| WO | WO 2015/086523 | 6/2015 |
| WO | WO 2015/124063 | 8/2015 |
| WO | WO 2015/144001 | 10/2015 |
| WO | WO 2015/168079 | 11/2015 |
| WO | WO 2016/009076 | 1/2016 |
| WO | WO 2016/116900 | 7/2016 |
| WO | WO 2016/123627 | 8/2016 |
| WO | WO 2016/128465 | 8/2016 |
| WO | WO 2016/160860 | 10/2016 |
| WO | WO 2016/190847 | 12/2016 |
| WO | WO 2016/197027 | 12/2016 |
| WO | WO 2017/003723 | 1/2017 |
| WO | WO 2017/004134 | 1/2017 |
| WO | WO 2017/029601 | 2/2017 |
| WO | WO 2017/059319 | 4/2017 |
| WO | WO 2017/072039 | 5/2017 |
| WO | WO 2017/072283 | 5/2017 |
| WO | WO 2017/075394 | 5/2017 |
| WO | WO 2017/090002 | 6/2017 |
| WO | WO 2017/103931 | 6/2017 |
| WO | WO 2017/205538 | 11/2017 |
| WO | WO 2017/223452 | 12/2017 |
| WO | WO 2018/009622 | 1/2018 |
| WO | WO 2018/046933 | 3/2018 |
| WO | WO 2018/057805 | 3/2018 |
| WO | WO 2018/068017 | 4/2018 |
| WO | WO 2018/083098 | 5/2018 |
| WO | WO 2018/112382 | 6/2018 |
| WO | WO 2018/140512 | 8/2018 |
| WO | WO 2018/140600 | 8/2018 |
| WO | WO 2018/144478 | 8/2018 |
| WO | WO 2018/204176 | 11/2018 |
| WO | WO 2018/204765 | 11/2018 |
| WO | WO 2018/222901 | 12/2018 |
| WO | WO 2018/231745 | 12/2018 |
| WO | WO 2018/237370 | 12/2018 |
| WO | WO 2019/060860 | 3/2019 |
| WO | WO 2019/070492 | 4/2019 |
| WO | WO 2019/129213 | 7/2019 |
| WO | WO 2019/135920 | 7/2019 |
| WO | WO 2019/177975 | 9/2019 |
| WO | WO 2019/201283 | 10/2019 |
| WO | WO 2019/214546 | 11/2019 |
| WO | WO 2021/018012 | 2/2021 |
| WO | WO 2022/006457 | 1/2022 |
| WO | WO 2022/046989 | 3/2022 |
| WO | WO 2022/064430 | 3/2022 |
| WO | WO 2022/133285 | 6/2022 |
| WO | WO 2023/036156 | 3/2023 |
| WO | WO 2023/155905 | 8/2023 |
| WO | WO 2023/178285 | 9/2023 |

OTHER PUBLICATIONS

Blom et al., "Preparative LC-MS Purification: Improved Compound Specific Method Optimization," J. Combi. Chem., 2004, 6:874-883.

Blom et al., "Optimizing Preparative LC-MS Configurations and Methods for Parallel Synthesis Purification," J. Combi. Chem., 2003, 5:670.

Blom et al., "Two-Pump at Column Dilution Configuration for Preparative LC-MS," J. Combi. Chem., 2002, 4:295.

Bricelj et al., "E3 Ligase Ligands in Successful PROTACs: An Overview of Syntheses and Linker Attachment Points," Frontiers in Chemistry, Jul. 5, 2021, 9(707317):1-46.

Brunning et al., "Myelodysplastic syndromes/neoplasms," in Chapter 5, Swerdlow, et al., (eds.), WHO Classification of Tumours of Haematopoietic and Lymphoid Tissues., 4th edition, 2008, 21 pages.

Ceesay et al., "The JAK2 V617F mutation is rare in RARS but common in RARS-T," Leukemia, 2006, 20:2060-2061.

Chilean Office Action in Chilean Application No. 202203834, dated Jan. 22, 2024, 17 pages (with English Translation).

Dommaraju et al., "An efficient catalyst- free chemoselective multicomponent reaction for the synthesis of pyrimidine functionalized pyrrolo-annelated derivatives," RSC Adv., Jan. 1, 2015, 5:24327-24335.

Eisenhauer et al., "New response evaluation criteria in solid tumours: Revised RECIST guideline (version 1.1)," European Journal of Cancer, Jan. 2009, 45(2):228-247.

Eurasian Office Action in Eurasian Application No. 202390215, dated Dec. 4, 2023, 14 pages (with English Translation).

(56) References Cited

OTHER PUBLICATIONS

European Office Action in European Application No. 22710821.4, dated Oct. 4, 2023, 3 pages.
Han et al., "PROTACs: A novel strategy for cancer drug discovery and development," MedComm., 2023, 4(e290):1-40.
Harris et al., "World Health Organization classification of neoplastic diseases of the hematopoietic and lymphoid tissues: report of the Clinical Advisory Committee meeting-Airlie House, Virginia, Nov. 1997," J. Clin. Oncol., 1999, 17:3835-3849.
Hart et al., "Structure-Based Design of Selective Janus Kinase 2 Imidazo[4,5-d]pyrrolo[2,3-b]pyridine Inhibitors," ACS Med. Chem. Lett., Aug. 13, 2015, 6(8):845-849.
International Preliminary Report on Patentability in International Application No. PCT/US2021/037870, mailed on Dec. 29, 2022, 8 pages.
International Preliminary Report on Patentability in International Application No. PCT/US2021/037877, mailed on Dec. 29, 2022, 8 pages.
International Preliminary Report on Patentability in International Application No. PCT/US2021/040182, mailed on Jan. 12, 2023, 7 pages.
International Preliminary Report on Patentability in International Application No. PCT/US2021/040185, mailed on Jan. 12, 2023, 8 pages.
International Preliminary Report on Patentability in International Application No. PCT/US2021/047687, mailed on Mar. 9, 2023, 8 pages.
International Preliminary Report on Patentability in International Application No. PCT/US2021/064295, mailed on Jun. 29, 2023, 7 pages.
International Search Report and Written Opinion in International Application No. PCT/US2021/037870, dated Aug. 13, 2021, 13 pages.
International Search Report and Written Opinion in International Application No. PCT/US2021/037877, dated Aug. 13, 2021, 10 pages.
International Search Report and Written Opinion in International Application No. PCT/US2021/040182, dated Sep. 22, 2021, 12 pages.
International Search Report and Written Opinion in International Application No. PCT/US2021/040185, dated Sep. 22, 2021, 15 pages.
International Search Report and Written Opinion in International Application No. PCT/US2021/047687, dated Nov. 19, 2021, 16 pages.
International Search Report and Written Opinion in International Application No. PCT/US2021/064295, dated Mar. 17, 2022, 15 pages.
International Search Report and Written Opinion in International Application No. PCT/US2022/017654, dated May 30, 2022, 22 pages.
International Search Report and Written Opinion in International Application No. PCT/US2023/035498, dated Jan. 18, 2024, 11 pages.
International Search Report and Written Opinion in International Application No. PCT/US2023/064593, dated May 17, 2023, 14 pages.
James et al., "A unique clonal JAK2 mutation leading to constitutive signaling causes polycythaemia vera," Nature, 2005, 434:1144-1148.
Jisha et al., "Exploration of 3,6-dihydroimidazo(4,5-d)pyrrolo(2,3-b)pyridin-2(1H)-one derivatives as JAK inhibitors using various in silico techniques," In Silico Pharmacology, 2017, 5(1):1-23.
Kargbo, "Degradation of Janus Kinase for Potential Application in Immune Response Therapeutics," ACS Med. Chem. Lett., 2021, 12(3):316-317.
Kerekes et al., "Aurora kinase inhibitors based on the imidazo[1,2-a]pyrazine core: fluorine and deuterium incorporation improve oral absorption and exposure," J. Med. Chem., 2011, 54:201-210.

Khalaf et al., "Structure-based design and synthesis of antiparasitic pyrrolopyrimidines targeting pteridine reductase 1," J. Med. Chem., Jul. 9, 2014, 57(15):6479-6494.
Kralovics et al., "A gain-of-function mutation of JAK2 in myeloproliferative disorders," N. Engl. J. Med., 2005, 352:1779-1790.
Kulagawski et al., "Identification of imidazo-pyrrolopyridines as novel and potent JAK1 inhibitors," J. Med. Chem., 2012, 55(12):5901-5921.
Labadie et al., "Design and evaluation of novel 8-oxo-pyridopyrimidine Jak1/2 inhibitors," Bioorg. Med. Chem. Lett., Nov. 2013, 23(21):5923-5930.
Leroy et al., "Differential effect of inhibitory strategies of the V617 mutant of JAK2 on cytokine receptor signaling," Journal of Allergy and Clinical Immunology, Jul. 2019, 144(1):224-235.
Levine et al., "Activating mutation in the tyrosine kinase JAK2 in polycythemia vera, essential thrombocythemia, and myeloid metaplasia with myelofibrosis," Cancer Cell., 2005, 7:387-397.
Ma et al., "Mutation Profile of JAK2 Transcripts in Patients with Chronic Myeloproliferative Neoplasias," J. Mol. Diagn., Jan. 2009, 11(1):49-53.
Quiroga et al., "Generation of pyrrolo[2,3-d]pyrimidines. Unexpected products in the multicomponent reaction of 6-aminopyrimidines, dimedone, and arylglyoxal," Tetrahedron Letters, Oct. 2010, 51(41):5443-5447.
Remington's Pharmaceutical Sciences, 17th ed., Mack Publishing Company, Easton, Pa., 1985, p. 1418.
Scott et al., "JAK2 Exon 12 Mutations in Polycythemia Vera and Idiopathic Erythrocytosis," The New England Journal of Medicine, Feb. 1, 2007, 356:459-68.
Steinebach et al., "Leveraging Ligand Affinity and Properties: Discovery of Novel Benzamide-Type Cereblon Binders for the Design of PROTACs," Journal of Medical Chemistry, 2023, 66:14513-14543.
STN Search Report, Conducted Dec. 10, 2019, 379 pages.
STN Search Report, Conducted Dec. 2019, 1 page.
STN Search Report, Conducted Dec. 2020, 11 pages.
STN Search Report, Conducted Jun. 19, 2021, 236 pages.
STN Search Report, Conducted Jun. 2019, 13 pages.
STN Search Report, Conducted Jun. 2019, 292 pages.
STN Search Report, Conducted Jun. 2019, 316 pages.
STN Search Report, Conducted Jun. 2019, 39 pages.
STN Search Report, Conducted Oct. 2019, 14 pages.
STN Search Report, Conducted Sep. 2019, 236 pages.
STN Search Report, Conducted Sep. 2019, 5 pages.
Vainchecker et al., "JAK inhibitors for the treatment of myeloproliferative neoplasms and other disorders," F1000Research., 2018, 7:82.
Vardiman et al., "The 2008 revision of the World Health Organization (WHO) classification of myeloid neoplasms and acute leukemia: rationale and important changes, " Blood 2009, 114:937-951.
Vardiman et al., "The World Health Organization (WHO) classification of the myeloid neoplasms," Blood 2002, 100:2292-2302.
Wilmes et al., "Mechanism of homodimeric cytokine receptor activation and dysregulation by oncogenic mutations," Science, 2020, 367:643-652.
Woods et al., "Activation of JAK/STAT Signaling in Megakaryocytes Sustains Myeloproliferation In Vivo," Clin. Cancer Res., 2019, 25(19):5901-5912.
Xu et al., "Design, synthesis and biological evaluation of deuterated nintedanib for improving pharmacokinetic properties," J. Label Compd. Radiopharm., 2015, 58:308-312.
Yamagishi et al., "Discovery of 3,6-dihydroimidazo[4,5-d]pyrrolo[2,3-b]pyridin-2(1H)-one derivatives as novel JAK inhibitors," Bioorg. & Med. Chem., 2015, 23(15):4846-4859.
Yamagishi et al., "Discovery of tricyclic dipyrrolopyridine derivatives as novel JAK inhibitors," Bioorg. & Med. Chem., 2017, 25(20):5311-5326.
Yang et al., "Three-component reaction for synthesis of 2-amino-6-aryl-5-(phenylamino)-3,7-dihydro-4H-pyrrolo[2,3-d]pyrimidin-4-one derivatives in water," J. Hetero. Chem., 2020, 57(9):3271-3278.

(56) References Cited

OTHER PUBLICATIONS

Zak et al., "Discovery and optimization of C-2 methyl imidazopyrrolopyridines as potent and orally bioavailable JAK1 inhibitors with selectivity over JAK2," J. Med. Chem., 2012, 55(13):6176-6193.

* cited by examiner

TRICYCLIC UREA COMPOUNDS AS JAK2 V617F INHIBITORS

TECHNICAL FIELD

The present invention provides tricyclic urea compounds that modulate the activity of the V617F variant of JAK2 and are useful in the treatment of diseases related to the V617F variant of JAK2, including cancer.

BACKGROUND

Janus kinase (JAK) 2 plays pivotal roles in signaling by several cytokine receptors. The mutant JAK2 V617F is the most common molecular event associated with myeloproliferative neoplasms. Selective targeting of the JAK2 V617F mutant may be useful for treating various pathologies, while sparing essential JAK2 functions. This application is directed to this need and others.

SUMMARY

The present invention relates to, inter alia, compounds of Formula I.

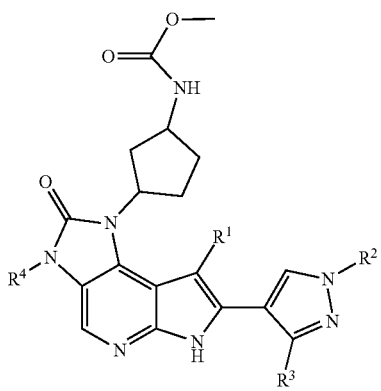

or pharmaceutically acceptable salts thereof, wherein constituent members are defined herein.

The present invention further provides pharmaceutical compositions comprising a compound of Formula I, or a pharmaceutically acceptable salt thereof, and a pharmaceutically acceptable carrier.

The present invention further provides methods of inhibiting an activity of the V617F variant of JAK2 kinase comprising contacting the kinase with a compound of Formula I, or a pharmaceutically acceptable salt thereof.

The present invention further provides methods of treating a disease or a disorder associated with expression or activity of the V617F variant of JAK2 kinase in a patient by administering to a patient a therapeutically effective amount of a compound of Formula I, or a pharmaceutically acceptable salt thereof.

The present invention further provides a compound of Formula I, or a pharmaceutically acceptable salt thereof, for use in any of the methods described herein.

The present invention further provides use of a compound of Formula I, or a pharmaceutically acceptable salt thereof, for the preparation of a medicament for use in any of the methods described herein.

DETAILED DESCRIPTION

The present application provides a compound of Formula I:

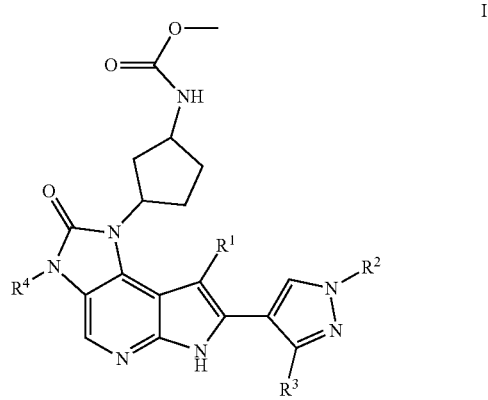

or a pharmaceutically acceptable salt thereof, wherein:
  $R^1$ is selected from phenyl, indazolyl, and dihydroisobenzofuranyl, each of which is optionally substituted by 1, 2, or 3 substituents independently selected from halo, $C_{1-6}$ alkyl, $C_{1-6}$ alkoxy, $C_{1-6}$ haloalkyl, and $C_{1-6}$ hydroxyalkyl;
  $R^2$ is $C_{1-6}$ alkyl or $C_{1-6}$ haloalkyl;
  $R^3$ is selected from halo, $C_{1-6}$ alkyl, and $C_{1-6}$ alkoxy; and
  $R^4$ is $C_{1-6}$ alkyl.
In some embodiments:
  $R^1$ is selected from phenyl and indazolyl, each of which is optionally substituted by 1, 2, or 3 substituents independently selected from halo, $C_{1-6}$ alkyl, and $C_{1-6}$ alkoxy;
  $R^2$ is $C_{1-6}$ alkyl;
  $R^3$ is selected from halo, $C_{1-6}$ alkyl, and $C_{1-6}$ alkoxy; and
  $R^4$ is $C_{1-6}$ alkyl.

In some embodiments, $R^1$ is selected from phenyl, indazolyl, and dihydroisobenzofuranyl, each of which is optionally substituted by 1, 2, or 3 substituents independently selected from fluoro, methyl, isopropyl, trideuteromethyl, difluoroethyl, methoxy, trideuteromethoxy, and hydroxyisopropyl.

In some embodiments, $R^1$ is selected from phenyl, indazolyl, and dihydroisobenzofuranyl, each of which is optionally substituted by 1 or 2 substituents independently selected from fluoro, methyl, isopropyl, trideuteromethyl, difluoroethyl, methoxy, trideuteromethoxy, and hydroxyisopropyl.

In some embodiments, $R^1$ is dihydroisobenzofuranyl, which is optionally substituted by 1, 2, or 3 substituents independently selected from halo, $C_{1-6}$ alkyl, and $C_{1-6}$ alkoxy.

In some embodiments, $R^1$ is dihydroisobenzofuranyl, which is optionally substituted by 1, 2, or 3 independently selected $C_{1-6}$ alkyl substituents.

In some embodiments, $R^1$ is dihydroisobenzofuranyl, which is optionally substituted by 1, 2, or 3 independently selected $C_{1-3}$ alkyl substituents.

In some embodiments, $R^1$ is dihydroisobenzofuranyl, which is optionally substituted by 1 or 2 independently selected $C_{1-3}$ alkyl substituents.

In some embodiments, $R^1$ is dihydroisobenzofuranyl, which is optionally substituted by 1, 2, or 3 methyl substituents.

In some embodiments, $R^1$ is dihydroisobenzofuranyl, which is optionally substituted by 1 or 2 methyl substituents.

In some embodiments, $R^1$ is dihydroisobenzofuranyl, which is substituted by 1 or 2 independently selected $C_{1-6}$ alkyl substituents.

In some embodiments, $R^1$ is dihydroisobenzofuranyl, which is substituted by 1 or 2 independently selected $C_{1-3}$ alkyl substituents.

In some embodiments, $R^1$ is dihydroisobenzofuranyl, which is substituted by 1 or 2 methyl substituents.

In some embodiments, $R^1$ is selected from phenyl and indazolyl, each of which is optionally substituted by 1 or 2 substituents independently selected from fluoro, trideuteromethyl, and methoxy.

In some embodiments, $R^1$ is selected from phenyl, fluorophenyl, trideuteromethoxyphenyl, (hydroxyisopropyl)phenyl, fluoromethoxyphenyl, dimethyldihydroisobenzofuranyl, isopropylindazolyl, (fluoro)(trideuteromethyl)indazolyl, and difluoroethylindazolyl.

In some embodiments, $R^1$ is selected from trideuteromethoxyphenyl, (hydroxyisopropyl)phenyl, dimethyldihydroisobenzofuranyl, isopropylindazolyl, (fluoro)(trideuteromethyl)indazolyl, and difluoroethylindazolyl.

In some embodiments, $R^1$ is selected from phenyl, fluorophenyl, fluoromethoxyphenyl, and trideuteromethylindazolyl.

In some embodiments, $R^1$ is selected from phenyl, 3-fluorophenyl, 4-fluorophenyl, 3-fluoro-4-methoxyphenyl, and 1-(trideuteromethyl)-1H-indazol-5-yl.

In some embodiments $R^1$ is selected from:

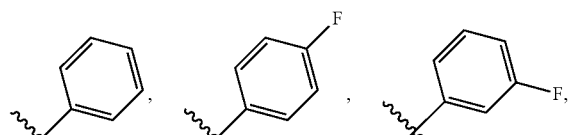

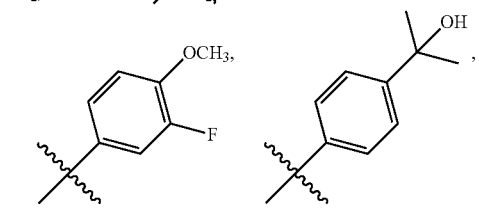

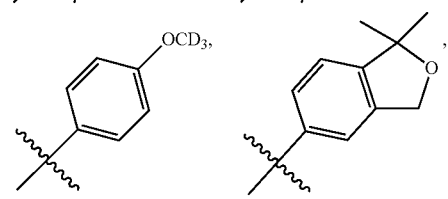

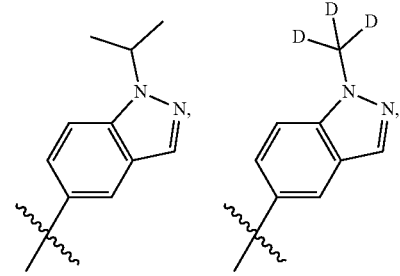

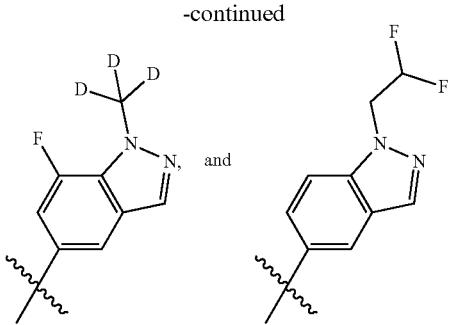

In some embodiments, $R^1$ is selected from:

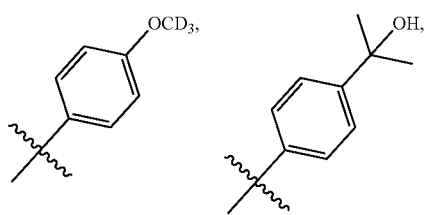

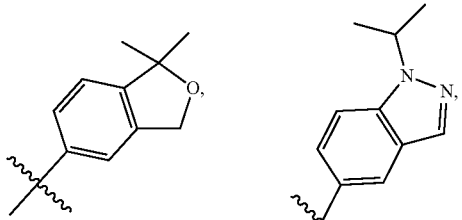

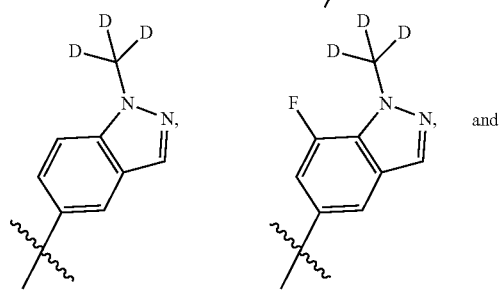

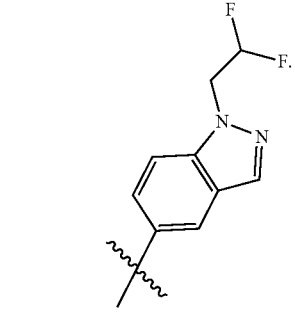

In some embodiments, $R^1$ is phenyl.
In some embodiments, $R^1$ is fluorophenyl.
In some embodiments, $R^1$ is 3-fluorophenyl.
In some embodiments, $R^1$ is 4-fluorophenyl.
In some embodiments, $R^1$ is fluoromethoxyphenyl.
In some embodiments, $R^1$ is 3-fluoro-4-methoxyphenyl.
In some embodiments, $R^1$ is trideuteromethylindazolyl.
In some embodiments, $R^1$ is 1-(trideuteromethyl)-1H-indazol-5-yl.

In some embodiments, $R^1$ is trideuteromethoxyphenyl.
In some embodiments, $R^1$ is 4-trideuteromethoxyphenyl.
In some embodiments, $R^1$ is (hydroxypropan-2-yl)phenyl.
In some embodiments, $R^1$ is 4-(2-hydroxypropan-2-yl)phenyl.
In some embodiments, $R^1$ is dimethyldihydroisobenzofuranyl.
In some embodiments, $R^1$ is 1,1-dimethyl-1,3-dihydroisobenzofuranyl.
In some embodiments, $R^1$ is 1,1-dimethyl-1,3-dihydroisobenzofuran-5-yl.
In some embodiments, $R^1$ is isopropylindazolyl.
In some embodiments, $R^1$ is 1-isopropyl-1H-indazol-5-yl.
In some embodiments, $R^1$ is (fluoro)(trideuteromethyl)indazolyl.
In some embodiments, $R^1$ is 7-fluoro-1-trideuteromethyl-1H-indazol-5-yl.
In some embodiments, $R^1$ is difluoroethylindazolyl.
In some embodiments, $R^1$ is 1-(2,2-difluoroethyl)-1H-indazol-5-yl.
In some embodiments, $R^2$ is $C_{1-3}$ alkyl or $C_{1-3}$ haloalkyl.
In some embodiments, $R^2$ is methyl, ethyl, trideuteromethyl, difluoroethyl, pentadeuteroethyl, and heptadeuteroisopropyl.
In some embodiments, $R^2$ is $C_{1-6}$ haloalkyl.
In some embodiments, $R^2$ is $C_{1-3}$ haloalkyl.
In some embodiments, $R^2$ is difluoroethyl.
In some embodiments, $R^2$ is 2,2-difluoroethyl.
In some embodiments, $R^2$ is $C_{1-6}$ alkyl.
In some embodiments, $R^2$ is $C_{1-3}$ alkyl.
In some embodiments, $R^2$ is ethyl.
In some embodiments, $R^2$ is trideuteromethyl.
In some embodiments, $R^2$ is pentadeuteroethyl.
In some embodiments, $R^2$ is heptadeuteroisopropyl.
In some embodiments, $R^3$ is $C_{1-6}$ alkoxy or halo.
In some embodiments, $R^3$ is $C_{1-3}$ alkoxy or halo.
In some embodiments, $R^3$ is $C_{1-6}$ alkoxy or fluoro.
In some embodiments, $R^3$ is $C_{1-3}$ alkoxy or fluoro.
In some embodiments, $R^3$ is $C_{1-6}$ alkoxy.
In some embodiments, $R^3$ is $C_{1-3}$ alkoxy.
In some embodiments, $R^3$ is methoxy or fluoro.
In some embodiments, $R^3$ is methoxy.
In some embodiments, $R^3$ is fluoro.
In some embodiments, $R^4$ is $C_{1-3}$ alkyl.
In some embodiments, $R^4$ is methyl.
In some embodiments, $R^4$ is trideuteromethyl.
In some embodiments:
$R^1$ is selected from phenyl, indazolyl, and dihydroisobenzofuranyl, each of which is optionally substituted by 1 or 2 substituents independently selected from halo, $C_{1-3}$ alkyl, $C_{1-3}$ alkoxy, $C_{1-3}$ haloalkyl, and $C_{1-3}$ hydroxyalkyl;
$R^2$ is $C_{1-3}$ alkyl or $C_{1-3}$ haloalkyl;
$R^3$ is selected from halo, $C_{1-3}$ alkyl, and $C_{1-3}$ alkoxy; and
$R^4$ is $C_{1-3}$ alkyl.
In some embodiments:
$R^1$ is selected from phenyl, indazolyl, and dihydroisobenzofuranyl, each of which is optionally substituted by 1 or 2 substituents independently selected from fluoro, methyl, isopropyl, trideuteromethyl, difluoroethyl, methoxy, trideuteromethoxy, and hydroxyisopropyl;
$R^2$ is selected from methyl, ethyl, trideuteromethyl, difluoroethyl, pentadeuteroethyl, and heptadeuteroisopropyl;
$R^3$ is methoxy or fluoro; and
$R^4$ is methyl or trideuteromethyl.

In some embodiments:
$R^1$ is selected from 3-fluorophenyl, 4-fluorophenyl, 3-fluoro-4-methoxyphenyl, 1-(trideuteromethyl)-1H-indazol-5-yl, 4-trideuteromethoxyphenyl, 4-(2-hydroxypropan-2-yl)phenyl, 1,1-dimethyl-1,3-dihydroisobenzofuran-5-yl, 1-isopropyl-1H-indazol-5-yl, 7-fluoro-1-trideuteromethyl-1H-indazol-5-yl, and 1-(2,2-difluoroethyl)-1H-indazol-5-yl;
$R^2$ is $C_{1-6}$ alkyl or $C_{1-6}$ haloalkyl;
$R^3$ is selected from halo, $C_{1-6}$ alkyl, and $C_{1-6}$ alkoxy; and
$R^4$ is $C_{1-6}$ alkyl.
In some embodiments:
$R^1$ is selected from 3-fluorophenyl, 4-fluorophenyl, 3-fluoro-4-methoxyphenyl, 1-(trideuteromethyl)-1H-indazol-5-yl, 4-trideuteromethoxyphenyl, 4-(2-hydroxypropan-2-yl)phenyl, 1,1-dimethyl-1,3-dihydroisobenzofuran-5-yl, 1-isopropyl-1H-indazol-5-yl, 7-fluoro-1-trideuteromethyl-1H-indazol-5-yl, and 1-(2,2-difluoroethyl)-1H-indazol-5-yl;
$R^2$ is $C_{1-6}$ alkyl or $C_{1-6}$ haloalkyl;
$R^3$ is selected from halo, $C_{1-6}$ alkyl, and $C_{1-6}$ alkoxy; and
$R^4$ is $C_{1-6}$ alkyl.
In some embodiments:
$R^1$ is selected from 3-fluorophenyl, 4-fluorophenyl, 3-fluoro-4-methoxyphenyl, 1-(trideuteromethyl)-1H-indazol-5-yl, 4-trideuteromethoxyphenyl, 4-(2-hydroxypropan-2-yl)phenyl, 1,1-dimethyl-1,3-dihydroisobenzofuran-5-yl, 1-isopropyl-1H-indazol-5-yl, 7-fluoro-1-trideuteromethyl-1H-indazol-5-yl, and 1-(2,2-difluoroethyl)-1H-indazol-5-yl;
$R^2$ is $C_{1-3}$ alkyl or $C_{1-3}$ haloalkyl;
$R^3$ is selected from halo, $C_{1-3}$ alkyl, and $C_{1-3}$ alkoxy; and
$R^4$ is $C_{1-3}$ alkyl.
In some embodiments:
$R^1$ is selected from 3-fluorophenyl, 4-fluorophenyl, 3-fluoro-4-methoxyphenyl, 1-(trideuteromethyl)-1H-indazol-5-yl, 4-trideuteromethoxyphenyl, 4-(2-hydroxypropan-2-yl)phenyl, 1,1-dimethyl-1,3-dihydroisobenzofuran-5-yl, 1-isopropyl-1H-indazol-5-yl, 7-fluoro-1-trideuteromethyl-1H-indazol-5-yl, and 1-(2,2-difluoroethyl)-1H-indazol-5-yl;
$R^2$ is selected from methyl, ethyl, trideuteromethyl, difluoroethyl, pentadeuteroethyl, and heptadeuteroisopropyl;
$R^3$ is methoxy or fluoro; and
$R^4$ is $C_{1-3}$ alkyl.
In some embodiments:
$R^1$ is selected from 3-fluorophenyl, 4-fluorophenyl, 3-fluoro-4-methoxyphenyl, 1-(trideuteromethyl)-1H-indazol-5-yl, 4-trideuteromethoxyphenyl, 4-(2-hydroxypropan-2-yl)phenyl, 1,1-dimethyl-1,3-dihydroisobenzofuran-5-yl, 1-isopropyl-1H-indazol-5-yl, 7-fluoro-1-trideuteromethyl-1H-indazol-5-yl, and 1-(2,2-difluoroethyl)-1H-indazol-5-yl;
$R^2$ is selected from methyl, ethyl, trideuteromethyl, difluoroethyl, pentadeuteroethyl, and heptadeuteroisopropyl;
$R^3$ is methoxy or fluoro; and
$R^4$ is methyl or trideuteromethyl.
In some embodiments:
$R^1$ is selected from 3-fluorophenyl, 4-fluorophenyl, 3-fluoro-4-methoxyphenyl, 1-(trideuteromethyl)-1H-indazol-5-yl, 4-trideuteromethoxyphenyl, 4-(2-hydroxypropan-2-yl)phenyl, 1,1-dimethyl-1,3-dihydroisobenzofuran-5-yl, 1-isopropyl-1H-indazol-5-yl, 7-fluoro-1-trideuteromethyl-1H-indazol-5-yl, and 1-(2, 2-difluoroethyl)-1H-indazol-5-yl;

R² is selected from methyl, ethyl, trideuteromethyl, difluoroethyl, pentadeuteroethyl, and heptadeuteroisopropyl;
R³ is selected from halo, $C_{1-3}$ alkyl, and $C_{1-3}$ alkoxy; and
R⁴ is $C_{1-3}$ alkyl.

In some embodiments:
R¹ is selected from phenyl and indazolyl, each of which is optionally substituted by 1 or 2 substituents independently selected from halo, $C_{1-3}$ alkyl, and $C_{1-3}$ alkoxy;
R² is $C_{1-3}$ alkyl;
R³ is selected from halo, $C_{1-3}$ alkyl, and $C_{1-3}$ alkoxy; and
R⁴ is $C_{1-3}$ alkyl.

In some embodiments:
R¹ is selected from phenyl and indazolyl, each of which is optionally substituted by 1 or 2 substituents independently selected from fluoro, trideuteromethyl, and methoxy;
R² is methyl or trideuteromethyl;
R³ is methoxy or fluoro; and
R⁴ is methyl or trideuteromethyl.

In some embodiments:
R¹ is selected from phenyl and indazolyl, each of which is optionally substituted by 1 or 2 substituents independently selected from fluoro, trideuteromethyl, and methoxy;
R² is methyl;
R³ is methoxy; and
R⁴ is methyl.

In some embodiments:
R¹ is selected from phenyl, fluorophenyl, fluoromethoxyphenyl, and trideuteromethylindazolyl;
R² is $C_{1-3}$ alkyl;
R³ is $C_{1-3}$ alkoxy or halo; and
R⁴ is $C_{1-3}$ alkyl.

In some embodiments:
R¹ is selected from phenyl, fluorophenyl, fluoromethoxyphenyl, and trideuteromethylindazolyl;
R² is $C_{1-3}$ alkyl;
R³ is $C_{1-3}$ alkoxy; and
R⁴ is $C_{1-3}$ alkyl.

In some embodiments:
R¹ is selected from phenyl, fluorophenyl, fluoromethoxyphenyl, and trideuteromethylindazolyl;
R² is $C_{1-3}$ alkyl;
R³ is $C_{1-3}$ alkoxy or halo; and
R⁴ is methyl or trideuteromethyl.

In some embodiments:
R¹ is selected from phenyl, fluorophenyl, fluoromethoxyphenyl, and trideuteromethylindazolyl;
R² is $C_{1-3}$ alkyl;
R³ is $C_{1-3}$ alkoxy; and
R⁴ is methyl or trideuteromethyl.

In some embodiments:
R¹ is selected from phenyl, fluorophenyl, fluoromethoxyphenyl, and trideuteromethylindazolyl;
R² is $C_{1-3}$ alkyl;
R³ is $C_{1-3}$ alkoxy; and
R⁴ is methyl.

In some embodiments:
R¹ is selected from phenyl, fluorophenyl, fluoromethoxyphenyl, and trideuteromethylindazolyl;
R² is methyl or trideuteromethyl;
R³ is methoxy or fluoro; and
R⁴ is methyl or trideuteromethyl.

In some embodiments:
R¹ is selected from phenyl, fluorophenyl, fluoromethoxyphenyl, and trideuteromethylindazolyl;
R² is methyl;
R³ is methoxy; and
R⁴ is methyl.

In some embodiments:
R¹ is selected from phenyl, 3-fluorophenyl, 4-fluorophenyl, 3-fluoro-4-methoxyphenyl, and 1-(trideuteromethyl)-1H-indazol-5-yl;
R² is $C_{1-3}$ alkyl;
R³ is $C_{1-3}$ alkoxy or halo; and
R⁴ is $C_{1-3}$ alkyl.

In some embodiments:
R¹ is selected from phenyl, 3-fluorophenyl, 4-fluorophenyl, 3-fluoro-4-methoxyphenyl, and 1-(trideuteromethyl)-1H-indazol-5-yl;
R² is $C_{1-3}$ alkyl;
R³ is $C_{1-3}$ alkoxy; and
R⁴ is $C_{1-3}$ alkyl.

In some embodiments:
R¹ is selected from phenyl, 3-fluorophenyl, 4-fluorophenyl, 3-fluoro-4-methoxyphenyl, and 1-(trideuteromethyl)-1H-indazol-5-yl;
R² is $C_{1-3}$ alkyl;
R³ is $C_{1-3}$ alkoxy or halo; and
R⁴ is methyl or trideuteromethyl.

In some embodiments:
R¹ is selected from phenyl, 3-fluorophenyl, 4-fluorophenyl, 3-fluoro-4-methoxyphenyl, and 1-(trideuteromethyl)-1H-indazol-5-yl;
R² is methyl or trideuteromethyl;
R³ is $C_{1-3}$ alkoxy or halo; and
R⁴ is methyl or trideuteromethyl.

In some embodiments:
R¹ is selected from phenyl, 3-fluorophenyl, 4-fluorophenyl, 3-fluoro-4-methoxyphenyl, and 1-(trideuteromethyl)-1H-indazol-5-yl;
R² is $C_{1-3}$ alkyl;
R³ is $C_{1-3}$ alkoxy; and
R⁴ is methyl or trideuteromethyl.

In some embodiments:
R¹ is selected from phenyl, 3-fluorophenyl, 4-fluorophenyl, 3-fluoro-4-methoxyphenyl, and 1-(trideuteromethyl)-1H-indazol-5-yl;
R² is methyl or trideuteromethyl;
R³ is methoxy or fluoro; and
R⁴ is methyl or trideuteromethyl.

In some embodiments:
R¹ is selected from phenyl, 3-fluorophenyl, 4-fluorophenyl, 3-fluoro-4-methoxyphenyl, and 1-(trideuteromethyl)-1H-indazol-5-yl;
R² is $C_{1-3}$ alkyl;
R³ is $C_{1-3}$ alkoxy; and
R⁴ is methyl.

In some embodiments, the compound of Formula I is a compound of Formula Ia:

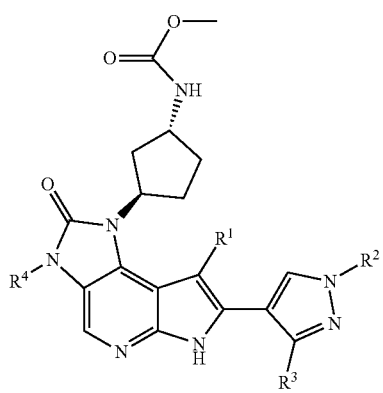

Ia or a pharmaceutically acceptable salt thereof.

In some embodiments, the compound of Formula I is a compound of Formula II:

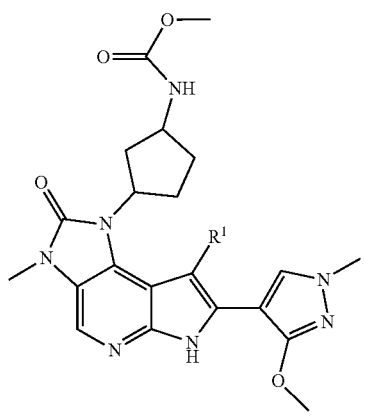

II or a pharmaceutically acceptable salt thereof.

In some embodiments, the compound of Formula I is a compound of Formula IIa:

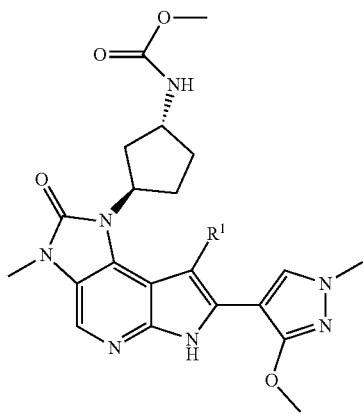

IIa or a pharmaceutically acceptable salt thereof.

In some embodiments, the compound of Formula I is a compound of Formula III:

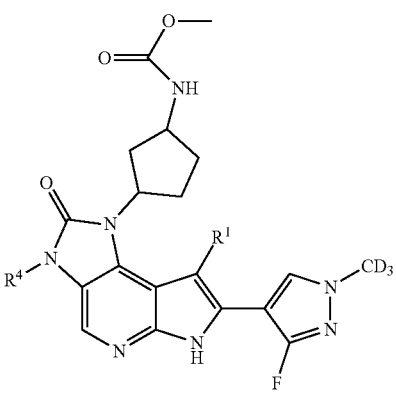

III or a pharmaceutically acceptable salt thereof.

In some embodiments, the compound of Formula I is a compound of Formula

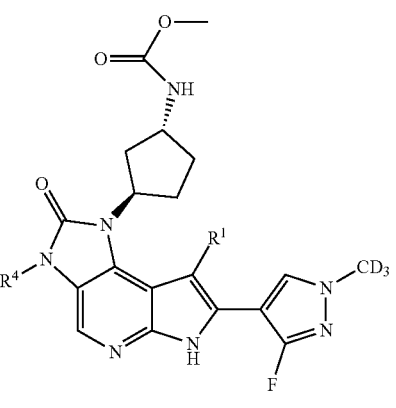

IIIa or a pharmaceutically acceptable salt thereof.

In some embodiments, the compound of Formula I is a compound of Formula IV:

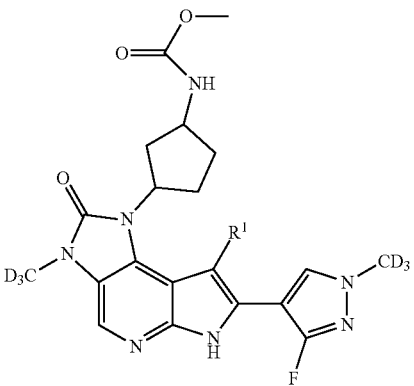

IV or a pharmaceutically acceptable salt thereof.

In some embodiments, the compound of Formula I is a compound of Formula IVa:

IVa

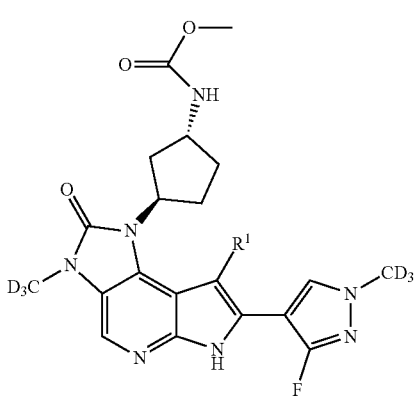

or a pharmaceutically acceptable salt thereof.

In some embodiments, the compound of Formula I is a compound of Formula V:

V

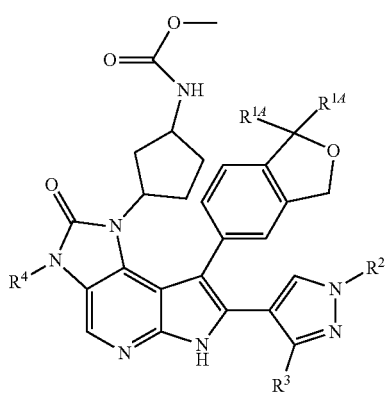

or a pharmaceutically acceptable salt thereof, wherein each $R^{1A}$ is independently selected from halo, $C_{1-6}$ alkyl, $C_{1-6}$ alkoxy, $C_{1-6}$ haloalkyl, and $C_{1-6}$ hydroxyalkyl.

In some embodiments, the compound of Formula I is a compound of Formula Va:

Va

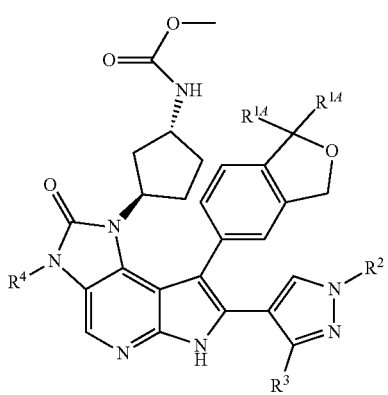

or a pharmaceutically acceptable salt thereof, wherein each $R^{1A}$ is independently selected from halo, $C_{1-6}$ alkyl, $C_{1-6}$ alkoxy, $C_{1-6}$ haloalkyl, and $C_{1-6}$ hydroxyalkyl.

In some embodiments of Formulas V and Va, each $R^{1A}$ is an independently selected $C_{1-6}$ alkyl.

In some embodiments of Formulas V and Va, each $R^{1A}$ is an independently selected $C_{1-3}$ alkyl.

In some embodiments, the compound of Formula I is a compound of Formula Vb:

Vb

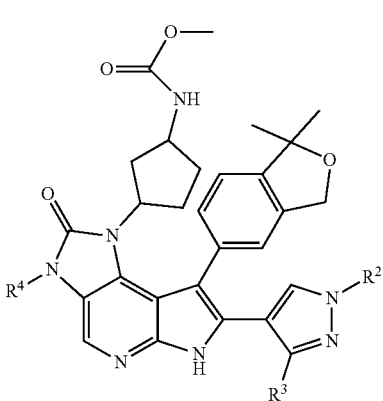

or a pharmaceutically acceptable salt thereof.

In some embodiments, the compound of Formula I is a compound of Formula Vc:

Vc

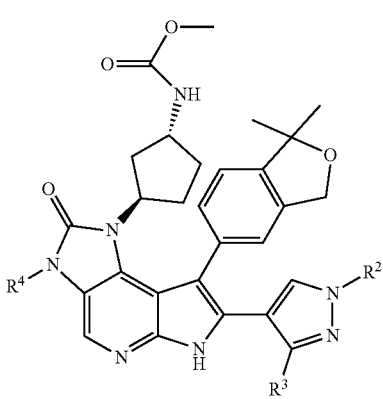

or a pharmaceutically acceptable salt thereof.

In some embodiments, the compound of Formula I is selected from:

methyl ((1R,3R)-3-(8-(4-fluorophenyl)-7-(3-methoxy-1-methyl-1H-pyrazol-4-yl)-3-methyl-2-oxo-3,6-dihydroimidazo[4,5-d]pyrrolo[2,3-b]pyridin-1(2H)-yl)cyclopentyl)carbamate;

methyl ((1R,3R)-3-(7-(3-methoxy-1-methyl-1H-pyrazol-4-yl)-3-methyl-2-oxo-8-phenyl-3,6-dihydroimidazo[4,5-d]pyrrolo[2,3-b]pyridin-1(2H)-yl)cyclopentyl)carbamate;

methyl ((1R,3R)-3-(8-(3-fluorophenyl)-7-(3-methoxy-1-methyl-1H-pyrazol-4-yl)-3-methyl-2-oxo-3,6-dihydroimidazo[4,5-d]pyrrolo[2,3-b]pyridin-1(2H)-yl)cyclopentyl)carbamate;

methyl ((1R,3R)-3-(8-(3-fluoro-4-methoxyphenyl)-7-(3-methoxy-1-methyl-1H-pyrazol-4-yl)-3-methyl-2-oxo-3,6-dihydroimidazo[4,5-d]pyrrolo[2,3-b]pyridin-1(2H)-yl)cyclopentyl)carbamate;

methyl ((1R,3R)-3-(7-(3-methoxy-1-methyl-1H-pyrazol-4-yl)-3-methyl-8-(1-(methyl-d₃)-1H-indazol-5-yl)-2-oxo-3,6-dihydroimidazo[4,5-d]pyrrolo[2,3-b]pyridin-1(2H)-yl)cyclopentyl)carbamate;

methyl ((1R,3R)-3-(7-(3-fluoro-1-(methyl-d₃)-1H-pyrazol-4-yl)-3-(methyl-d₃)-8-(1-(methyl-d₃)-1H-indazol-5-yl)-2-oxo-3,6-dihydroimidazo[4,5-d]pyrrolo[2,3-b]pyridin-1(2H)-yl)cyclopentyl)carbamate;

methyl ((1R,3R)-3-(7-(3-fluoro-1-(methyl-d₃)-1H-pyrazol-4-yl)-8-(4-fluorophenyl)-3-(methyl-d₃)-2-oxo-3,6-dihydroimidazo[4,5-d]pyrrolo[2,3-b]pyridin-1(2H)-yl)cyclopentyl)carbamate;

methyl ((1R,3R)-3-(8-(1,1-dimethyl-1,3-dihydroisobenzofuran-5-yl)-7-(3-fluoro-1-(methyl-d3)-1H-pyrazol-4-yl)-3-(methyl-d3)-2-oxo-3,6-dihydroimidazo[4,5-d]pyrrolo[2,3-b]pyridin-1(2H)-yl)cyclopentyl)carbamate;

methyl ((1R,3R)-3-(7-(3-fluoro-1-(methyl-d3)-1H-pyrazol-4-yl)-8-(4-(methoxy-d3)phenyl)-3-(methyl-d3)-2-oxo-3,6-dihydroimidazo[4,5-d]pyrrolo[2,3-b]pyridin-1(2H)-yl)cyclopentyl)carbamate;

methyl ((1R,3R)-3-(7-(3-fluoro-1-(methyl-d3)-1H-pyrazol-4-yl)-8-(4-(2-hydroxypropan-2-yl)phenyl)-3-(methyl-d3)-2-oxo-3,6-dihydroimidazo[4,5-d]pyrrolo[2,3-b]pyridin-1(2H)-yl)cyclopentyl)carbamate;

methyl ((1R,3R)-3-(8-(1,1-dimethyl-1,3-dihydroisobenzofuran-5-yl)-7-(3-fluoro-1-(methyl-d3)-1H-pyrazol-4-yl)-3-methyl-2-oxo-3,6-dihydroimidazo[4,5-d]pyrrolo[2,3-b]pyridin-1(2H)-yl)cyclopentyl)carbamate;

methyl ((1R,3R)-3-(7-(1-(2,2-difluoroethyl)-3-fluoro-1H-pyrazol-4-yl)-8-(1,1-dimethyl-1,3-dihydroisobenzofuran-5-yl)-3-(methyl-d3)-2-oxo-3,6-dihydroimidazo[4,5-d]pyrrolo[2,3-b]pyridin-1(2H)-yl)cyclopentyl)carbamate;

methyl ((1R,3R)-3-(7-(3-fluoro-1-(methyl-d3)-1H-pyrazol-4-yl)-8-(1-isopropyl-1H-indazol-5-yl)-3-(methyl-d3)-2-oxo-3,6-dihydroimidazo[4,5-d]pyrrolo[2,3-b]pyridin-1(2H)-yl)cyclopentyl)carbamate;

methyl ((1R,3R)-3-(8-(1-(2,2-difluoroethyl)-1H-indazol-5-yl)-7-(3-fluoro-1-(methyl-d3)-1H-pyrazol-4-yl)-3-(methyl-d3)-2-oxo-3,6-dihydroimidazo[4,5-d]pyrrolo[2,3-b]pyridin-1(2H)-yl)cyclopentyl)carbamate;

methyl ((1R,3R)-3-(7-(1-(ethyl-d5)-3-fluoro-1H-pyrazol-4-yl)-3-(methyl-d3)-8-(1-(methyl-d3)-1H-indazol-5-yl)-2-oxo-3,6-dihydroimidazo[4,5-d]pyrrolo[2,3-b]pyridin-1(2H)-yl)cyclopentyl)carbamate;

methyl ((1R,3R)-3-(7-(3-fluoro-1-(methyl-d3)-1H-pyrazol-4-yl)-8-(1-isopropyl-1H-indazol-5-yl)-3-methyl-2-oxo-3,6-dihydroimidazo[4,5-d]pyrrolo[2,3-b]pyridin-1(2H)-yl)cyclopentyl)carbamate;

methyl ((1R,3R)-3-(8-(7-fluoro-1-(methyl-d3)-1H-indazol-5-yl)-7-(3-fluoro-1-(methyl-d3)-1H-pyrazol-4-yl)-3-(methyl-d3)-2-oxo-3,6-dihydroimidazo[4,5-d]pyrrolo[2,3-b]pyridin-1(2H)-yl)cyclopentyl)carbamate;

methyl ((1R,3R)-3-(8-(1-(2,2-difluoroethyl)-1H-indazol-5-yl)-7-(3-fluoro-1-(methyl-d3)-1H-pyrazol-4-yl)-3-methyl-2-oxo-3,6-dihydroimidazo[4,5-d]pyrrolo[2,3-b]pyridin-1(2H)-yl)cyclopentyl)carbamate;

methyl ((1R,3R)-3-(8-(1,1-dimethyl-1,3-dihydroisobenzofuran-5-yl)-7-(1-(ethyl-d5)-3-fluoro-1H-pyrazol-4-yl)-3-(methyl-d3)-2-oxo-3,6-dihydroimidazo[4,5-d]pyrrolo[2,3-b]pyridin-1(2H)-yl)cyclopentyl)carbamate;

methyl ((1R,3R)-3-(8-(1,1-dimethyl-1,3-dihydroisobenzofuran-5-yl)-7-(1-ethyl-3-fluoro-1H-pyrazol-4-yl)-3-(methyl-d3)-2-oxo-3,6-dihydroimidazo[4,5-d]pyrrolo[2,3-b]pyridin-1(2H)-yl)cyclopentyl)carbamate; and methyl ((1R,3R)-3-(7-(3-fluoro-1-(propan-2-yl-d7)-1H-pyrazol-4-yl)-3-(methyl-d3)-8-(1-(methyl-d3)-1H-indazol-5-yl)-2-oxo-3,6-dihydroimidazo[4,5-d]pyrrolo[2,3-b]pyridin-1(2H)-yl)cyclopentyl)carbamate;

or a pharmaceutically acceptable salt thereof.

In some embodiments, the compound of Formula I is selected from:

methyl ((1R,3R)-3-(8-(4-fluorophenyl)-7-(3-methoxy-1-methyl-1H-pyrazol-4-yl)-3-methyl-2-oxo-3,6-dihydroimidazo[4,5-d]pyrrolo[2,3-b]pyridin-1(2H)-yl)cyclopentyl)carbamate;

methyl ((1R,3R)-3-(7-(3-methoxy-1-methyl-1H-pyrazol-4-yl)-3-methyl-2-oxo-8-phenyl-3,6-dihydroimidazo[4,5-d]pyrrolo[2,3-b]pyridin-1(2H)-yl)cyclopentyl)carbamate;

methyl ((1R,3R)-3-(8-(3-fluorophenyl)-7-(3-methoxy-1-methyl-1H-pyrazol-4-yl)-3-methyl-2-oxo-3,6-dihydroimidazo[4,5-d]pyrrolo[2,3-b]pyridin-1(2H)-yl)cyclopentyl)carbamate;

methyl ((1R,3R)-3-(8-(3-fluoro-4-methoxyphenyl)-7-(3-methoxy-1-methyl-1H-pyrazol-4-yl)-3-methyl-2-oxo-3,6-dihydroimidazo[4,5-d]pyrrolo[2,3-b]pyridin-1(2H)-yl)cyclopentyl)carbamate; and methyl ((1R,3R)-3-(7-(3-methoxy-1-methyl-1H-pyrazol-4-yl)-3-methyl-8-(1-(methyl-d₃)-1H-indazol-5-yl)-2-oxo-3,6-dihydroimidazo[4,5-d]pyrrolo[2,3-b]pyridin-1(2H)-yl)cyclopentyl)carbamate;

or a pharmaceutically acceptable salt thereof.

In some embodiments, the compound of Formula I is selected from:

methyl ((1R,3R)-3-(7-(3-fluoro-1-(methyl-d₃)-1H-pyrazol-4-yl)-3-(methyl-d₃)-8-(1-(methyl-d₃)-1H-indazol-5-yl)-2-oxo-3,6-dihydroimidazo[4,5-d]pyrrolo[2,3-b]pyridin-1(2H)-yl)cyclopentyl)carbamate; and methyl ((1R,3R)-3-(7-(3-fluoro-1-(methyl-d₃)-1H-pyrazol-4-yl)-8-(4-fluorophenyl)-3-(methyl-d₃)-2-oxo-3,6-dihydroimidazo[4,5-d]pyrrolo[2,3-b]pyridin-1(2H)-yl)cyclopentyl)carbamate;

or a pharmaceutically acceptable salt thereof.

In some embodiments, the compound of Formula I is selected from:

methyl ((1R,3R)-3-(8-(1,1-dimethyl-1,3-dihydroisobenzofuran-5-yl)-7-(3-fluoro-1-(methyl-d3)-1H-pyrazol-4-yl)-3-(methyl-d3)-2-oxo-3,6-dihydroimidazo[4,5-d]pyrrolo[2,3-b]pyridin-1(2H)-yl)cyclopentyl)carbamate;

methyl ((1R,3R)-3-(7-(3-fluoro-1-(methyl-d3)-1H-pyrazol-4-yl)-8-(4-(methoxy-d3)phenyl)-3-(methyl-d3)-2-oxo-3,6-dihydroimidazo[4,5-d]pyrrolo[2,3-b]pyridin-1(2H)-yl)cyclopentyl)carbamate;

methyl ((1R,3R)-3-(7-(3-fluoro-1-(methyl-d3)-1H-pyrazol-4-yl)-8-(4-(2-hydroxypropan-2-yl)phenyl)-3-(methyl-d3)-2-oxo-3,6-dihydroimidazo[4,5-d]pyrrolo[2,3-b]pyridin-1(2H)-yl)cyclopentyl)carbamate;

methyl ((1R,3R)-3-(8-(1,1-dimethyl-1,3-dihydroisobenzofuran-5-yl)-7-(3-fluoro-1-(methyl-d3)-1H-pyrazol-4-yl)-3-methyl-2-oxo-3,6-dihydroimidazo[4,5-d]pyrrolo[2,3-b]pyridin-1(2H)-yl)cyclopentyl)carbamate;

methyl ((1R,3R)-3-(7-(1-(2,2-difluoroethyl)-3-fluoro-1H-pyrazol-4-yl)-8-(1,1-dimethyl-1,3-dihydroisobenzofuran-5-yl)-3-(methyl-d3)-2-oxo-3,6-dihydroimidazo[4,5-d]pyrrolo[2,3-b]pyridin-1(2H)-yl)cyclopentyl)carbamate;

methyl ((1R,3R)-3-(7-(3-fluoro-1-(methyl-d3)-1H-pyrazol-4-yl)-8-(1-isopropyl-1H-indazol-5-yl)-3-(methyl-d3)-2-oxo-3,6-dihydroimidazo[4,5-d]pyrrolo[2,3-b]pyridin-1(2H)-yl)cyclopentyl)carbamate;

methyl ((1R,3R)-3-(8-(1-(2,2-difluoroethyl)-1H-indazol-5-yl)-7-(3-fluoro-1-(methyl-d3)-1H-pyrazol-4-yl)-3-(methyl-d3)-2-oxo-3,6-dihydroimidazo[4,5-d]pyrrolo[2,3-b]pyridin-1(2H)-yl)cyclopentyl)carbamate;

methyl ((1R,3R)-3-(7-(1-(ethyl-d5)-3-fluoro-1H-pyrazol-4-yl)-3-(methyl-d3)-8-(1-(methyl-d3)-1H-indazol-5-yl)-2-oxo-3,6-dihydroimidazo[4,5-d]pyrrolo[2,3-b]pyridin-1(2H)-yl)cyclopentyl)carbamate;

methyl ((1R,3R)-3-(7-(3-fluoro-1-(methyl-d3)-1H-pyrazol-4-yl)-8-(1-isopropyl-1H-indazol-5-yl)-3-methyl-2-oxo-3,6-dihydroimidazo[4,5-d]pyrrolo[2,3-b]pyridin-1(2H)-yl)cyclopentyl)carbamate;
methyl ((1R,3R)-3-(8-(7-fluoro-1-(methyl-d3)-1H-indazol-5-yl)-7-(3-fluoro-1-(methyl-d3)-1H-pyrazol-4-yl)-3-(methyl-d3)-2-oxo-3,6-dihydroimidazo[4,5-d]pyrrolo[2,3-b]pyridin-1(2H)-yl)cyclopentyl)carbamate;
methyl ((1R,3R)-3-(8-(1-(2,2-difluoroethyl)-1H-indazol-5-yl)-7-(3-fluoro-1-(methyl-d3)-1H-pyrazol-4-yl)-3-methyl-2-oxo-3,6-dihydroimidazo[4,5-d]pyrrolo[2,3-b]pyridin-1(2H)-yl)cyclopentyl)carbamate;
methyl ((1R,3R)-3-(8-(1,1-dimethyl-1,3-dihydroisobenzofuran-5-yl)-7-(1-(ethyl-d5)-3-fluoro-1H-pyrazol-4-yl)-3-(methyl-d3)-2-oxo-3,6-dihydroimidazo[4,5-d]pyrrolo[2,3-b]pyridin-1(2H)-yl)cyclopentyl)carbamate;
methyl ((1R,3R)-3-(8-(1,1-dimethyl-1,3-dihydroisobenzofuran-5-yl)-7-(1-ethyl-3-fluoro-1H-pyrazol-4-yl)-3-(methyl-d3)-2-oxo-3,6-dihydroimidazo[4,5-d]pyrrolo[2,3-b]pyridin-1(2H)-yl)cyclopentyl)carbamate; and
methyl ((1R,3R)-3-(7-(3-fluoro-1-(propan-2-yl-d7)-1H-pyrazol-4-yl)-3-(methyl-d3)-8-(1-(methyl-d3)-1H-indazol-5-yl)-2-oxo-3,6-dihydroimidazo[4,5-d]pyrrolo[2,3-b]pyridin-1(2H)-yl)cyclopentyl)carbamate;
or a pharmaceutically acceptable salt thereof.

In some embodiments, the compound of Formula I is methyl ((1R,3R)-3-(8-(4-fluorophenyl)-7-(3-methoxy-1-methyl-1H-pyrazol-4-yl)-3-methyl-2-oxo-3,6-dihydroimidazo[4,5-d]pyrrolo[2,3-b]pyridin-1(2H)-yl)cyclopentyl)carbamate, or a pharmaceutically acceptable salt thereof.

In some embodiments, the compound of Formula I is methyl ((1R,3R)-3-(7-(3-methoxy-1-methyl-1H-pyrazol-4-yl)-3-methyl-2-oxo-8-phenyl-3,6-dihydroimidazo[4,5-d]pyrrolo[2,3-b]pyridin-1(2H)-yl)cyclopentyl)carbamate, or a pharmaceutically acceptable salt thereof.

In some embodiments, the compound of Formula I is methyl ((1R,3R)-3-(8-(3-fluorophenyl)-7-(3-methoxy-1-methyl-1H-pyrazol-4-yl)-3-methyl-2-oxo-3,6-dihydroimidazo[4,5-d]pyrrolo[2,3-b]pyridin-1(2H)-yl)cyclopentyl)carbamate, or a pharmaceutically acceptable salt thereof.

In some embodiments, the compound of Formula I is methyl ((1R,3R)-3-(8-(3-fluoro-4-methoxyphenyl)-7-(3-methoxy-1-methyl-1H-pyrazol-4-yl)-3-methyl-2-oxo-3,6-dihydroimidazo[4,5-d]pyrrolo[2,3-b]pyridin-1(2H)-yl)cyclopentyl)carbamate, or a pharmaceutically acceptable salt thereof.

In some embodiments, the compound of Formula I is methyl ((1R,3R)-3-(7-(3-methoxy-1-methyl-1H-pyrazol-4-yl)-3-methyl-8-(1-(methyl-$d_3$)-1H-indazol-5-yl)-2-oxo-3,6-dihydroimidazo[4,5-d]pyrrolo[2,3-b]pyridin-1(2H)-yl)cyclopentyl)carbamate, or a pharmaceutically acceptable salt thereof.

In some embodiments, the compound of Formula I is methyl ((1R,3R)-3-(7-(3-fluoro-1-(methyl-$d_3$)-1H-pyrazol-4-yl)-3-(methyl-$d_3$)-8-(1-(methyl-$d_3$)-1H-indazol-5-yl)-2-oxo-3,6-dihydroimidazo[4,5-d]pyrrolo[2,3-b]pyridin-1(2H)-yl)cyclopentyl)carbamate, or a pharmaceutically acceptable salt thereof.

In some embodiments, the compound of Formula I is methyl ((1R,3R)-3-(7-(3-fluoro-1-(methyl-$d_3$)-1H-pyrazol-4-yl)-8-(4-fluorophenyl)-3-(methyl-$d_3$)-2-oxo-3,6-dihydroimidazo[4,5-d]pyrrolo[2,3-b]pyridin-1(2H)-yl)cyclopentyl)carbamate, or a pharmaceutically acceptable salt thereof.

In some embodiments, the compound of Formula I is methyl ((1R,3R)-3-(8-(1,1-dimethyl-1,3-dihydroisobenzofuran-5-yl)-7-(3-fluoro-1-(methyl-d3)-1H-pyrazol-4-yl)-3-(methyl-d3)-2-oxo-3,6-dihydroimidazo[4,5-d]pyrrolo[2,3-b]pyridin-1(2H)-yl)cyclopentyl)carbamate, or a pharmaceutically acceptable salt thereof.

In some embodiments, the compound of Formula I is methyl ((1R,3R)-3-(7-(3-fluoro-1-(methyl-d3)-1H-pyrazol-4-yl)-8-(4-(methoxy-d3)phenyl)-3-(methyl-d3)-2-oxo-3,6-dihydroimidazo[4,5-d]pyrrolo[2,3-b]pyridin-1(2H)-yl)cyclopentyl)carbamate, or a pharmaceutically acceptable salt thereof.

In some embodiments, the compound of Formula I is methyl ((1R,3R)-3-(7-(3-fluoro-1-(methyl-d3)-1H-pyrazol-4-yl)-8-(4-(2-hydroxypropan-2-yl)phenyl)-3-(methyl-d3)-2-oxo-3,6-dihydroimidazo[4,5-d]pyrrolo[2,3-b]pyridin-1(2H)-yl)cyclopentyl)carbamate, or a pharmaceutically acceptable salt thereof.

In some embodiments, the compound of Formula I is methyl ((1R,3R)-3-(8-(1,1-dimethyl-1,3-dihydroisobenzofuran-5-yl)-7-(3-fluoro-1-(methyl-d3)-1H-pyrazol-4-yl)-3-methyl-2-oxo-3,6-dihydroimidazo[4,5-d]pyrrolo[2,3-b]pyridin-1(2H)-yl)cyclopentyl)carbamate, or a pharmaceutically acceptable salt thereof.

In some embodiments, the compound of Formula I is methyl ((1R,3R)-3-(7-(1-(2,2-difluoroethyl)-3-fluoro-1H-pyrazol-4-yl)-8-(1,1-dimethyl-1,3-dihydroisobenzofuran-5-yl)-3-(methyl-d3)-2-oxo-3,6-dihydroimidazo[2,3-b]pyrrolo[2,3-b]pyridin-1(2H)-yl)cyclopentyl)carbamate, or a pharmaceutically acceptable salt thereof.

In some embodiments, the compound of Formula I is methyl ((1R,3R)-3-(7-(3-fluoro-1-(methyl-d3)-1H-pyrazol-4-yl)-8-(1-isopropyl-1H-indazol-5-yl)-3-(methyl-d3)-2-oxo-3,6-dihydroimidazo[4,5-d]pyrrolo[2,3-b]pyridin-1(2H)-yl)cyclopentyl)carbamate, or a pharmaceutically acceptable salt thereof.

In some embodiments, the compound of Formula I is methyl ((1R,3R)-3-(8-(1-(2,2-difluoroethyl)-1H-indazol-5-yl)-7-(3-fluoro-1-(methyl-d3)-1H-pyrazol-4-yl)-3-(methyl-d3)-2-oxo-3,6-dihydroimidazo[4,5-d]pyrrolo[2,3-b]pyridin-1(2H)-yl)cyclopentyl)carbamate, or a pharmaceutically acceptable salt thereof.

In some embodiments, the compound of Formula I is methyl ((1R,3R)-3-(7-(1-(ethyl-d5)-3-fluoro-1H-pyrazol-4-yl)-3-(methyl-d3)-8-(1-(methyl-d3)-1H-indazol-5-yl)-2-oxo-3,6-dihydroimidazo[4,5-d]pyrrolo[2,3-b]pyridin-1(2H)-yl)cyclopentyl)carbamate, or a pharmaceutically acceptable salt thereof.

In some embodiments, the compound of Formula I is methyl ((1R,3R)-3-(7-(3-fluoro-1-(methyl-d3)-1H-pyrazol-4-yl)-8-(1-isopropyl-1H-indazol-5-yl)-3-methyl-2-oxo-3,6-dihydroimidazo[4,5-d]pyrrolo[2,3-b]pyridin-1(2H)-yl)cyclopentyl)carbamate, or a pharmaceutically acceptable salt thereof.

In some embodiments, the compound of Formula I is methyl ((1R,3R)-3-(8-(7-fluoro-1-(methyl-d3)-1H-indazol-5-yl)-7-(3-fluoro-1-(methyl-d3)-1H-pyrazol-4-yl)-3-(methyl-d3)-2-oxo-3,6-dihydroimidazo[4,5-d]pyrrolo[2,3-b]pyridin-1(2H)-yl)cyclopentyl)carbamate, or a pharmaceutically acceptable salt thereof.

In some embodiments, the compound of Formula I is methyl ((1R,3R)-3-(8-(1-(2,2-difluoroethyl)-1H-indazol-5-yl)-7-(3-fluoro-1-(methyl-d3)-1H-pyrazol-4-yl)-3-methyl-2-oxo-3,6-dihydroimidazo[4,5-d]pyrrolo[2,3-b]pyridin-1(2H)-yl)cyclopentyl)carbamate, or a pharmaceutically acceptable salt thereof.

In some embodiments, the compound of Formula I is methyl ((1R,3R)-3-(8-(1,1-dimethyl-1,3-dihydroisobenzofuran-5-yl)-7-(1-(ethyl-d5)-3-fluoro-1H-pyrazol-4-yl)-3-(methyl-d3)-2-oxo-3,6-dihydroimidazo[4,5-d]pyrrolo[2,3- b]pyridin-1(2H)-yl)cyclopentyl)carbamate, or a pharmaceutically acceptable salt thereof.

In some embodiments, the compound of Formula I is methyl ((1R,3R)-3-(8-(1,1-dimethyl-1,3-dihydroisobenzofuran-5-yl)-7-(1-ethyl-3-fluoro-1H-pyrazol-4-yl)-3-(methyl-d3)-2-oxo-3,6-dihydroimidazo[4,5-d]pyrrolo[2,3-b]pyridin-1(2H)-yl)cyclopentyl)carbamate, or a pharmaceutically acceptable salt thereof.

In some embodiments, the compound of Formula I is methyl ((1R,3R)-3-(7-(3-fluoro-1-(propan-2-yl-d7)-1H-pyrazol-4-yl)-3-(methyl-d3)-8-(1-(methyl-d3)-1H-indazol-5-yl)-2-oxo-3,6-dihydroimidazo[4,5-d]pyrrolo[2,3-b]pyridin-1(2H)-yl)cyclopentyl)carbamate, or a pharmaceutically acceptable salt thereof.

It is further appreciated that certain features of the invention, which are, for clarity, described in the context of separate embodiments, can also be provided in combination in a single embodiment. Conversely, various features of the invention which are, for brevity, described in the context of a single embodiment, can also be provided separately or in any suitable subcombination.

At various places in the present specification, divalent linking substituents are described. It is specifically intended that each divalent linking substituent include both the forward and backward forms of the linking substituent. For example, —NR(CR'R")$_n$— includes both —NR(CR'R")$_n$— and —(CR'R")$_n$NR—. Where the structure clearly requires a linking group, the Markush variables listed for that group are understood to be linking groups.

The term "n-membered" where n is an integer typically describes the number of ring-forming atoms in a moiety where the number of ring-forming atoms is n. For example, piperidinyl is an example of a 6-membered heterocycloalkyl ring, pyrazolyl is an example of a 5-membered heteroaryl ring, pyridyl is an example of a 6-membered heteroaryl ring, and 1,2,3,4-tetrahydro-naphthalene is an example of a 10-membered cycloalkyl group.

As used herein, the phrase "optionally substituted" means unsubstituted or substituted. The substituents are independently selected, and substitution may be at any chemically accessible position. As used herein, the term "substituted" means that a hydrogen atom is removed and replaced by a substituent. A single divalent substituent, e.g., oxo, can replace two hydrogen atoms. It is to be understood that substitution at a given atom is limited by valency.

As used herein, the phrase "each 'variable' is independently selected from" means substantially the same as wherein "at each occurrence 'variable' is selected from."

Throughout the definitions, the term "Cn-m" indicates a range which includes the endpoints, wherein n and m are integers and indicate the number of carbons. Examples include $C_{1-3}$, $C_{1-4}$, $C_{1-5}$, $C_{1-6}$, and the like.

As used herein, the term "Cn-m alkyl", employed alone or in combination with other terms, refers to a saturated hydrocarbon group that may be straight-chain or branched, having n to m carbons. Examples of alkyl moieties include, but are not limited to, chemical groups such as methyl (Me), ethyl (Et), n-propyl (n-Pr), isopropyl (iPr), n-butyl, tert-butyl, isobutyl, sec-butyl; higher homologs such as 2-methyl-1-butyl, n-pentyl, 3-pentyl, n-hexyl, 1,2,2-trimethylpropyl, and the like. In some embodiments, the alkyl group contains from 1 to 6 carbon atoms, from 1 to 5 carbon atoms, from 1 to 4 carbon atoms, from 1 to 3 carbon atoms, or 1 to 2 carbon atoms.

As used herein, the term "Cn-m alkoxy", employed alone or in combination with other terms, refers to a group of formula —O-alkyl, wherein the alkyl group has n to m carbons. Example alkoxy groups include, but are not limited to, methoxy, ethoxy, propoxy (e.g., n-propoxy and isopropoxy), butoxy (e.g., n-butoxy and tert-butoxy), and the like. In some embodiments, the alkyl group has 1 to 6, 1 to 5, 1 to 4, or 1 to 3 carbon atoms.

As used herein, the term "Cn-m hydroxyalkyl", employed alone or in combination with other terms, refers to an alkyl group having from one hydroxy (OH) group to 2s+1 hydroxy groups, where "s" is the number of carbon atoms in the alkyl group, wherein the alkyl group has n to m carbon atoms. In some embodiments, the hydroxyalkyl comprises one hydroxy group. In some embodiments, the alkyl group has 1 to 6, 1 to 4, or 1 to 3 carbon atoms. Example hydroxyalkyl groups include, but are not limited to, hydroxymethyl (—CH$_2$OH), hydroxyethyl (e.g., —CH$_2$CH$_2$OH and —CH(OH)CH$_3$), 1-hydroxyethyl, 2-hydroxyethyl, hydroxypropyl, 1-hydroxypropan-1-yl, 1-hydroxypropan-2-yl, 2-hydroxypropan-2-yl, and the like.

As used herein, "halo" refers to fluoro, chloro, bromo, or iodo. In some embodiments, a halo is fluoro.

At certain places, the definitions or embodiments refer to specific rings (e.g., a phenyl ring, an indazolyl ring, etc.). Unless otherwise indicated, these rings can be attached to any ring member provided that the valency of the atom is not exceeded. For example, an indazolyl ring may be attached at any position of the ring, whereas an indazol-5-yl ring is attached at the 5-position.

As used herein, the term "independently selected from" means that each occurrence of a variable or substituent are independently selected at each occurrence from the applicable list.

The compounds described herein can be asymmetric (e.g., having one or more stereocenters). All stereoisomers, such as enantiomers and diastereomers, are intended unless otherwise indicated. Compounds of the present disclosure that contain asymmetrically substituted carbon atoms can be isolated in optically active or racemic forms. Methods on how to prepare optically active forms from optically inactive starting materials are known in the art, such as by resolution of racemic mixtures or by stereoselective synthesis. Many geometric isomers of olefins, C=N double bonds, and the like can also be present in the compounds described herein, and all such stable isomers are contemplated in the present invention. Cis and trans geometric isomers of the compounds of the present disclosure are described and may be isolated as a mixture of isomers or as separated isomeric forms. In some embodiments, the compound has the (R)-configuration. In some embodiments, the compound has the (S)-configuration. The Formulas (e.g., Formula I, Formula Ia, etc.) provided herein include stereoisomers of the compounds.

Resolution of racemic mixtures of compounds can be carried out by any of numerous methods known in the art. An example method includes fractional recrystallizaion using a chiral resolving acid which is an optically active, salt-forming organic acid. Suitable resolving agents for fractional recrystallization methods are, for example, optically active acids, such as the D and L forms of tartaric acid, diacetyltartaric acid, dibenzoyltartaric acid, mandelic acid, malic acid, lactic acid or the various optically active camphorsulfonic acids such as 0-camphorsulfonic acid. Other resolving agents suitable for fractional crystallization methods include stereoisomerically pure forms of α-methylbenzylamine (e.g., S and R forms, or diastereomerically pure forms), 2-phenylglycinol, norephedrine, ephedrine, N-methylephedrine, cyclohexylethylamine, 1,2-diaminocyclohexane, and the like.

Resolution of racemic mixtures can also be carried out by elution on a column packed with an optically active resolving agent (e.g., dinitrobenzoylphenylglycine). Suitable elution solvent composition can be determined by one skilled in the art.

Compounds provided herein also include tautomeric forms. Tautomeric forms result from the swapping of a single bond with an adjacent double bond together with the concomitant migration of a proton. Tautomeric forms include prototropic tautomers which are isomeric protonation states having the same empirical formula and total charge. Example prototropic tautomers include ketone-enol pairs, amide-imidic acid pairs, lactam-lactim pairs, enamine-imine pairs, and annular forms where a proton can occupy two or more positions of a heterocyclic system, for example, 1H- and 3H-imidazole, 1H-, 2H- and 4H-1,2,4-triazole, 1H- and 2H-isoindole, 2-hydroxypyridine and 2-pyridone, and 1H- and 2H-pyrazole. Tautomeric forms can be in equilibrium or sterically locked into one form by appropriate substitution.

All compounds, and pharmaceutically acceptable salts thereof, can be found together with other substances such as water and solvents (e.g., hydrates and solvates) or can be isolated.

In some embodiments, preparation of compounds can involve the addition of acids or bases to affect, for example, catalysis of a desired reaction or formation of salt forms such as acid addition salts.

In some embodiments, the compounds provided herein, or salts thereof, are substantially isolated. By "substantially isolated" is meant that the compound is at least partially or substantially separated from the environment in which it was formed or detected. Partial separation can include, for example, a composition enriched in the compounds provided herein. Substantial separation can include compositions containing at least about 50%, at least about 60%, at least about 70%, at least about 80%, at least about 90%, at least about 95%, at least about 97%, or at least about 99% by weight of the compounds provided herein, or salt thereof.

The term "compound" as used herein is meant to include all stereoisomers, geometric isomers, tautomers, and isotopes of the structures depicted. Compounds herein identified by name or structure as one particular tautomeric form are intended to include other tautomeric forms unless otherwise specified.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The present application also includes pharmaceutically acceptable salts of the compounds described herein. As used herein, "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present disclosure include the conventional non-toxic salts of the parent compound formed, for example, from non-toxic inorganic or organic acids. The pharmaceutically acceptable salts of the present disclosure can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, alcohols (e.g., methanol, ethanol, iso-propanol, or butanol) or acetonitrile (i.e., ACN or AcCN) are preferred. Lists of suitable salts are found in *Remington's Pharmaceutical Sciences,* 17th ed., Mack Publishing Company, Easton, Pa., 1985, p. 1418 and *Journal of Pharmaceutical Science,* 66, 2 (1977), each of which is incorporated herein by reference in its entirety.

Synthesis

As will be appreciated by those skilled in the art, the compounds provided herein, including salts and stereoisomers thereof, can be prepared using known organic synthesis techniques and can be synthesized according to any of numerous possible synthetic routes.

Compounds of Formula I can be prepared, for example, as shown in Scheme 1. Optionally protected (e.g., P=phenylsulfonyl) nitrobicyclic heterocycles 1-1 where $X^1$ is halogen (e.g., Cl, Br, or I) or pseudohalogen (e.g., OTf or OMs) can be coupled with amines such as 1-2 under standard $S_NAr$ conditions (e.g., in the presence of a base such as $Et_3N$) to give 1-3. Nitroheterocycle 1-3 can be reduced under standard conditions (e.g., in the presence of Fe and acid) to give 1-4. Diamine 1-4 can be converted to cyclic urea 1-5 under standard conditions (e.g., in the presence of CDI). Cyclic urea 1-5 can be alkylated under standard $S_N2$ conditions (e.g., in the presence of $K_2CO_3$ and $R^4$—$X^2$, where $X^2$ is a halogen (e.g., Cl, Br, or I) or pseudohalogen (e.g., OTf or OMs)) to give 1-6. Cyclic urea 1-6 can be converted to halide 1-7, where $X^3$ is a halogen (e.g., Cl, Br, or I), under standard conditions (e.g., in the presence of LDA or alkyllithium, 1,2-dibromotetrachloroethane in the case of bromination). Halide 1-7 can be coupled with 1-8, where $M^1$ is a boronic acid, boronate ester, potassium trifluoroborate, or an appropriately substituted metal such as $Sn(Bu)_3$ or Zn, under standard Suzuki conditions (e.g., in the presence of a palladium catalyst, such as tetrakis(triphenylphosphine)palladium(0) and a base (e.g., a carbonate base)) or standard Stille conditions (e.g., in the presence of a palladium(0) catalyst, such as tetrakis(triphenylphosphine)palladium(0)) or standard Negishi conditions (e.g., in the presence of a palladium catalyst, such as tetrakis(triphenylphosphine)palladium(0) or [1,1'-bis(diphenylphosphino)ferrocene]dichloropalladium (II)), to give compound 1-9. Compound 1-9 can be brominated with a suitable reagent such as bromine to give 1-10. The Boc group in compound 1-10 can be removed under standard conditions (e.g., TFA in $CH_2Cl_2$) to give amine 1-11. Amine 1-11 can be converted to carbamate 1-12 under standard conditions (e.g., methyl chloroformate). Compound 1-12 can be coupled with $R^1$-$M^2$, where $M^2$ is a boronic acid, boronate ester, potassium trifluoroborate, or an appropriately substituted metal such as $Sn(Bu)_3$ or Zn, under standard Suzuki conditions (e.g., in the presence of a palladium catalyst, such as tetrakis(triphenylphosphine)palladium(0) and a base (e.g., a carbonate base)) or standard Stille conditions (e.g., in the presence of a palladium(0) catalyst, such as tetrakis(triphenylphosphine)palladium(0)) or standard Negishi conditions (e.g., in the presence of a palladium catalyst, such as tetrakis(triphenylphosphine)palladium(0) or [1,1'-bis(diphenylphosphino)ferrocene]dichloropalladium (II)), to give compound 1-13. Compound 1-13 can be deprotected under standard conditions (e.g., NaOH when P=phenylsulfonyl) to give compounds of Formula I.

Scheme 1.
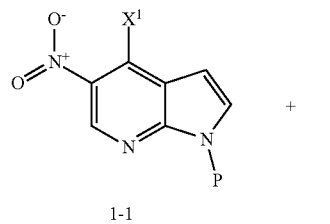
1-1
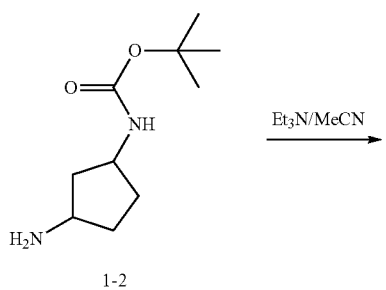
1-2
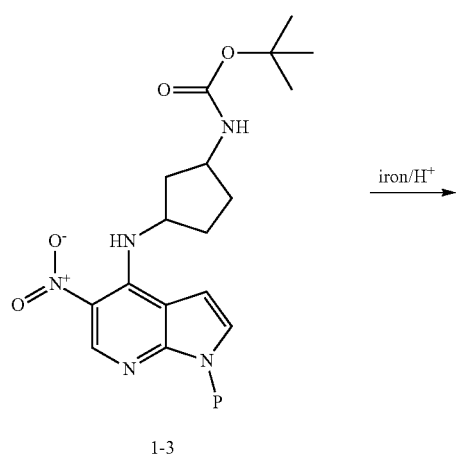
1-3
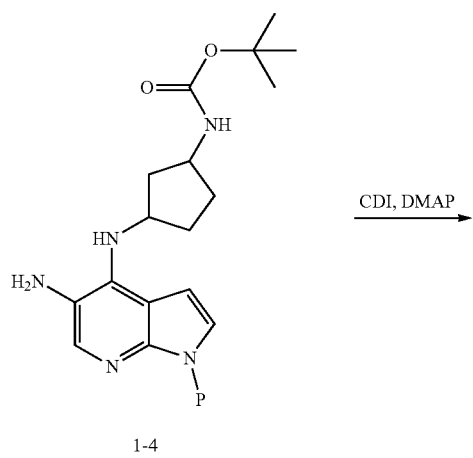
1-4
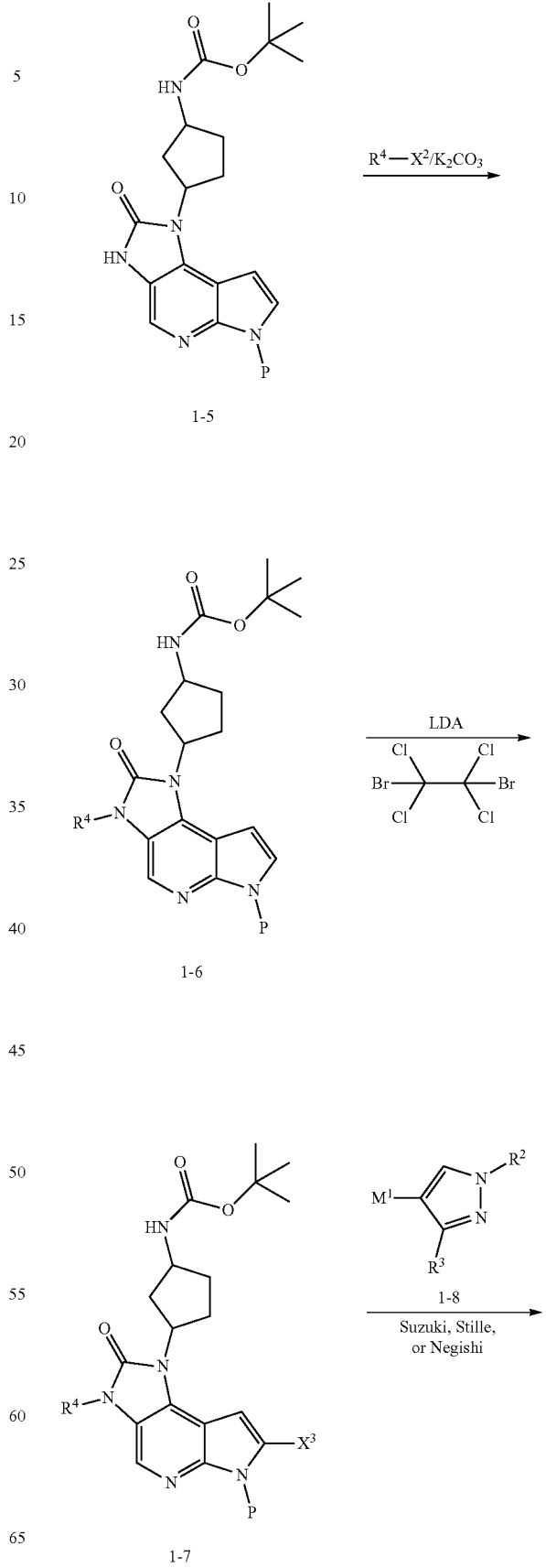

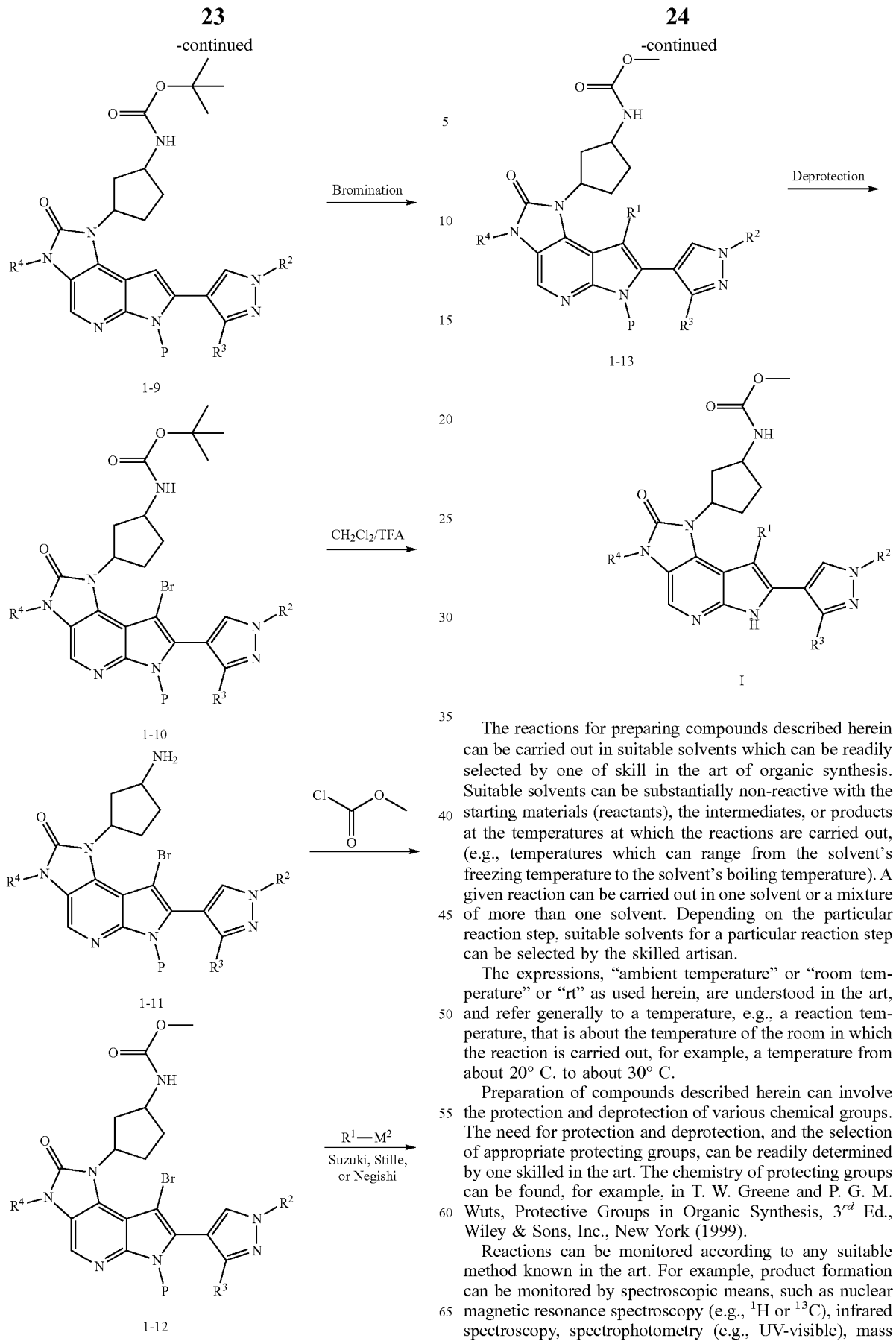

The reactions for preparing compounds described herein can be carried out in suitable solvents which can be readily selected by one of skill in the art of organic synthesis. Suitable solvents can be substantially non-reactive with the starting materials (reactants), the intermediates, or products at the temperatures at which the reactions are carried out, (e.g., temperatures which can range from the solvent's freezing temperature to the solvent's boiling temperature). A given reaction can be carried out in one solvent or a mixture of more than one solvent. Depending on the particular reaction step, suitable solvents for a particular reaction step can be selected by the skilled artisan.

The expressions, "ambient temperature" or "room temperature" or "rt" as used herein, are understood in the art, and refer generally to a temperature, e.g., a reaction temperature, that is about the temperature of the room in which the reaction is carried out, for example, a temperature from about 20° C. to about 30° C.

Preparation of compounds described herein can involve the protection and deprotection of various chemical groups. The need for protection and deprotection, and the selection of appropriate protecting groups, can be readily determined by one skilled in the art. The chemistry of protecting groups can be found, for example, in T. W. Greene and P. G. M. Wuts, Protective Groups in Organic Synthesis, 3$^{rd}$ Ed., Wiley & Sons, Inc., New York (1999).

Reactions can be monitored according to any suitable method known in the art. For example, product formation can be monitored by spectroscopic means, such as nuclear magnetic resonance spectroscopy (e.g., $^1$H or $^{13}$C), infrared spectroscopy, spectrophotometry (e.g., UV-visible), mass spectrometry, or by chromatographic methods such as high performance liquid chromatography (HPLC), liquid chromatography-mass spectroscopy (LCMS), or thin layer chromatography (TLC). Compounds can be purified by those skilled in the art by a variety of methods, including high performance liquid chromatography (HPLC) and normal phase silica chromatography.

Methods of Use

The compounds described herein can inhibit the activity of the V617F variant of the protein-tyrosine kinase JAK2 (i.e., "V617F" or "JAK2V617F"). Compounds which inhibit V617F are useful in providing a means of preventing the growth or inducing apoptosis in tumors, particularly by inhibiting angiogenesis. It is therefore anticipated that the compounds of the disclosure are useful in treating or preventing proliferative disorders such as cancers. In particular tumors with activating mutants of receptor tyrosine kinases or upregulation of receptor tyrosine kinases may be particularly sensitive to the inhibitors.

As disclosed herein, the compounds of the invention exhibit unexpectedly improved properties (e.g., improved potency and PK properties) compared to compounds disclosed in International Publication No.: WO 2022/006457, the disclosure of which is incorporated herein by reference in its entirety. The following compounds from WO 2022/006457 are provided herein as Comparative Examples A-E:

| Comparative Example | Structure |
|---|---|
| Comparative Example A | 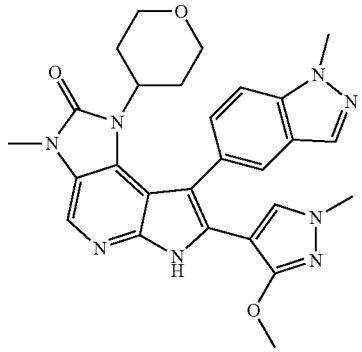 |
| Comparative Example B | 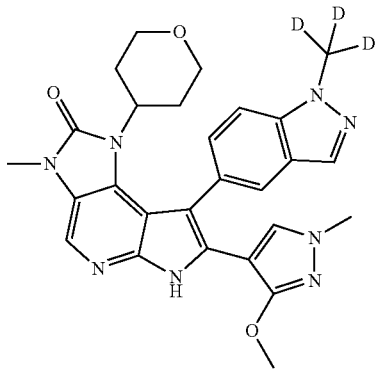 [SMILES: [2H]C([2H])([2H])n1ncc2cc(-c3c(-c4cn(C)nc4OC)[nH]c4ncc5c(c34)n(C3CCOCC3)c(=O)n5C)ccc21] |
| Comparative Example C | 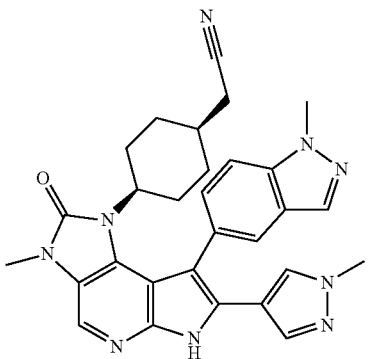 |
| Comparative Example D | 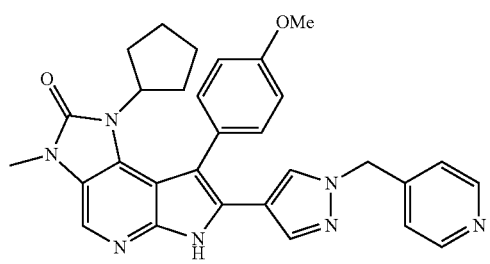 [SMILES: COc1ccc(-c2c(-c3cnn(Cc4ccncc4)c3)[nH]c3ncc4c(c23)n(C2CCCC2)c(=O)n4C)cc1] |
| Comparative Example E | 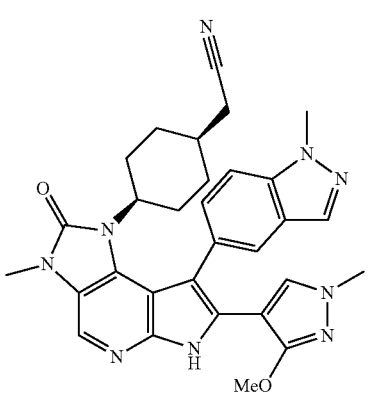 |

In certain embodiments, the present disclosure provides a method for treating a V617F-related disorder in a patient in need thereof, comprising the step of administering to said patient a compound of the disclosure, or a pharmaceutically acceptable composition thereof.

Myeloproliferative diseases (MPD) are multipotent hematopoietic stem cell disorders characterized by excess production of various blood cells. MPNs include polycythemia vera (PV), essential thrombocythemia (ET), and idiopathic myelofibrosis (IMF). JAK2 V617F mutation is reported in about 95% of patients with PV, in 35% to 70% of patients with ET, and 50% of patients with IMF. Also, JAK2 exon 12 mutations are detected in some of the V617F-negative PV patients (Ma et al., J. Mol. Diagn., 11: 49-53, 2009). In some embodiments, the compounds of the disclosure can be useful in the treatment of myeloproliferative disorders (e.g., myeloproliferative neoplasms) in a patient in need thereof, such as polycythemia vera, essential thrombocythemia, myelofibrosis with myeloid metaplasia (IMMM), primary myelofibrosis (PMF), chronic myelogenous leukemia (CML), chronic myelomonocytic leukemia (CMML), hypereosinophilic syndrome (HES), systemic mast cell disease (SMCD), and the like.

In some embodiments, the myeloproliferative disorder is a myeloproliferative neoplasm.

In some embodiments, the myeloproliferative disorder is myelofibrosis (e.g., primary myelofibrosis (PMF) or post polycythemia vera/essential thrombocythemia myelofibrosis (Post-PV/ET MF)).

In some embodiments, the myeloproliferative disorder is primary myelofibrosis (PMF).

In some embodiments, the myeloproliferative disorder is post-essential thrombocythemia myelofibrosis (Post-ET MF).

In some embodiments, the myeloproliferative disorder is post polycythemia vera myelofibrosis (Post-PV MF).

In some embodiments, the myeloproliferative disorder is selected from primary myelofibrosis (PMF), polycythemia vera (PV), and essential thrombocythemia (ET).

In some embodiments, the myeloproliferative neoplasm is primary myelofibrosis (PMF).

In some embodiments, the myeloproliferative neoplasm is polycythemia vera (PV).

In some embodiments, the myeloproliferative neoplasm is essential thrombocythemia (ET).

Myeloproliferative diseases include disorders of a bone marrow or lymph node-derived cell type, such as a white blood cell. A myeloproliferative disease can manifest by abnormal cell division resulting in an abnormal level of a particular hematological cell population. The abnormal cell division underlying a proliferative hematological disorder is typically inherent in the cells and not a normal physiological response to infection or inflammation. Leukemia is a type of myeloproliferative disease. Exemplary myeloproliferative diseases include, but are not limited to, acute myeloid leukemia (AML), acute lymphoblastic leukemia (ALL), chronic lymphocytic leukemia (CLL), myelodysplastic syndrome (MDS), chronic myeloid leukemia (CML), hairy cell leukemia, leukemic manifestations of lymphomas, multiple myeloma, polycythemia vera (PV), essential thrombocythemia (ET), idiopathic myelofibrosis (IMF), hypereosinophilic syndrome (HES), chronic neutrophilic leukemia (CNL), myelofibrosis with myeloid metaplasia (MMM), chronic myelomonocytic leukemia (CMML), juvenile myelomonocytic leukemia, chronic basophilic leukemia, chronic eosinophilic leukemia, systemic mastocytosis (SM), and unclassified myeloproliferative diseases (UMPD or MPD-NC). Lymphoma is a type of proliferative disease that mainly involves lymphoid organs, such as lymph nodes, liver, and spleen. Exemplary proliferative lymphoid disorders include lymphocytic lymphoma (also called chronic lymphocytic leukemia), follicular lymphoma, large cell lymphoma, Burkitt's lymphoma, marginal zone lymphoma, lymphoblastic lymphoma (also called acute lymphoblastic lymphoma).

For example, the compounds of the disclosure are useful in the treatment of cancer. Example cancers include bladder cancer (e.g., urothelial carcinoma, squamous cell carcinoma, adenocarcinoma), breast cancer (e.g., hormone R positive, triple negative), cervical cancer, colorectal cancer, cancer of the small intestine, colon cancer, rectal cancer, cancer of the anus, endometrial cancer, gastric cancer (e.g., gastrointestinal stromal tumors), head and neck cancer (e.g., cancers of the larynx, hypopharynx, nasopharynx, oropharynx, lips, and mouth, squamous head and neck cancers), kidney cancer (e.g., renal cell carcinoma, urothelial carcinoma, sarcoma, Wilms tumor), liver cancer (e.g., hepatocellular carcinoma, cholangiocellular carcinoma (e.g., intrahepatic, hilar or peri-hilar, distal extrahepatic), liver angiosarcoma, hepatoblastoma), lung cancer (e.g., adenocarcinoma, small cell lung cancer and non-small cell lung carcinomas, parvicellular and non-parvicellular carcinoma, bronchial carcinoma, bronchial adenoma, pleuropulmonary blastoma), ovarian cancer, prostate cancer, testicular cancer, uterine cancer, vulvar cancer, esophageal cancer, gall bladder cancer, pancreatic cancer (e.g. exocrine pancreatic carcinoma), stomach cancer, thyroid cancer, parathyroid cancer, neuroendocrine cancer (e.g., pheochromocytoma, Merkel cell cancer, neuroendocrine carcinoma), skin cancer (e.g., squamous cell carcinoma, Kaposi sarcoma, Merkel cell skin cancer), and brain cancer (e.g., astrocytoma, medulloblastoma, ependymoma, neuro-ectodermal tumors, pineal tumors).

Further example cancers include hematopoietic malignancies such as leukemia or lymphoma, multiple myeloma, chronic lymphocytic lymphoma, adult T cell leukemia, acute myeloid leukemia (AML), B-cell lymphoma, cutaneous T-cell lymphoma, acute myelogenous leukemia, Hodgkin's or non-Hodgkin's lymphoma, myeloproliferative neoplasms (e.g., 8p11 myeloproliferative syndrome, polycythemia vera (PV), essential thrombocythemia (ET), and primary myelofibrosis (PMF)), myelodysplastic syndrome, chronic eosinophilic leukemia, Waldenstrom's Macroglubulinemia, hairy cell lymphoma, chronic myelogenic lymphoma, acute lymphoblastic lymphoma, AIDS-related lymphomas, and Burkitt's lymphoma.

In certain embodiments, provided herein is a method of treating cancer comprising administering to a patient in need thereof a therapeutically effect amount of a compound of the disclosure. In certain embodiments, the cancer is selected from T lymphoblastic lymphoma, glioblastoma, melanoma, rhabdosarcoma, lymphosarcoma, and osteosarcoma.

Other cancers treatable with the compounds of the disclosure include tumors of the eye, glioblastoma, melanoma, leiomyosarcoma, and urothelial carcinoma (e.g., ureter, urethra, bladder, urachus).

The compounds of the disclosure can also be useful in the inhibition of tumor metastases.

In some embodiments, the compounds of the disclosure as described herein can be used to treat Alzheimer's disease, HIV, or tuberculosis.

In some embodiments, the compounds of the disclosure can be useful in the treatment of myelodysplastic syndrome (MDS) in a patient in need thereof. In some embodiments, said patient having the myelodysplastic syndrome (MDS) is red blood cell transfusion dependent.

As used herein, myelodysplastic syndromes are intended to encompass heterogeneous and clonal hematopoietic disorders that are characterized by ineffective hematopoiesis on one or more of the major myeloid cell lineages. Myelodysplastic syndromes are associated with bone marrow failure, peripheral blood cytopenias, and a propensity to progress to acute myeloid leukemia (AML). Moreover, clonal cytogenetic abnormalities can be detected in about 50% of cases with MDS. In 1997, The World Health Organization (WHO) in conjunction with the Society for Hematopathology (SH) and the European Association of Hematopathology (EAHP) proposed new classifications for hematopoietic neoplasms (Harris, et al., *J Clin Oncol* 1999; 17:3835-3849; Vardiman, et al., *Blood* 2002; 100:2292-2302). For MDS, the WHO utilized not only the morphologic criteria from the French-American-British (FAB) classification but also incorporated available genetic, biologic, and clinical characteristics to define subsets of MDS (Bennett, et al., *Br. J. Haematol.* 1982; 51:189-199). In 2008, the WHO classification of MDS (Table 1) was further refined to allow precise and prognostically relevant subclassification of unilineage dysplasia by incorporating new clinical and scientific information (Vardiman, et al., *Blood* 2009; 114:937-951; Swerdlow, et al., *WHO Classification of Tumours of Haematopoietic and Lymphoid Tissues*. 4th Edition. Lyon France: IARC Press; 2008:88-103; Bunning and Germing, "Myelodysplastic syndromes/neoplasms" in Chapter 5, Swerdlow, et al, eds. *WHO Classification of Tumours of Haematopoietic and Lymphoid Tissues*. (ed. 4th edition): Lyon, France: IARC Press; 2008: 88-103).

TABLE 1

2008 WHO Classification for De Novo Myelodysplastic Syndrome

| Subtype | Blood | Bone Marrow |
|---|---|---|
| Refractory cytopenia with unilineage dysplasia (RCUD) | Single or Bicytopenia | Dysplasia in ≥10% of 1 cell line, <5% blasts |
| Refractory anemia with ring sideroblasts (RARS) | Anemia, no blasts | ≥15% of erythroid precursors w/ring sideroblasts, erythroid dysplasia only, <5% blasts |
| Refractory cytopenia with multilineage dysplasia | Cytopenia(s), <1 × 10$^9$/L monocytes | Dysplasia in ≥10% of cells in ≥2 hematopoietic lineages, ±15% ring sideroblasts, <5% blasts |
| Refractory anemia with excess blasts-1 (RAEB-1) | Cytopenia(s), ≤2% to 4% blasts, <1 × 10$^9$/L monocytes | Unilineage or multilineage dysplasia, No Auer rods, 5% to 9% blasts |
| Refractory anemia with excess blasts-2 (RAEB-2) | Cytopenia(s), ≤5% to 19% blasts, <1 × 10$^9$/L monocytes | Unilineage or multilineage dysplasia, ±Auer rods, 10% to 19% blasts |
| Myelodysplastic syndrome, unclassified (MDS-U) | Cytopenias | Unilineage or no dysplasia but characteristic MDS cytogenetics, <5% blasts |
| MDS associated with isolated del(5q) | Anemia, platelets normal or increased | Unilineage erythroid. Isolated del(5q), <5% blasts |

In some embodiments, the myelodysplastic syndrome is refractory cytopenia with unilineage dysplasia (RCUD).

In some embodiments, the myelodysplastic syndrome is refractory anemia with ring sideroblasts (RARS).

In some embodiments, the myelodysplastic syndrome is refractory anemia with ring sideroblasts associated with thrombocytosis (RARS-T).

In some embodiments, the myelodysplastic syndrome is refractory cytopenia with multilineage dysplasia.

In some embodiments, the myelodysplastic syndrome is refractory anemia with excess blasts-1 (RAEB-1).

In some embodiments, the myelodysplastic syndrome is refractory anemia with excess blasts-2 (RAEB-2).

In some embodiments, the myelodysplastic syndrome is myelodysplastic syndrome, unclassified (MDS-U).

In some embodiments, the myelodysplastic syndrome is myelodysplastic syndrome associated with isolated del(5q).

In some embodiments, the myelodysplastic syndrome is refractory to erythropoiesis-stimulating agents.

In some embodiments, the compounds of the disclosure can be useful in the treatment of myeloproliferative disorder/myelodysplastic overlap syndrome (MPD/MDS overlap syndrome).

In some embodiments, the compounds of the disclosure can be useful in the treatment of leukemia.

In some embodiments, the compounds of the disclosure can be useful in the treatment of acute myeloid leukemia (AML).

In addition to oncogenic neoplasms, the compounds of the disclosure can be useful in the treatment of skeletal and chondrocyte disorders including, but not limited to, achrondroplasia, hypochondroplasia, dwarfism, thanatophoric dysplasia (TD) (clinical forms TD I and TD II), Apert syndrome, Crouzon syndrome, Jackson-Weiss syndrome, Beare-Stevenson cutis gyrate syndrome, Pfeiffer syndrome, and craniosynostosis syndromes.

The compounds provided herein may further be useful in the treatment of fibrotic diseases, such as where a disease symptom or disorder is characterized by fibrosis. Example fibrotic diseases include liver cirrhosis, glomerulonephritis, pulmonary fibrosis, systemic fibrosis, rheumatoid arthritis, and wound healing.

In some embodiments, the compounds provided herein can be used in the treatment of a hypophosphatemia disorder such as, for example, X-linked hypophosphatemic rickets, autosomal recessive hypophosphatemic rickets, and autosomal dominant hypophosphatemic rickets, or tumor-induced osteromalacia.

In some embodiments, provided herein is a method of increasing survival or progression-free survival in a patient, comprising administering a compound provided herein to the patient. In some embodiments, the patient has cancer. In some embodiments, the patient has a disease or disorder described herein. As used herein, progression-free survival refers to the length of time during and after the treatment of a solid tumor that a patient lives with the disease but it does not get worse. Progression-free survival can refer to the length of time from first administering the compound until the earlier of death or progression of the disease. Progression of the disease can be defined by RECIST v. 1.1 (Response Evaluation Criteria in Solid Tumors), as assessed by an independent centralized radiological review committee. In some embodiments, administering of the compound results in a progression free survival that is greater than about 1 month, about 2 months, about 3 months, about 4 months, about 5 months, about 6 months, about 8 months, about 9 months, about 12 months, about 16 months, or about 24 months. In some embodiments, the administering of the compound results in a progression free survival that is at least about 1 month, about 2 months, about 3 months, about 4 months, about 5 months, about 6 months, about 8 months, about 9 months, or about 12 months; and less than about 24 months, about 16 months, about 12 months, about 9 months, about 8 months, about 6 months, about 5 months, about 4 months, about 3 months, or about 2 months. In some embodiments, the administering of the compound results in an increase of progression free survival that is at least about 1 month, about 2 months, about 3 months, about 4 months, about 5 months, about 6 months, about 8 months, about 9 months, or about 12 months; and less than about 24 months, about 16 months, about 12 months, about 9 months, about 8 months, about 6 months, about 5 months, about 4 months, about 3 months, or about 2 months.

The present disclosure further provides a compound described herein, or a pharmaceutically acceptable salt thereof, for use in any of the methods described herein.

The present disclosure further provides use of a compound described herein, or a pharmaceutically acceptable salt thereof, for the preparation of a medicament for use in any of the methods described herein.

As used herein, the term "cell" is meant to refer to a cell that is in vitro, ex vivo or in vivo. In some embodiments, an ex vivo cell can be part of a tissue sample excised from an organism such as a mammal. In some embodiments, an in vitro cell can be a cell in a cell culture. In some embodiments, an in vivo cell is a cell living in an organism such as a mammal.

As used herein, the term "contacting" refers to the bringing together of indicated moieties in an in vitro system or an in vivo system. For example, "contacting" a V617F variant with a compound described herein includes the administration of a compound described herein to an individual or patient, such as a human, having a V617F variant, as well as, for example, introducing a compound described herein into a sample containing a cellular or purified preparation containing the V617F variant.

As used herein, the term "individual" or "patient," used interchangeably, refers to any animal, including mammals, preferably mice, rats, other rodents, rabbits, dogs, cats, swine, cattle, sheep, horses, or primates, and most preferably humans.

As used herein, the phrase "therapeutically effective amount" refers to the amount of active compound or pharmaceutical agent such as an amount of any of the solid forms or salts thereof as disclosed herein that elicits the biological or medicinal response in a tissue, system, animal, individual or human that is being sought by a researcher, veterinarian, medical doctor or other clinician. An appropriate "effective" amount in any individual case may be determined using techniques known to a person skilled in the art.

The phrase "pharmaceutically acceptable" is used herein to refer to those compounds, materials, compositions, and/or dosage forms which are, within the scope of sound medical judgment, suitable for use in contact with the tissues of human beings and animals without excessive toxicity, irritation, allergic response, immunogenicity or other problem or complication, commensurate with a reasonable benefit/risk ratio.

As used herein, the phrase "pharmaceutically acceptable carrier or excipient" refers to a pharmaceutically-acceptable material, composition, or vehicle, such as a liquid or solid filler, diluent, solvent, or encapsulating material. Excipients or carriers are generally safe, non-toxic and neither biologically nor otherwise undesirable and include excipients or carriers that are acceptable for veterinary use as well as human pharmaceutical use. In one embodiment, each component is "pharmaceutically acceptable" as defined herein. See, e.g., *Remington: The Science and Practice of Pharmacy,* 21st ed.; Lippincott Williams & Wilkins: Philadelphia, Pa., 2005; *Handbook of Pharmaceutical Excipients,* 6th ed.; Rowe et al., Eds.; The Pharmaceutical Press and the American Pharmaceutical Association: 2009; *Handbook of Pharmaceutical Additives,* 3rd ed.; Ash and Ash Eds.; Gower Publishing Company: 2007; *Pharmaceutical Preformulation and Formulation,* 2nd ed.; Gibson Ed.; CRC Press LLC: Boca Raton, Fla., 2009.

As used herein, the term "treating" or "treatment" refers to inhibiting the disease; for example, inhibiting a disease, condition or disorder in an individual who is experiencing or displaying the pathology or symptomatology of the disease, condition or disorder (i.e., arresting further development of the pathology and/or symptomatology) or ameliorating the disease; for example, ameliorating a disease, condition or disorder in an individual who is experiencing or displaying the pathology or symptomatology of the disease, condition or disorder (i.e., reversing the pathology and/or symptomatology) such as decreasing the severity of disease.

In some embodiments, the compounds of the invention are useful in preventing or reducing the risk of developing any of the diseases referred to herein; e.g., preventing or reducing the risk of developing a disease, condition or disorder in an individual who may be predisposed to the disease, condition or disorder but does not yet experience or display the pathology or symptomatology of the disease.

It is appreciated that certain features of the disclosure, which are, for clarity, described in the context of separate embodiments, can also be provided in combination in a single embodiment (while the embodiments are intended to be combined as if written in multiply dependent form). Conversely, various features of the disclosure which are, for brevity, described in the context of a single embodiment, can also be provided separately or in any suitable subcombination.

Combination Therapies

One or more additional pharmaceutical agents or treatment methods such as, for example, anti-viral agents, chemotherapeutics or other anti-cancer agents, immune enhancers, immunosuppressants, radiation, anti-tumor and anti-viral vaccines, cytokine therapy (e.g., IL2, GM-CSF, etc.), and/or tyrosine kinase inhibitors can be used in combination with compounds described herein for treatment or prevention of V617F-associated diseases, disorders or conditions, or diseases or conditions as described herein. The agents can be combined with the present compounds in a single dosage form, or the agents can be administered simultaneously or sequentially as separate dosage forms.

Compounds described herein can be used in combination with one or more other kinase inhibitors for the treatment of diseases, such as cancer, that are impacted by multiple signaling pathways. For example, a combination can include one or more inhibitors of the following kinases for the treatment of cancer: Akt1, Akt2, Akt3, TGF-βR, Pim, PKA, PKG, PKC, CaM-kinase, phosphorylase kinase, MEKK, ERK, MAPK, mTOR, EGFR, HER2, HER3, HER4, INS-R, IGF-1R, IR-R, PDGFαR, PDGFβR, CSF1R, KIT, FLK-II, KDR/FLK-1, FLK-4, fit-1, FGFR1, FGFR2, FGFR3, FGFR4, c-Met, Ron, Sea, TRKA, TRKB, TRKC, FLT3, VEGFR/Flt2, Flt4, EphA1, EphA2, EphA3, EphB2, EphB4, Tie2, Src, Fyn, Lck, Fgr, Btk, Fak, SYK, FRK, JAK, ABL, ALK and B-Raf. Additionally, the solid forms of the inhibitor as described herein can be combined with inhibitors of kinases associated with the PIK3/Akt/mTOR signaling pathway, such as PI3K, Akt (including Akt1, Akt2 and Akt3) and mTOR kinases.

In some embodiments, compounds described herein can be used in combination with one or more inhibitors of the enzyme or protein receptors such as HPK1, SBLB, TUT4, A2A/A2B, CD19, CD47, CDK2, STING, ALK2, LIN28, ADAR1, MAT2a, RIOK1, HDAC8, WDR5, SMARCA2, and DCLK1 for the treatment of diseases and disorders. Exemplary diseases and disorders include cancer, infection, inflammation and neurodegenerative disorders.

In some embodiments, compounds described herein can be used in combination with a therapeutic agent that targets an epigenetic regulator. Examples of epigenetic regulators include bromodomain inhibitors, the histone lysine methyltransferases, histone arginine methyl transferases, histone demethylases, histone deacetylases, histone acetylases, and DNA methyltransferases. Histone deacetylase inhibitors include, e.g., vorinostat.

For treating cancer and other proliferative diseases, compounds described herein can be used in combination with targeted therapies, including JAK kinase inhibitors (ruxolitinib, additional JAK1/2 and JAK1-selective, baricitinib or itacitinib), Pim kinase inhibitors (e.g., LGH447, INCB053914 and SGI-1776), PI3 kinase inhibitors including PI3K-delta selective and broad spectrum PI3K inhibitors (e.g., INCB50465 and INCB50797), PI3K-gamma inhibitors such as PI3K-gamma selective inhibitors, MEK inhibitors, CSF1R inhibitors (e.g., PLX3397 and LY3022855), TAM receptor tyrosine kinases inhibitors (Tyro-3, Axl, and Mer; e.g., INCB81776), angiogenesis inhibitors, interleukin receptor inhibitors, Cyclin Dependent kinase inhibitors, BRAF inhibitors, mTOR inhibitors, proteasome inhibitors (Bortezomib, Carfilzomib), HDAC-inhibitors (panobinostat, vorinostat), DNA methyl transferase inhibitors, dexamethasone, bromo and extra terminal family members inhibitors (for example, bromodomain inhibitors or BET inhibitors, such as OTX015, CPI-0610, INCB54329 or INCB57643), LSD1 inhibitors (e.g., GSK2979552, INCB59872 and INCB60003), arginase inhibitors (e.g., INCB1158), indoleamine 2,3-dioxygenase inhibitors (e.g., epacadostat, NLG919 or BMS-986205), PARP inhibitors (e.g., olaparib or rucaparib), and inhibitors of BTK such as ibrutinib.

For treating cancer and other proliferative diseases, compounds described herein can be used in combination with chemotherapeutic agents, agonists or antagonists of nuclear receptors, or other anti-proliferative agents. Compounds described herein can also be used in combination with a medical therapy such as surgery or radiotherapy, e.g., gamma-radiation, neutron beam radiotherapy, electron beam radiotherapy, proton therapy, brachytherapy, and systemic radioactive isotopes.

Examples of suitable chemotherapeutic agents include any of: abarelix, abiraterone, afatinib, aflibercept, aldesleukin, alemtuzumab, alitretinoin, allopurinol, altretamine, amidox, amsacrine, anastrozole, aphidicolon, arsenic trioxide, asparaginase, axitinib, azacitidine, bevacizumab, bexarotene, baricitinib, bendamustine, bicalutamide, bleomycin, bortezombi, bortezomib, brivanib, buparlisib, busulfan intravenous, busulfan oral, calusterone, camptosar, capecitabine, carboplatin, carmustine, cediranib, cetuximab, chlorambucil, cisplatin, cladribine, clofarabine, crizotinib, cyclophosphamide, cytarabine, dacarbazine, dacomitinib, dactinomycin, dalteparin sodium, dasatinib, dactinomycin, daunorubicin, decitabine, degarelix, denileukin, denileukin diftitox, deoxycoformycin, dexrazoxane, didox, docetaxel, doxorubicin, droloxafine, dromostanolone propionate, eculizumab, enzalutamide, epidophyllotoxin, epirubicin, epothilones, erlotinib, estramustine, etoposide phosphate, etoposide, exemestane, fentanyl citrate, filgrastim, floxuridine, fludarabine, fluorouracil, flutamide, fulvestrant, gefitinib, gemcitabine, gemtuzumab ozogamicin, goserelin acetate, histrelin acetate, ibritumomab tiuxetan, idarubicin, idelalisib, ifosfamide, imatinib mesylate, interferon alfa 2a, irinotecan, lapatinib ditosylate, lenalidomide, letrozole, leucovorin, leuprolide acetate, levamisole, lonafarnib, lomustine, meclorethamine, megestrol acetate, melphalan, mercaptopurine, methotrexate, methoxsalen, mithramycin, mitomycin C, mitotane, mitoxantrone, nandrolone phenpropionate, navelbene, necitumumab, nelarabine, neratinib, nilotinib, nilutamide, niraparib, nofetumomab, oserelin, oxaliplatin, paclitaxel, pamidronate, panitumumab, panobinostat, pazopanib, pegaspargase, pegfilgrastim, pemetrexed disodium, pentostatin, pilaralisib, pipobroman, plicamycin, ponatinib, porfimer, prednisone, procarbazine, quinacrine, ranibizumab, rasburicase, regorafenib, reloxafine, revlimid, rituximab, rucaparib, ruxolitinib, sorafenib, streptozocin, sunitinib, sunitinib maleate, tamoxifen, tegafur, temozolomide, teniposide, testolactone, tezacitabine, thalidomide, thioguanine, thiotepa, tipifarnib, topotecan, toremifene, tositumomab, trastuzumab, tretinoin, triapine, trimidox, triptorelin, uracil mustard, valrubicin, vandetanib, vinblastine, vincristine, vindesine, vinorelbine, vorinostat, veliparib, talazoparib, and zoledronate.

In some embodiments, compounds described herein can be used in combination with immune checkpoint inhibitors. Exemplary immune checkpoint inhibitors include inhibitors against immune checkpoint molecules such as CD27, CD28, CD40, CD122, CD96, CD73, CD47, OX40, GITR, CSF1R, JAK, PI3K delta, PI3K gamma, TAM, arginase, CD137 (also known as 4-1BB), ICOS, A2AR, B7-H3, B7-H4, BTLA, CTLA-4, LAG3 (e.g., INCAGN2385), TIM3 (e.g., INCB2390), VISTA, PD-1, PD-L1 and PD-L2. In some embodiments, the immune checkpoint molecule is a stimulatory checkpoint molecule selected from CD27, CD28, CD40, ICOS, OX40 (e.g., INCAGN1949), GITR (e.g., INCAGN1876) and CD137. In some embodiments, the immune checkpoint molecule is an inhibitory checkpoint molecule selected from A2AR, B7-H3, B7-H4, BTLA, CTLA-4, IDO, KIR, LAG3, PD-1, TIM3, and VISTA. In some embodiments, the compounds provided herein can be used in combination with one or more agents selected from KIR inhibitors, TIGIT inhibitors, LAIR1 inhibitors, CD160 inhibitors, 2B4 inhibitors and TGFR beta inhibitors.

In some embodiments, the inhibitor of an immune checkpoint molecule is a small molecule PD-L1 inhibitor. In some embodiments, the small molecule PD-L1 inhibitor has an IC50 less than 1 µM, less than 100 nM, less than 10 nM or less than 1 nM in a PD-L1 assay described in US Patent Publication Nos. US 20170107216, US 20170145025, US 20170174671, US 20170174679, US 20170320875, US 20170342060, US 20170362253, and US 20180016260, each of which is incorporated by reference in its entirety for all purposes.

In some embodiments, the inhibitor of an immune checkpoint molecule is an inhibitor of PD-1, e.g., an anti-PD-1 monoclonal antibody. In some embodiments, the anti-PD-1 monoclonal antibody is retifanlimab (also known as MGA012), nivolumab, pembrolizumab (also known as MK-3475), pidilizumab, SHR-1210, PDR001, ipilumimab or AMP-224. In some embodiments, the anti-PD-1 monoclonal antibody is nivolumab or pembrolizumab. In some embodiments, the anti-PD1 antibody is pembrolizumab. In some embodiments, the anti-PD1 antibody is nivolumab. In some embodiments, the anti-PD-1 monoclonal antibody is retifanlimab. In some embodiments, the anti-PD1 antibody is SHR-1210. Other anti-cancer agent(s) include antibody therapeutics such as 4-1BB (e.g. urelumab, utomilumab.

In some embodiments, the compounds of the disclosure can be used in combination with INCB086550.

In some embodiments, the inhibitor of an immune checkpoint molecule is an inhibitor of PD-L1, e.g., an anti-PD-L1 monoclonal antibody. In some embodiments, the anti-PD-L1 monoclonal antibody is BMS-935559, MEDI4736, MPDL3280A (also known as RG7446), or MSB0010718C. In some embodiments, the anti-PD-L1 monoclonal antibody is MPDL3280A or MEDI4736.

In some embodiments, the inhibitor of an immune checkpoint molecule is an inhibitor of CTLA-4, e.g., an anti-CTLA-4 antibody. In some embodiments, the anti-CTLA-4 antibody is ipilimumab, tremelimumab, AGEN1884, or CP-675,206.

In some embodiments, the inhibitor of an immune checkpoint molecule is an inhibitor of LAG3, e.g., an anti-LAG3 antibody. In some embodiments, the anti-LAG3 antibody is BMS-986016, LAG525, or INCAGN2385.

In some embodiments, the inhibitor of an immune checkpoint molecule is an inhibitor of TIM3, e.g., an anti-TIM3 antibody. In some embodiments, the anti-TIM3 antibody is INCAGN2390, MBG453, or TSR-022.

In some embodiments, the inhibitor of an immune checkpoint molecule is an inhibitor of GITR, e.g., an anti-GITR antibody. In some embodiments, the anti-GITR antibody is TRX518, MK-4166, INCAGN1876, MK-1248, AMG228, BMS-986156, GWN323, or MEDI1873.

In some embodiments, the inhibitor of an immune checkpoint molecule is an agonist of OX40, e.g., OX40 agonist antibody or OX40L fusion protein. In some embodiments, the anti-OX40 antibody is MEDI0562, MOXR-0916, PF-04518600, GSK3174998, or BMS-986178. In some embodiments, the OX40L fusion protein is MEDI6383.

In some embodiments, the inhibitor of an immune checkpoint molecule is an inhibitor of CD20, e.g., an anti-CD20 antibody. In some embodiments, the anti-CD20 antibody is obinutuzumab or rituximab.

The compounds of the present disclosure can be used in combination with bispecific antibodies. In some embodiments, one of the domains of the bispecific antibody targets PD-1, PD-L1, CTLA-4, GITR, OX40, TIM3, LAG3, CD137, ICOS, CD3 or TGFβ receptor.

In some embodiments, the compounds of the disclosure can be used in combination with one or more metabolic enzyme inhibitors. In some embodiments, the metabolic enzyme inhibitor is an inhibitor of IDO1, TDO, or arginase. Examples of IDO1 inhibitors include epacadostat, NLG919, BMS-986205, PF-06840003, IOM2983, RG-70099 and LY338196.

In some embodiments, the compounds described herein can be used in combination with one or more agents for the treatment of diseases such as cancer. In some embodiments, the agent is an alkylating agent, a proteasome inhibitor, a corticosteroid, or an immunomodulatory agent. Examples of an alkylating agent include cyclophosphamide (CY), melphalan (MEL), and bendamustine. In some embodiments, the proteasome inhibitor is carfilzomib. In some embodiments, the corticosteroid is dexamethasone (DEX). In some embodiments, the immunomodulatory agent is lenalidomide (LEN) or pomalidomide (POM).

Suitable antiviral agents contemplated for use in combination with compounds of the present disclosure can comprise nucleoside and nucleotide reverse transcriptase inhibitors (NRTIs), non-nucleoside reverse transcriptase inhibitors (NNRTIs), protease inhibitors and other antiviral drugs.

Example suitable NRTIs include zidovudine (AZT); didanosine (ddl); zalcitabine (ddC); stavudine (d4T); lamivudine (3TC); abacavir (1592U89); adefovir dipivoxil [bis(POM)-PMEA]; lobucavir (BMS-180194); BCH-10652; emitricitabine [(−)-FTC]; beta-L-FD4 (also called beta-L-D4C and named beta-L-2', 3'-dicleoxy-5-fluoro-cytidene); DAPD, ((−)-beta-D-2,6,-diamino-purine dioxolane); and lodenosine (FddA). Typical suitable NNRTIs include nevirapine (BI-RG-587); delaviradine (BHAP, U-90152); efavirenz (DMP-266); PNU-142721; AG-1549; MKC-442 (1-(ethoxy-methyl)-5-(1-methylethyl)-6-(phenylmethyl)-(2,4 (1H,3H)-pyrimidinedione); and (+)-calanolide A (NSC-675451) and B. Typical suitable protease inhibitors include saquinavir (Ro 31-8959); ritonavir (ABT-538); indinavir (MK-639); nelfnavir (AG-1343); amprenavir (141W94); lasinavir (BMS-234475); DMP-450; BMS-2322623; ABT-378; and AG-1 549. Other antiviral agents include hydroxyurea, ribavirin, IL-2, IL-12, pentafuside and Yissum Project No. 11607.

Suitable agents for use in combination with compounds described herein for the treatment of cancer include chemotherapeutic agents, targeted cancer therapies, immunotherapies or radiation therapy. Compounds described herein may be effective in combination with anti-hormonal agents for treatment of breast cancer and other tumors. Suitable examples are anti-estrogen agents including but not limited to tamoxifen and toremifene, aromatase inhibitors including but not limited to letrozole, anastrozole, and exemestane, adrenocorticosteroids (e.g. prednisone), progestins (e.g. megastrol acetate), and estrogen receptor antagonists (e.g. fulvestrant). Suitable anti-hormone agents used for treatment of prostate and other cancers may also be combined with compounds described herein. These include anti-androgens including but not limited to flutamide, bicalutamide, and nilutamide, luteinizing hormone-releasing hormone (LHRH) analogs including leuprolide, goserelin, triptorelin, and histrelin, LHRH antagonists (e.g. degarelix), androgen receptor blockers (e.g. enzalutamide) and agents that inhibit androgen production (e.g. abiraterone).

The compounds described herein may be combined with or in sequence with other agents against membrane receptor kinases especially for patients who have developed primary or acquired resistance to the targeted therapy. These therapeutic agents include inhibitors or antibodies against EGFR, Her2, VEGFR, c-Met, Ret, IGFR1, or Flt-3 and against cancer-associated fusion protein kinases such as Bcr-Abl and EML4-Alk. Inhibitors against EGFR include gefitinib and erlotinib, and inhibitors against EGFR/Her2 include but are not limited to dacomitinib, afatinib, lapitinib and neratinib. Antibodies against the EGFR include but are not limited to cetuximab, panitumumab and necitumumab. Inhibitors of c-Met may be used in combination with FGFR inhibitors. These include onartumzumab, tivantnib, and INC-280. Agents against Abl (or Bcr-Abl) include imatinib, dasatinib, nilotinib, and ponatinib and those against Alk (or EML4-ALK) include crizotinib.

Angiogenesis inhibitors may be efficacious in some tumors in combination with inhibitors described herein. These include antibodies against VEGF or VEGFR or kinase inhibitors of VEGFR. Antibodies or other therapeutic proteins against VEGF include bevacizumab and aflibercept. Inhibitors of VEGFR kinases and other anti-angiogenesis inhibitors include but are not limited to sunitinib, sorafenib, axitinib, cediranib, pazopanib, regorafenib, brivanib, and vandetanib Activation of intracellular signaling pathways is frequent in cancer, and agents targeting components of these pathways have been combined with receptor targeting agents to enhance efficacy and reduce resistance. Examples of agents that may be combined with compounds described herein include inhibitors of the PI3K-AKT-mTOR pathway, inhibitors of the Raf-MAPK pathway, inhibitors of JAK-STAT pathway, and inhibitors of protein chaperones and cell cycle progression.

Agents against the PI3 kinase include but are not limited topilaralisib, idelalisib, buparlisib. Inhibitors of mTOR such as rapamycin, sirolimus, temsirolimus, and everolimus may be combined with compounds described herein. Other suitable examples include but are not limited to vemurafenib and dabrafenib (Raf inhibitors) and trametinib, selumetinib and GDC-0973 (MEK inhibitors). Inhibitors of one or more JAKs (e.g., ruxolitinib, baricitinib, tofacitinib), Hsp90 (e.g., tanespimycin), cyclin dependent kinases (e.g., palbociclib), HDACs (e.g., panobinostat), PARP (e.g., olaparib), and proteasomes (e.g., bortezomib, carfilzomib) can also be combined with compounds described herein. In some embodiments, the JAK inhibitor is selective for JAK1 over JAK2 and JAK3.

Other suitable agents for use in combination with compounds described herein include chemotherapy combinations such as platinum-based doublets used in lung cancer and other solid tumors (cisplatin or carboplatin plus gemcitabine; cisplatin or carboplatin plus docetaxel; cisplatin or carboplatin plus paclitaxel; cisplatin or carboplatin plus pemetrexed) or gemcitabine plus paclitaxel bound particles.

Suitable chemotherapeutic or other anti-cancer agents include, for example, alkylating agents (including, without limitation, nitrogen mustards, ethylenimine derivatives, alkyl sulfonates, nitrosoureas and triazenes) such as uracil mustard, chlormethine, cyclophosphamide, ifosfamide, melphalan, chlorambucil, pipobroman, triethylene-melamine, triethylenethiophosphoramine, busulfan, carmustine, lomustine, streptozocin, dacarbazine, and temozolomide.

Other suitable agents for use in combination with compounds described herein include steroids including 17 alpha-ethinylestradiol, diethylstilbestrol, testosterone, prednisone, fluoxymesterone, methylprednisolone, methyltestosterone, prednisolone, triamcinolone, chlorotrianisene, hydroxyprogesterone, aminoglutethimide, and medroxyprogesteroneacetate.

Other suitable agents for use in combination with compounds described herein include: dacarbazine (DTIC), optionally, along with other chemotherapy drugs such as carmustine (BCNU) and cisplatin; the "Dartmouth regimen," which consists of DTIC, BCNU, cisplatin and tamoxifen; a combination of cisplatin, vinblastine, and DTIC; or temozolomide. Compounds described herein may also be combined with immunotherapy drugs, including cytokines such as interferon alpha, interleukin 2, and tumor necrosis factor (TNF) in.

Suitable chemotherapeutic or other anti-cancer agents include, for example, antimetabolites (including, without limitation, folic acid antagonists, pyrimidine analogs, purine analogs and adenosine deaminase inhibitors) such as methotrexate, 5-fluorouracil, floxuridine, cytarabine, 6-mercaptopurine, 6-thioguanine, fludarabine phosphate, pentostatine, and gemcitabine.

Suitable chemotherapeutic or other anti-cancer agents further include, for example, certain natural products and their derivatives (e.g., vinca alkaloids, antitumor antibiotics, enzymes, lymphokines and epipodophyllotoxins) such as vinblastine, vincristine, vindesine, bleomycin, dactinomycin, daunorubicin, doxorubicin, epirubicin, idarubicin, ara-C, paclitaxel, mithramycin, deoxycoformycin, mitomycin-C, L-asparaginase, interferons (especially IFN-α), etoposide, and teniposide.

Other cytotoxic agents include navelbene, CPT-11, anastrazole, letrazole, capecitabine, reloxafine, cyclophosphamide, ifosamide, and droloxafine.

Also suitable are cytotoxic agents such as epidophyllotoxin; an antineoplastic enzyme; a topoisomerase inhibitor; procarbazine; mitoxantrone; platinum coordination complexes such as cis-platin and carboplatin; biological response modifiers; growth inhibitors; antihormonal therapeutic agents; leucovorin; tegafur; and haematopoietic growth factors.

Other anti-cancer agent(s) include antibody therapeutics such as trastuzumab (Herceptin), antibodies to costimulatory molecules such as CTLA-4, 4-1BB, PD-L1 and PD-1 antibodies, or antibodies to cytokines (IL-10, TGF-β, etc.).

Other anti-cancer agents also include those that block immune cell migration such as antagonists to chemokine receptors, including CCR2 and CCR4.

Other anti-cancer agents also include those that augment the immune system such as adjuvants or adoptive T cell transfer.

Anti-cancer vaccines include dendritic cells, synthetic peptides, DNA vaccines and recombinant viruses. In some embodiments, tumor vaccines include the proteins from viruses implicated in human cancers such as Human Papilloma Viruses (HPV), Hepatitis Viruses (HBV and HCV) and Kaposi's Herpes Sarcoma Virus (KHSV). Non-limiting examples of tumor vaccines that can be used include peptides of melanoma antigens, such as peptides of gp100, MAGE antigens, Trp-2, MARTI and/or tyrosinase, or tumor cells transfected to express the cytokine GM-CSF.

The compounds of the present disclosure can be used in combination with bone marrow transplant for the treatment of a variety of tumors of hematopoietic origin (see e.g., U.S. Pat. Nos. 9,233,985, 10,065,974, 10,287,303, 8,524,867, the disclosures of which are incorporated by reference herein in their entireties).

Methods for the safe and effective administration of most of these chemotherapeutic agents are known to those skilled in the art. In addition, their administration is described in the standard literature. For example, the administration of many of the chemotherapeutic agents is described in the "Physicians' Desk Reference" (PDR, e.g., 1996 edition, Medical Economics Company, Montvale, NJ), the disclosure of which is incorporated herein by reference as if set forth in its entirety.

As provided throughout, the additional compounds, inhibitors, agents, etc. can be combined with the present compound in a single or continuous dosage form, or they can be administered simultaneously or sequentially as separate dosage forms.

Pharmaceutical Formulations and Dosage Forms

When employed as pharmaceuticals, the compounds of the disclosure can be administered in the form of pharmaceutical compositions. These compositions can be prepared in a manner well known in the pharmaceutical art, and can be administered by a variety of routes, depending upon whether local or systemic treatment is desired and upon the area to be treated. Administration may be topical (including transdermal, epidermal, ophthalmic and to mucous membranes including intranasal, vaginal and rectal delivery), pulmonary (e.g., by inhalation or insufflation of powders or aerosols, including by nebulizer; intratracheal or intranasal), oral, or parenteral. Parenteral administration includes intravenous, intraarterial, subcutaneous, intraperitoneal intramuscular or injection or infusion; or intracranial, e.g., intrathecal or intraventricular, administration. Parenteral administration can be in the form of a single bolus dose, or may be, for example, by a continuous perfusion pump. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

This disclosure also includes pharmaceutical compositions which contain, as the active ingredient, the compound of the disclosure or a pharmaceutically acceptable salt thereof, in combination with one or more pharmaceutically acceptable carriers (excipients). In some embodiments, the composition is suitable for topical administration. In making the compositions of the disclosure, the active ingredient is typically mixed with an excipient, diluted by an excipient or enclosed within such a carrier in the form of, for example, a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

In preparing a formulation, the active compound can be milled to provide the appropriate particle size prior to combining with the other ingredients. If the active compound is substantially insoluble, it can be milled to a particle size of less than 200 mesh. If the active compound is substantially water soluble, the particle size can be adjusted by milling to provide a substantially uniform distribution in the formulation, e.g. about 40 mesh.

The compounds of the disclosure may be milled using known milling procedures such as wet milling to obtain a particle size appropriate for tablet formation and for other formulation types. Finely divided (nanoparticulate) preparations of the compounds of the disclosure can be prepared by processes known in the art, e.g., see International App. No. WO 2002/000196.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the disclosure can be formulated so as to provide quick, sustained or delayed release of the active ingredient after administration to the patient by employing procedures known in the art.

The compositions can be formulated in a unit dosage form, each dosage containing from about 5 to about 1000 mg (1 g), more usually about 100 to about 500 mg, of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

In some embodiments, the compositions of the disclosure contain from about 5 to about 50 mg of the active ingredient. One having ordinary skill in the art will appreciate that this embodies compositions containing about 5 to about 10, about 10 to about 15, about 15 to about 20, about 20 to about 25, about 25 to about 30, about 30 to about 35, about 35 to about 40, about 40 to about 45, or about 45 to about 50 mg of the active ingredient.

In some embodiments, the compositions of the disclosure contain from about 50 to about 500 mg of the active ingredient. One having ordinary skill in the art will appreciate that this embodies compositions containing about 50 to about 100, about 100 to about 150, about 150 to about 200, about 200 to about 250, about 250 to about 300, about 350 to about 400, or about 450 to about 500 mg of the active ingredient.

In some embodiments, the compositions of the disclosure contain from about 500 to about 1000 mg of the active ingredient. One having ordinary skill in the art will appreciate that this embodies compositions containing about 500 to about 550, about 550 to about 600, about 600 to about 650, about 650 to about 700, about 700 to about 750, about 750 to about 800, about 800 to about 850, about 850 to about 900, about 900 to about 950, or about 950 to about 1000 mg of the active ingredient.

Similar dosages may be used of the compounds described herein in the methods and uses of the disclosure.

The active compound can be effective over a wide dosage range and is generally administered in a pharmaceutically effective amount. It will be understood, however, that the amount of the compound actually administered will usually be determined by a physician, according to the relevant circumstances, including the condition to be treated, the chosen route of administration, the actual compound administered, the age, weight, and response of the individual patient, the severity of the patient's symptoms, and the like.

For preparing solid compositions such as tablets, the principal active ingredient is mixed with a pharmaceutical excipient to form a solid preformulation composition containing a homogeneous mixture of a compound of the present disclosure. When referring to these preformulation compositions as homogeneous, the active ingredient is typically dispersed evenly throughout the composition so that the composition can be readily subdivided into equally effective unit dosage forms such as tablets, pills and capsules. This solid preformulation is then subdivided into unit dosage forms of the type described above containing from, for example, about 0.1 to about 1000 mg of the active ingredient of the present disclosure.

The tablets or pills of the present disclosure can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the compounds and compositions of the present disclosure can be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. In some embodiments, the compositions are administered by the oral or nasal respiratory route for local or systemic effect. Compositions can be nebulized by use of inert gases. Nebulized solutions may be breathed directly from the nebulizing device or the nebulizing device can be attached to a face mask, tent, or intermittent positive pressure breathing machine. Solution, suspension, or powder compositions can be administered orally or nasally from devices which deliver the formulation in an appropriate manner.

Topical formulations can contain one or more conventional carriers. In some embodiments, ointments can contain water and one or more hydrophobic carriers selected from, for example, liquid paraffin, polyoxyethylene alkyl ether, propylene glycol, white Vaseline, and the like. Carrier compositions of creams can be based on water in combination with glycerol and one or more other components, e.g. glycerinemonostearate, PEG-glycerinemonostearate and cetylstearyl alcohol. Gels can be formulated using isopropyl alcohol and water, suitably in combination with other components such as, for example, glycerol, hydroxyethyl cellulose, and the like. In some embodiments, topical formulations contain at least about 0.1, at least about 0.25, at least about 0.5, at least about 1, at least about 2, or at least about 5 wt % of the compound of the disclosure. The topical formulations can be suitably packaged in tubes of, for example, 100 g which are optionally associated with instructions for the treatment of the select indication, e.g., psoriasis or other skin condition.

The amount of compound or composition administered to a patient will vary depending upon what is being administered, the purpose of the administration, such as prophylaxis or therapy, the state of the patient, the manner of administration, and the like. In therapeutic applications, compositions can be administered to a patient already suffering from a disease in an amount sufficient to cure or at least partially arrest the symptoms of the disease and its complications. Effective doses will depend on the disease condition being treated as well as by the judgment of the attending clinician depending upon factors such as the severity of the disease, the age, weight and general condition of the patient, and the like.

The compositions administered to a patient can be in the form of pharmaceutical compositions described above. These compositions can be sterilized by conventional sterilization techniques, or may be sterile filtered. Aqueous solutions can be packaged for use as is, or lyophilized, the lyophilized preparation being combined with a sterile aqueous carrier prior to administration. The pH of the compound preparations typically will be between 3 and 11, more preferably from 5 to 9 and most preferably from 7 to 8. It will be understood that use of certain of the foregoing excipients, carriers, or stabilizers will result in the formation of pharmaceutical salts.

The therapeutic dosage of a compound of the present disclosure can vary according to, for example, the particular use for which the treatment is made, the manner of administration of the compound, the health and condition of the patient, and the judgment of the prescribing physician. The proportion or concentration of a compound of the disclosure in a pharmaceutical composition can vary depending upon a number of factors including dosage, chemical characteristics (e.g., hydrophobicity), and the route of administration. For example, the compounds of the disclosure can be provided in an aqueous physiological buffer solution containing about 0.1 to about 10% w/v of the compound for parenteral administration. Some typical dose ranges are from about 1 µg/kg to about 1 g/kg of body weight per day. In some embodiments, the dose range is from about 0.01 mg/kg to about 100 mg/kg of body weight per day. The dosage is likely to depend on such variables as the type and extent of progression of the disease or disorder, the overall health status of the particular patient, the relative biological efficacy of the compound selected, formulation of the excipient, and its route of administration. Effective doses can be extrapolated from dose-response curves derived from in vitro or animal model test systems.

The compositions of the disclosure can further include one or more additional pharmaceutical agents such as a chemotherapeutic, steroid, anti-inflammatory compound, or immunosuppressant, examples of which are listed herein.

Labeled Compounds and Assay Methods

Another aspect of the present disclosure relates to labeled compounds of the disclosure (radio-labeled, fluorescent-labeled, etc.) that would be useful not only in imaging techniques but also in assays, both in vitro and in vivo, for localizing and quantitating V617F in tissue samples, including human, and for identifying V617F inhibitors by binding of a labeled compound. Substitution of one or more of the atoms of the compounds of the present disclosure can also be useful in generating differentiated ADME (Adsorption, Distribution, Metabolism and Excretion.) Accordingly, the present disclosure includes V617F assays that contain such labeled or substituted compounds.

The present disclosure further includes isotopically-labeled compounds of the disclosure. An "isotopically" or "radio-labeled" compound is a compound of the disclosure where one or more atoms are replaced or substituted by an atom having an atomic mass or mass number different from the atomic mass or mass number typically found in nature (i.e., naturally occurring). Suitable radionuclides that may be incorporated in compounds of the present disclosure include but are not limited to $^{2}H$ (also written as D for deuterium), $^{3}H$ (also written as T for tritium), $^{11}C$, $^{13}C$, $^{14}C$, $^{13}N$, $^{15}N$, $^{15}O$, $^{17}O$, $^{18}O$, $^{18}F$, $^{35}S$, $^{36}Cl$, $^{82}Br$, $^{75}Br$, $^{76}Br$, $^{77}Br$, $^{123}I$, $^{124}I$, $^{125}I$ and $^{131}I$. For example, one or more hydrogen atoms in a compound of the present disclosure can be replaced by deuterium atoms (e.g., one or more hydrogen atoms of a $C_{1-6}$ alkyl group of Formula I can be optionally substituted with deuterium atoms, such as —$CD_3$ (i.e., trideuteromethyl) being substituted for —$CH_3$). In some embodiments, alkyl groups of the disclosed Formulas (e.g., Formula I, Formula Ia, etc.) can be perdeuterated (e.g., trideuteromethyl (—$CD_3$), pentadeuteroethyl (—$CD_2CD_3$), heptadeuteroisopropyl (—$CD(CD_3)_2$, and the like.

In some embodiments, alkoxy groups of the disclosed Formulas (e.g., Formula I, Formula Ia, etc.) can be perdeuterated (e.g., trideuteromethoxy (—$OCD_3$), pentadeuteroethoxy (—$OCD_2CD_3$), heptadeuteroisopropoxy (—$OCD(CD_3)_2$, and the like.

One or more constituent atoms of the compounds presented herein can be replaced or substituted with isotopes of the atoms in natural or non-natural abundance. In some embodiments, the compound includes at least one deuterium atom. For example, one or more hydrogen atoms in a compound presented herein can be replaced or substituted by deuterium (e.g., one or more hydrogen atoms of a $C_{1-6}$ alkyl group can be replaced by deuterium atoms, such as —$CD_3$ being substituted for —$CH_3$). In some embodiments, the compound includes two or more deuterium atoms. In some embodiments, the compound includes 1-2, 1-3, 1-4, 1-5, 1-6, 1-8, 1-10, 1-12, 1-14, 1-16, 1-18, or 1-20 deuterium atoms. In some embodiments, all of the hydrogen atoms in a compound can be replaced or substituted by deuterium atoms.

In some embodiments, each hydrogen atom of the compounds provided herein, such as hydrogen atoms attached to carbon atoms of alkyl, alkoxy, phenyl, dihydroisobenzofuranyl, and indazolyl substituents, as described herein, is optionally replaced by deuterium atoms.

In some embodiments, each hydrogen atom of the compounds provided herein, such as hydrogen atoms attached to carbon atoms of alkyl, alkoxy, phenyl, and indazolyl substituents, as described herein, is optionally replaced by deuterium atoms.

In some embodiments, each hydrogen atom of the compounds provided herein, such as hydrogen atoms to carbon atoms of alkyl, alkoxy, phenyl, and indazolyl substituents, as described herein, is replaced by deuterium atoms (i.e., the alkyl, alkoxy, phenyl, dihydroisobenzofuranyl, and indazolyl substituents are perdeuterated).

In some embodiments, each hydrogen atom of the compounds provided herein, such as hydrogen atoms to carbon atoms of alkyl, alkoxy, phenyl, and indazolyl substituents, as described herein, is replaced by deuterium atoms (i.e., the alkyl, alkoxy, phenyl, and indazolyl substituents are perdeuterated).

In some embodiments, 1, 2, 3, 4, 5, 6, 7, 8, 9, 10, 11, or 12 hydrogen atoms, attached to carbon atoms of alkyl, alkoxy, phenyl, dihydroisobenzofuranyl, and indazolyl substituents, as described herein, are optionally replaced by deuterium atoms.

In some embodiments, 1, 2, 3, 4, 5, 6, 7, or 8 hydrogen atoms, attached to carbon atoms of alkyl, alkoxy, phenyl, dihydroisobenzofuranyl, and indazolyl substituents, as described herein, are optionally replaced by deuterium atoms.

In some embodiments, 1, 2, 3, 4, 5, 6, 7, 8, 9, 10, 11, or 12 hydrogen atoms, attached to carbon atoms of alkyl, alkoxy, phenyl, and indazolyl substituents, as described herein, are optionally replaced by deuterium atoms.

In some embodiments, 1, 2, 3, 4, 5, 6, 7, or 8 hydrogen atoms, attached to carbon atoms of alkyl, alkoxy, phenyl, and indazolyl substituents, as described herein, are optionally replaced by deuterium atoms.

In some embodiments, the compound provided herein (e.g., the compound of any of Formulas I-Vc), or a pharmaceutically acceptable salt thereof, comprises at least one deuterium atom.

In some embodiments, the compound provided herein (e.g., the compound of any of Formulas I-Vc), or a pharmaceutically acceptable salt thereof, comprises two or more deuterium atoms.

In some embodiments, the compound provided herein (e.g., the compound of any of Formulas I-Vc), or a pharmaceutically acceptable salt thereof, comprises three or more deuterium atoms.

In some embodiments, for a compound provided herein (e.g., the compound of any of Formulas I-Vc), or a pharmaceutically acceptable salt thereof, all of the hydrogen atoms are replaced by deuterium atoms (i.e., the compound is "perdeuterated").

Synthetic methods for including isotopes into organic compounds are known in the art (Deuterium Labeling in Organic Chemistry by Alan F. Thomas (New York, N.Y., Appleton-Century-Crofts, 1971; The Renaissance of H/D Exchange by Jens Atzrodt, Volker Derdau, Thorsten Fey and Jochen Zimmermann, Angew. Chem. Int. Ed. 2007, 7744-7765; The Organic Chemistry of Isotopic Labelling by James R. Hanson, Royal Society of Chemistry, 2011). Isotopically labeled compounds can be used in various studies such as NMR spectroscopy, metabolism experiments, and/or assays.

Substitution with heavier isotopes, such as deuterium, may afford certain therapeutic advantages resulting from greater metabolic stability, for example, increased in vivo half-life or reduced dosage requirements, and hence may be preferred in some circumstances. (see e.g., A. Kerekes et. al. *J. Med. Chem.* 2011, 54, 201-210; R. Xu et. al. *J. Label Compd. Radiopharm.* 2015, 58, 308-312). In particular, substitution at one or more metabolism sites may afford one or more of the therapeutic advantages.

The radionuclide that is incorporated in the instant radiolabeled compounds will depend on the specific application of that radio-labeled compound. For example, for in vitro V617F labeling and competition assays, compounds that incorporate $^3$H, $^{14}$C, $^{82}$Br, $^{125}$I, $^{131}$I or $^{35}$S can be useful. For radio-imaging applications $^{11}$C, $^{18}$F, $^{125}$I, $^{123}$I, $^{124}$I, $^{131}$I, $^{75}$Br, $^{76}$Br or $^{77}$Br can be useful.

It is understood that a "radio-labeled" or "labeled compound" is a compound that has incorporated at least one radionuclide. In some embodiments, the radionuclide is selected from the group consisting of $^3$H, $^{14}$C, $^{125}$I, $^{35}$S and $^{82}$Br.

The present disclosure can further include synthetic methods for incorporating radio-isotopes into compounds of the disclosure. Synthetic methods for incorporating radio-isotopes into organic compounds are well known in the art, and an ordinary skill in the art will readily recognize the methods applicable for the compounds of disclosure.

A labeled compound of the disclosure can be used in a screening assay to identify/evaluate compounds. For example, a newly synthesized or identified compound (i.e., test compound) which is labeled can be evaluated for its ability to bind V617F by monitoring its concentration variation when contacting with V617F, through tracking of the labeling. For example, a test compound (labeled) can be evaluated for its ability to reduce binding of another compound which is known to bind to V617F (i.e., standard compound). Accordingly, the ability of a test compound to compete with the standard compound for binding to V617F directly correlates to its binding affinity. Conversely, in some other screening assays, the standard compound is labeled and test compounds are unlabeled. Accordingly, the concentration of the labeled standard compound is monitored in order to evaluate the competition between the standard compound and the test compound, and the relative binding affinity of the test compound is thus ascertained.

Kits

The present disclosure also includes pharmaceutical kits useful, for example, in the treatment or prevention of V617F-associated diseases or disorders as described herein, which include one or more containers containing a pharmaceutical composition comprising a therapeutically effective amount of a compound of the disclosure. Such kits can further include, if desired, one or more of various conventional pharmaceutical kit components, such as, for example, containers with one or more pharmaceutically acceptable carriers, additional containers, etc., as will be readily apparent to those skilled in the art. Instructions, either as inserts or as labels, indicating quantities of the components to be administered, guidelines for administration, and/or guidelines for mixing the components, can also be included in the kit.

The invention will be described in greater detail by way of specific examples. The following examples are offered for illustrative purposes, and are not intended to limit the invention in any manner. Those of skill in the art will readily recognize a variety of non-critical parameters which can be changed or modified to yield essentially the same results.

EXAMPLES

Preparatory LC-MS purifications of some of the compounds prepared were performed on Waters mass directed fractionation systems. The basic equipment setup, protocols, and control software for the operation of these systems have been described in detail in the literature (see e.g. "Two-Pump At Column Dilution Configuration for Preparative LC-MS", K. Blom, *J. Combi. Chem.*, 4, 295 (2002); "Optimizing Preparative LC-MS Configurations and Methods for Parallel Synthesis Purification", K. Blom, R. Sparks, J. Doughty, G. Everlof, T. Haque, A. Combs, *J. Combi. Chem.*, 5, 670 (2003); and "Preparative LC-MS Purification: Improved Compound Specific Method Optimization", K. Blom, B. Glass, R. Sparks, A. Combs, *J. Combi. Chem.*, 6, 874-883 (2004)).

The compounds separated were typically subjected to analytical liquid chromatography mass spectrometry (LCMS) for purity analysis under the following conditions: Instrument=Agilent 1100 series, LC/MSD; Column: Waters Sunfire™ $C_{18}$ 5 µm, 2.1×50 mm, Buffers: mobile phase A: 0.025% TFA in water and mobile phase B: acetonitrile; gradient 2% to 80% B in 3 minutes with flow rate 2.0 mL/minute.

Some of the compounds prepared were also separated on a preparative scale by reverse-phase high performance liquid chromatography (RP-HPLC) with MS detector or flash chromatography (silica gel) as indicated in the Examples. Typical preparative reverse-phase high performance liquid chromatography (RP-HPLC) column conditions are as follows:

pH=2 purifications: Waters Sunfire™ $C_{18}$ 5 µm, 30×100 mm or Waters XBridge™ $C_{18}$ 5 µm, 30×100 mm column, eluting with mobile phase A: 0.1% TFA (trifluoroacetic acid) in water and mobile phase B: acetonitrile; the flow rate was 60 mL/minute, the separating gradient was optimized for each compound using the Compound Specific Method Optimization protocol as described in the literature (see e.g., "Preparative LCMS Purification: Improved Compound Specific Method Optimization", K. Blom, B. Glass, R. Sparks, A. Combs, *J. Comb. Chem.*, 6, 874-883 (2004)). pH=10 purifications: Waters XBridge™ $C_{18}$ 5 µm, 30×100 mm column, eluting with mobile phase A: 0.1% $NH_4OH$ in water and mobile phase B: acetonitrile; the flow rate was 60 mL/minute, the separating gradient was optimized for each compound using the Compound Specific Method Optimization protocol as described in the literature (see e.g., "Preparative LCMS Purification: Improved Compound Specific Method Optimization", K. Blom, B. Glass, R. Sparks, A. Combs, *J. Comb. Chem.*, 6, 874-883 (2004)).

Example 1. Methyl ((1R,3R)-3-(8-(4-fluorophenyl)-7-(3-methoxy-1-methyl-1H-pyrazol-4-yl)-3-methyl-2-oxo-3,6-dihydroimidazo[4,5-d]pyrrolo[2,3-b]pyridin-1(2H)-yl)cyclopentyl)carbamate

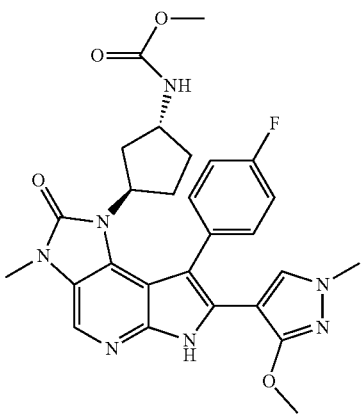

Step 1. tert-Butyl ((1R,3R)-3-((5-nitro-1-(phenylsulfonyl)-1H-pyrrolo[2,3-b]pyridin-4-yl)amino)cyclopentyl)carbamate

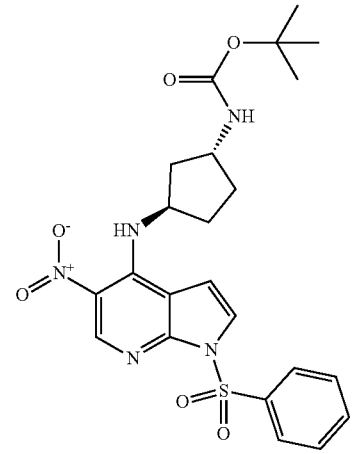 [SMILES: CC(C)(C)OC(=O)N[C@@H]1CC[C@@H](Nc2c([N+](=O)[O-])cnc3c2ccn3S(=O)(=O)c2ccccc2)C1]

A mixture of 4-chloro-5-nitro-1-(phenylsulfonyl)-1H-pyrrolo[2,3-b]pyridine (5.07 g, 15.0 mmol), tert-butyl ((1R,3R)-3-aminocyclopentyl)carbamate (3.15 g, 15.75 mmol) and $Et_3N$ (4.18 mL, 30.0 mmol) in acetonitrile (45 mL) was stirred at 70° C. for 1 h. The solvent was removed and the residue was washed with water, filtered, and dried to provide the product. LC-MS calculated for $C_{23}H_{28}N_5O_6S$ $(M+H)^+$: m/z=502.2; found 502.2.

Step 2. tert-Butyl ((1R,3R)-3-((5-amino-1-(phenylsulfonyl)-1H-pyrrolo[2,3-b]pyridin-4-yl)amino)cyclopentyl)carbamate

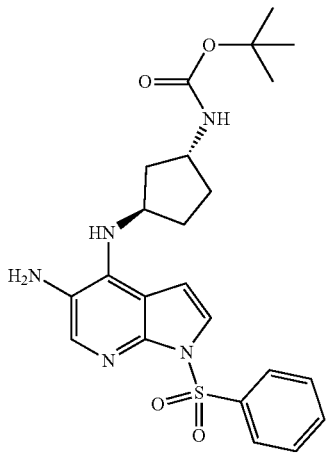 [SMILES: CC(C)(C)OC(=O)N[C@@H]1CC[C@@H](Nc2c(N)cnc3c2ccn3S(=O)(=O)c2ccccc2)C1]

To a solution of tert-butyl ((1R,3R)-3-((5-nitro-1-(phenylsulfonyl)-1H-pyrrolo[2,3-b]pyridin-4-yl)amino)cyclopentyl)carbamate (7.52 g, 15.0 mmol) in THF (18.0 mL)/ethanol (54.0 mL) was added iron (8.38 g, 150 mmol) followed by 1N HCl (5.0 mL) and then the reaction mixture was stirred at 70° C. for 4 h. The mixture was filtered through Celite and washed with ethyl acetate. The organic layer was concentrated and the resulting residue was dissolved in ethyl acetate which was then washed with saturated NaHCO$_3$ solution. The organic solution was concentrated to provide the desired product. LC-MS calculated for C$_{23}$H$_{30}$N$_5$O$_4$S (M+H)$^+$: m/z=472.2; found 472.3.

Step 3. tert-Butyl ((1R,3R)-3-(3-methyl-2-oxo-6-(phenylsulfonyl)-3,6-dihydroimidazo[4,5-d]pyrrolo[2,3-b]pyridin-1(2H)-yl)cyclopentyl)carbamate

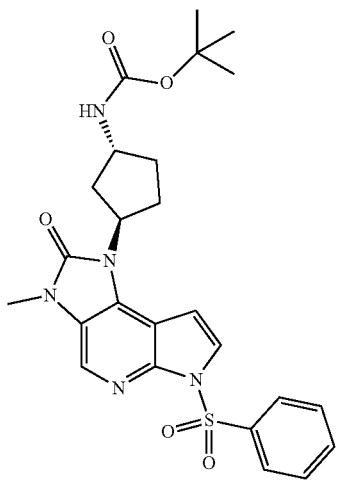 [SMILES: Cn1c(=O)n([C@@H]2CC[C@@H](NC(=O)OC(C)(C)C)C2)c2c3ccn(S(=O)(=O)c4ccccc4)c3ncc21]

A mixture of tert-butyl ((1R,3R)-3-((5-amino-1-(phenylsulfonyl)-1H-pyrrolo[2,3-b]pyridin-4-yl)amino)cyclopentyl)carbamate (6.37 g, 13.5 mmol), DMAP (2.474 g, 20.25 mmol) and CDI (6.57 g, 40.5 mmol) in AcCN (30 mL) was stirred at 70° C. for 2 h. The solvent was removed and the residue was dissolved in ethyl acetate, and washed sequentially with water, cold 1N HCl, water, and brine. The organic phase was dried and concentrated. The resulting residue was dissolved in DMF (30.0 mL), K$_2$CO$_3$ (5.60 g, 40.5 mmol) and MeI (2.53 ml, 40.5 mmol) were added, and the reaction mixture was stirred at room temperature for 2 h. The mixture was diluted with ethyl acetate and washed with water, then the organic phase was dried and concentrated. The residue was purified on silica gel (120 g, 0-80% EtOAc in hexanes) to provide the desired product. LC-MS calculated for C$_{25}$H$_{30}$N$_5$O$_5$S (M+H)$^+$: m/z=512.2; found 512.2.

Step 4. tert-Butyl ((1R,3R)-3-(7-bromo-3-methyl-2-oxo-6-(phenylsulfonyl)-3,6-dihydroimidazo[4,5-d]pyrrolo[2,3-b]pyridin-1(2H)-yl)cyclopentyl)carbamate

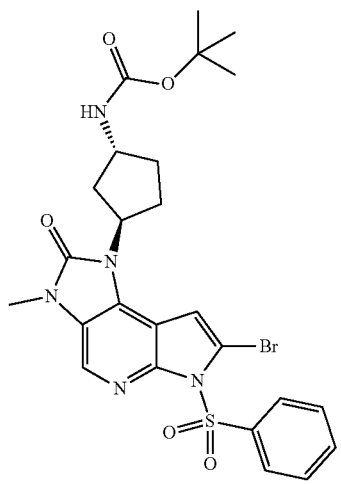 [SMILES: Cn1c(=O)n([C@@H]2CC[C@@H](NC(=O)OC(C)(C)C)C2)c2c3cc(Br)n(S(=O)(=O)c4ccccc4)c3ncc21]

LDA (2.0 M in THF) (14.3 mL, 28.6 mmol) was added to a solution of tert-butyl ((1R,3R)-3-(3-methyl-2-oxo-6-(phenylsulfonyl)-3,6-dihydroimidazo[4,5-d]pyrrolo[2,3-b]pyridin-1(2H)-yl)cyclopentyl)carbamate (5.63 g, 11.00 mmol) in THF (110.0 mL) at −78° C. and stirred for 30 min. At this time, 1,2-dibromo-1,1,2,2-tetrachloroethane (5.01 g, 15.40 mmol) in THF (10 mL) was added to the reaction mixture. After stirring for an additional 40 min the reaction was quenched by adding saturated NH$_4$Cl solution. The mixture was diluted with ethyl acetate and washed with water, and the organic phase was dried and concentrated. The resulting residue was purified on silica gel (120 g, 0-80% EtOAc in hexanes) to provide the desired product. LC-MS calculated for C$_{25}$H$_{29}$BrN$_5$O$_5$S (M+H)$^+$: m/z=590.1, 592.1; found 590.2, 592.1.

Step 5. tert-butyl ((1R,3R)-3-(7-(3-methoxy-1-methyl-1H-pyrazol-4-yl)-3-methyl-2-oxo-6-(phenylsulfonyl)-3,6-dihydroimidazo[4,5-d]pyrrolo[2,3-b]pyridin-1(2H)-yl)cyclopentyl)carbamate

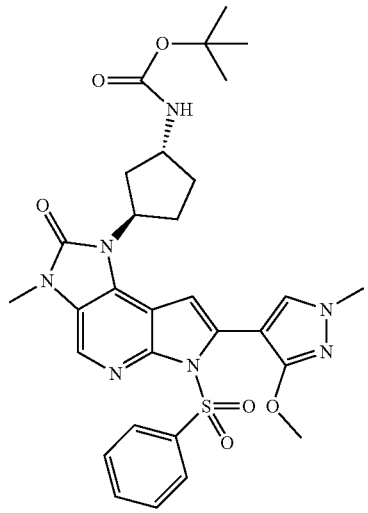

A mixture of tert-butyl ((1R,3R)-3-(7-bromo-3-methyl-2-oxo-6-(phenylsulfonyl)-3,6-dihydroimidazo[4,5-d]pyrrolo[2,3-b]pyridin-1(2H)-yl)cyclopentyl)carbamate (6.50 g, 11.0 mmol), 3-methoxy-1-methyl-4-(4,4,5,5-tetramethyl-1,3,2-dioxaborolan-2-yl)-1H-pyrazole (4.71 g, 19.80 mmol), $K_3PO_4$ (7.00 g, 33.0 mmol) and $Pd(Ph_3P)_4$ (1.907 g, 1.650 mmol) in dioxane (50.0 mL)/water (8.0 mL) was evacuated and backfilled with nitrogen (this process was repeated a total of three times), and then the reaction was stirred at 105° C. for 3 h. The mixture was diluted with ethyl acetate and washed with water, then the organic phase was dried and concentrated. The residue was purified on silica gel (120 g, 0-100% EtOAc in hexanes) to provide the desired product. LC-MS calculated for $C_{30}H_{36}N_7O_6S$ $(M+H)^+$: m/z=622.2; found 622.3.

Step 6. tert-Butyl ((1R,3R)-3-(8-bromo-7-(3-methoxy-1-methyl-1H-pyrazol-4-yl)-3-methyl-2-oxo-6-(phenylsulfonyl)-3,6-dihydroimidazo[4,5-d]pyrrolo[2,3-b]pyridin-1(2H)-yl)cyclopentyl)carbamate

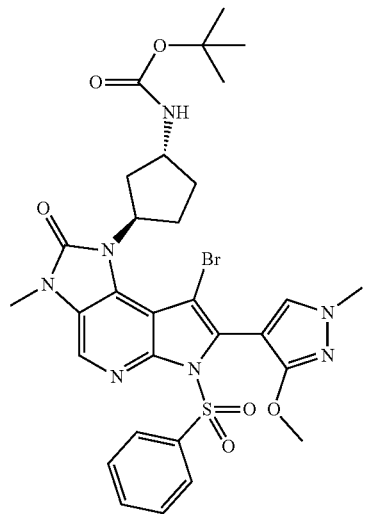

Bromine (1.542 g, 9.65 mmol) in $CH_2Cl_2$ (2.0 mL) was added to a solution of tert-butyl ((1R,3R)-3-(7-(3-methoxy-1-methyl-1H-pyrazol-4-yl)-3-methyl-2-oxo-6-(phenylsulfonyl)-3,6-dihydroimidazo[4,5-d]pyrrolo[2,3-b]pyridin-1 (2H)-yl)cyclopentyl)carbamate (5.00 g, 8.04 mmol) in $CH_2Cl_2$ (40.0 mL) at 0° C. and then stirred for 30 min. The reaction was quenched by adding saturated $NaHCO_3$, and the resulting mixture was extracted with ethyl acetate. The organic phase was dried and concentrated to provide the desired product which was used in the next step directly. LC-MS calculated for $C_{30}H_{35}BrN_7O_6S$ $(M+H)^+$: m/z=700.2, 702.2; found 700.3, 702.3.

Step 7. Methyl ((1R,3R)-3-(8-bromo-7-(3-methoxy-1-methyl-1H-pyrazol-4-yl)-3-methyl-2-oxo-6-(phenylsulfonyl)-3,6-dihydroimidazo[4,5-d]pyrrolo[2,3-b]pyridin-1(2H)-yl)cyclopentyl)carbamate

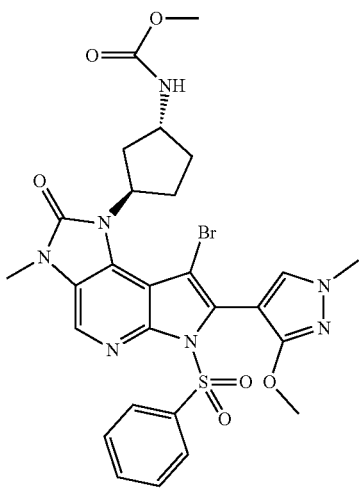

TFA (10 mL) was added to a solution of tert-butyl ((1R,3R)-3-(8-bromo-7-(3-methoxy-1-methyl-1H-pyrazol-4-yl)-3-methyl-2-oxo-6-(phenylsulfonyl)-3,6-dihydroimidazo[4,5-d]pyrrolo[2,3-b]pyridin-1(2H)-yl)cyclopentyl)carbamate (5.60 g, 8.0 mmol) in $CH_2Cl_2$ (10.0 mL) and then the reaction was stirred for 30 min. The mixture was concentrated and then the residue was dissolved in $CH_2Cl_2$ (40 mL) and water (20.0 mL) followed by adding $Na_2CO_3$ (4.24 g, 40.0 mmol) and methyl chloroformate (0.929 mL, 12.00 mmol) and then stirred at rt for 10 min. The mixture was diluted with $CH_2Cl_2$ and washed with water, then the organic phase was dried and concentrated. The residue was purified on silica gel (120 g, 0-100% EtOAc in $CH_2Cl_2$) to provide the desired product. LC-MS calculated for $C_{27}H_{29}BrN_7O_6S$ $(M+H)^+$: m/z=658.1, 660.1; found 658.2, 660.3.

Step 8. methyl ((1R,3R)-3-(8-(4-fluorophenyl)-7-(3-methoxy-1-methyl-1H-pyrazol-4-yl)-3-methyl-2-oxo-3,6-dihydroimidazo[4,5-d]pyrrolo[2,3-b]pyridin-1(2H)-yl)cyclopentyl)carbamate A screw-cap vial equipped with a magnetic stir bar was charged with methyl ((1R,3R)-3-(8-bromo-7-(3-methoxy-1-methyl-1H-pyrazol-4-yl)-3-methyl-2-oxo-6-(phenylsulfonyl)-3,6-dihydroimidazo[4,5-d]pyrrolo[2,3-b]pyridin-1 (2H)-yl)cyclopentyl)carbamate (10.0 mg, 0.015 mmol), (4-fluorophenyl)boronic acid (4.25 mg, 0.030 mmol), K₃PO₄ (9.67 mg, 0.046 mmol), Pd(Ph₃P)₄ (3.51 mg, 3.04 µmol) and dioxane (0.8 mL)/water (0.2 mL). The vial was sealed with a Teflon-lined septum, then evacuated and backfilled with nitrogen (this process was repeated a total of three times). The reaction mixture was stirred at 105° C. for 2 h. To this mixture was then added methanol (1.0 mL) and NaOH (4N, 0.20 mL) and the mixture was stirred at 80° C. for an additional 15 min to remove the protecting group. The mixture was diluted with acetonitrile/water and adjusted to pH~1 by adding 6 N HCl solution and then purified using prep-LCMS (XBridge C18 column, eluting with a gradient of acetonitrile/water containing 0.1% TFA, at flow rate of 60 mL/min) to give the product as a TFA salt. LC-MS calculated for $C_{27}H_{29}FN_7O_4(M+H)^+$: m/z=534.2; found 534.3. ¹H NMR (600 MHz, DMSO) δ 11.88 (s, 1H), 8.30 (s, 1H), 7.44 (dt, J=16.2, 7.2 Hz, 2H), 7.38-7.32 (m, 2H), 6.96 (d, J=6.9 Hz, 1H), 6.86 (s, 1H), 4.05 (h, J=8.0 Hz, 1H), 3.97-3.90 (m, 1H), 3.85 (s, 3H), 3.61 (s, 3H), 3.52 (s, 3H), 3.39 (s, 3H) 2.09 (ddd, J=13.2, 8.4, 4.8 Hz, 1H), 1.90 (m, 1H), 1.88 (d, J=8.5 Hz, 1H), 1.52-1.46 (m, 1H), 1.29 (q, J=11.3 Hz, 1H), 0.81 (m, 1H).

Example 2. Methyl ((1R,3R)-3-(7-(3-methoxy-1-methyl-1H-pyrazol-4-yl)-3-methyl-2-oxo-8-phenyl-3,6-dihydroimidazo[4,5-d]pyrrolo[2,3-b]pyridin-1(2H)-yl)cyclopentyl)carbamate

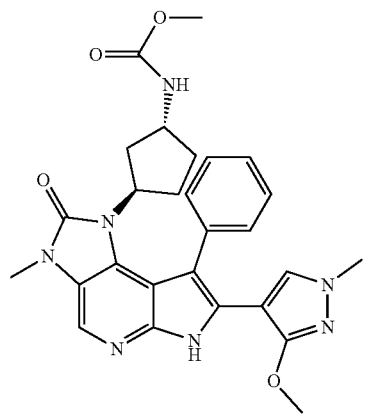

This compound was prepared according to the procedure described in Example 1, Step 8, replacing (4-fluorophenyl) boronic acid with phenyl boronic acid. LCMS calculated for $C_{27}H_{30}N_7O_4$ $(M+H)^+$ m/z=516.2; found 516.3. ¹H NMR (600 MHz, DMSO) δ 11.84 (s, 1H), 8.30 (s, 1H), 7.57-7.49 (m, 3H), 7.41 (dd, J=16.0, 7.1 Hz, 2H), 6.81 (d, J=6.9 Hz, 1H), 6.79 (s, 1H), 4.02 (h, J=7.0 Hz, 1H), 3.87 (m, 1H), 3.84 (s, 3H), 3.58 (s, 3H), 3.52 (s, 3H), 3.40 (s, 3H), 2.07 (ddd, J=13.4, 7.9, 4.9 Hz, 1H), 1.93-1.80 (m, 2H), 1.43 (dt, J=10.7, 8.2 Hz, 1H), 1.22 (td, J=11.8, 8.2 Hz, 1H), 0.80-0.71 (m, 1H).

Example 3. Methyl ((1R,3R)-3-(8-(3-fluorophenyl)-7-(3-methoxy-1-methyl-1H-pyrazol-4-yl)-3-methyl-2-oxo-3,6-dihydroimidazo[4,5-d]pyrrolo[2,3-b]pyridin-1(2H)-yl)cyclopentyl)carbamate

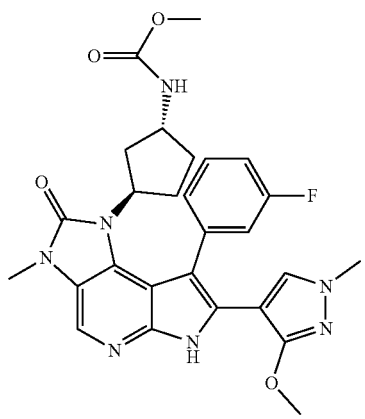

This compound was prepared according to the procedure described in Example 1, Step 8, replacing (4-fluorophenyl) boronic acid with (3-fluorophenyl)boronic acid. LC-MS calculated for $C_{27}H_{29}FN_7O_4(M+H)^+$: m/z=534.2; found 534.3. ¹H NMR (600 MHz, DMSO) δ 11.81 (s, 1H), 8.25 (d, J=2.5 Hz, 1H), 7.56 (q, J=7.4 Hz, 1H), 7.31 (m, 1H), 7.25 (d, J=7.9 Hz, 2H), 7.01 (s, 1H), 6.88 (s, 1H), 4.04 (br, 1H), 3.84 (m, 1H), 3.82 (s, 3H), 3.62 (s, 3H), 3.52 (s, 3H), 3.40 (s, 3H), 2.11 (br, 1H), 1.92-1.87 (m, 2H), 1.54-1.46 (m, 1H), 1.24 (q, J=11.2 Hz, 1H), 0.83 (br, 1H).

Example 4. Methyl ((1R,3R)-3-(8-(3-fluoro-4-methoxyphenyl)-7-(3-methoxy-1-methyl-1H-pyrazol-4-yl)-3-methyl-2-oxo-3,6-dihydroimidazo[4,5-d]pyrrolo[2,3-b]pyridin-1(2H)-yl)cyclopentyl)carbamate

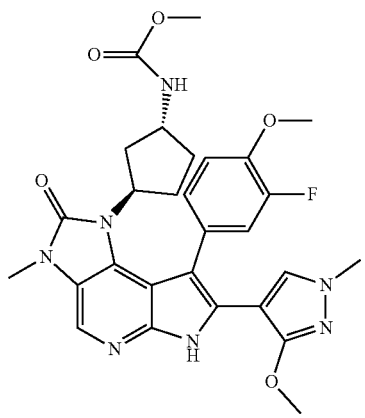

This compound was prepared according to the procedure described in Example 1, Step 8, replacing (4-fluorophenyl) boronic acid with (3-fluoro-4-methoxyphenyl)boronic acid. LC-MS calculated for $C_{28}H_{31}FN_7O_5(M+H)^+$: m/z=564.2; found 564.3. ¹H NMR (500 MHz, DMSO) δ 11.16 (s, 1H), 8.12 (s, 1H), 7.28 (t, J=8.7 Hz, 1H), 7.23-7.14 (m, 2H), 6.96 (s, 1H), 6.51 (br, 1H), 4.13-4.06 (m, 1H), 4.02-3.97 (m, 1H), 3.95 (s, 3H), 3.86 (s, 3H), 3.63 (s, 3H), 3.54 (s, 3H), 3.39 (s, 3H), 2.17 (ddd, J=13.5, 8.5, 5.1 Hz, 1H), 2.05-1.90 (m, 2H), 1.57-1.50 (m, 1H), 1.33 (q, J=11.3 Hz, 1H), 0.91-0.81 (m, 1H).

Example 5. Methyl ((1R,3R)-3-(7-(3-methoxy-1-methyl-1H-pyrazol-4-yl)-3-methyl-8-(1-(methyl-d3)-1H-indazol-5-yl)-2-oxo-3,6-dihydroimidazo[4,5-d]pyrrolo[2,3-b]pyridin-1(2H)-yl)cyclopentyl)carbamate

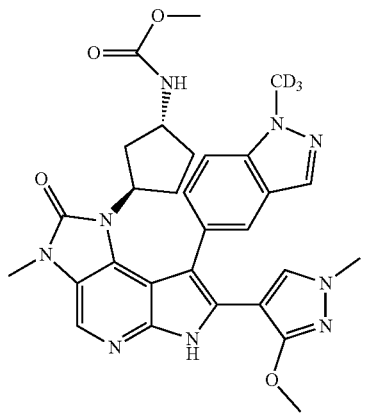

This compound was prepared according to the procedure described in Example 1, Step 8, replacing (4-fluorophenyl)boronic acid with (1-(methyl-d₃)-1H-indazol-5-yl)boronic acid. LC-MS calculated for C$_{29}$H$_{29}$D$_3$N$_9$O$_4$(M+H)$^+$: m/z=573.3; found 573.3. $^1$H NMR (600 MHz, DMSO) δ 11.68 (s, 1H), 8.27 (s, 1H), 7.33 (dd, J=8.4, 2.2 Hz, 1H), 7.27 (dd, J=8.3, 2.3 Hz, 1H), 7.12 (dd, J=8.4, 2.6 Hz, 1H), 7.08 (dd, J=8.4, 2.8 Hz, 1H), 6.84 (d, J=6.8 Hz, 1H), 6.81 (s, 1H), 4.16-4.05 (m, 1H), 3.89 (s, 3H), 3.79 (t, J=5.1 Hz, 1H), 3.60 (s, 3H), 3.50 (s, 3H), 3.39 (s, 3H), 2.08 (ddt, J=13.0, 9.0, 4.8 Hz, 1H), 1.92 (s, 1H), 1.86 (dt, J=12.7, 6.5 Hz, 1H), 1.46 (dt, J=11.7, 7.6 Hz, 1H), 1.27 (p, J=11.2 Hz, 1H), 0.75 (m, 1H).

Example 6. Methyl ((1R,3R)-3-(7-(3-fluoro-1-(methyl-d3)-1H-pyrazol-4-yl)-3-(methyl-d3)-8-(1-(methyl-d3)-1H-indazol-5-yl)-2-oxo-3,6-dihydroimidazo[4,5-d]pyrrolo[2,3-b]pyridin-1(2H)-yl)cyclopentyl)carbamate

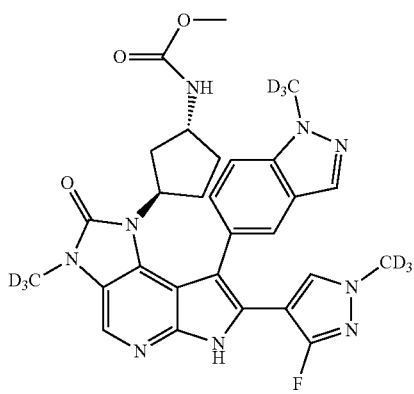 [SMILES: [2H]C([2H])([2H])n1cc(-c2[nH]c3ncc4c(c3c2-c2ccc3c(cnn3C([2H])([2H])[2H])c2)n([C@@H]2CC[C@@H](NC(=O)OC)C2)c(=O)n4C([2H])([2H])[2H])c(F)n1]

Step 1. tert-Butyl ((1R,3R)-3-((5-nitro-1-(phenylsulfonyl)-1H-pyrrolo[2,3-b]pyridin-4-yl)amino)cyclopentyl)carbamate

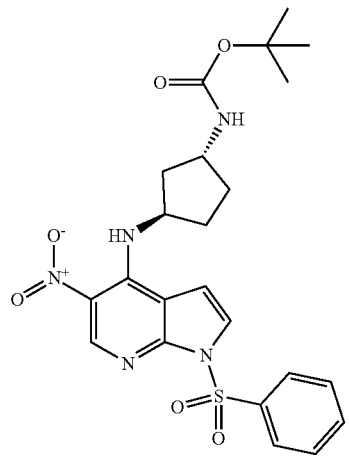 [SMILES: CC(C)(C)OC(=O)N[C@@H]1CC[C@@H](Nc2c([N+](=O)[O-])cnc3c2ccn3S(=O)(=O)c2ccccc2)C1]

A mixture of 4-chloro-5-nitro-1-(phenylsulfonyl)-1H-pyrrolo[2,3-b]pyridine (10.14 g, 30.0 mmol), tert-butyl ((1R,3R)-3-aminocyclopentyl)carbamate (6.30 g, 31.50 mmol) and Et$_3$N (4.18 mL, 64.6 mmol) in iPrOH (100 mL) was stirred at 80° C. for 1 h. The solvent was removed and the residue was washed with water, filtered, and dried to provide the product as a yellow amorphous solid (14.81 g, 29.5 mmol, 98.3%). LC-MS calculated for C$_{23}$H$_{28}$N$_5$O$_6$S (M+H)$^+$: m/z=502.2; found 502.2.

Step 2. tert-Butyl ((1R,3R)-3-((5-amino-1-(phenylsulfonyl)-1H-pyrrolo[2,3-b]pyridin-4-yl)amino)cyclopentyl)carbamate

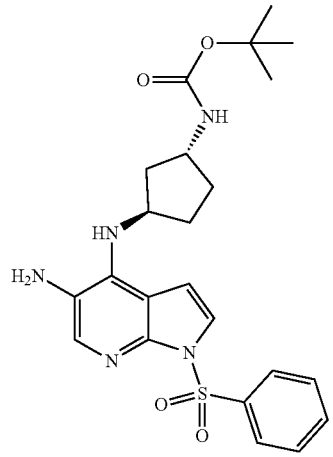 [SMILES: CC(C)(C)OC(=O)N[C@@H]1CC[C@@H](Nc2c(N)cnc3c2ccn3S(=O)(=O)c2ccccc2)C1]

To a solution of tert-butyl ((1R,3R)-3-((5-nitro-1-(phenylsulfonyl)-1H-pyrrolo[2,3-b]pyridin-4-yl)amino)cyclopentyl)carbamate (14.81 g, 29.5 mmol) in THF (200.0 mL)/ethanol (50.0 mL) was added iron (8.38 g, 150 mmol) followed by 1N HCl (20.0 mL) and then the reaction mixture was stirred at 70° C. for 2 h. The mixture was filtered through Celite and washed with ethyl acetate. The organic layer was concentrated and the resulting residue was dissolved in ethyl acetate which was then washed with saturated NaHCO$_3$ solution. The organic solution was concentrated to provide the desired product as a dark yellow amorphous solid (12.02 g, 25.5 mmol, 86.4%). LC-MS calculated for C$_{23}$H$_{30}$N$_5$O$_4$S (M+H)$^+$: m/z=472.2; found 472.3.

Step 3. tert-butyl ((1R,3R)-3-(3-(methyl-d₃)-2-oxo-6-(phenylsulfonyl)-3,6-dihydroimidazo[4,5-d]pyrrolo[2,3-b]pyridin-1(2H)-yl)cyclopentyl)carbamate

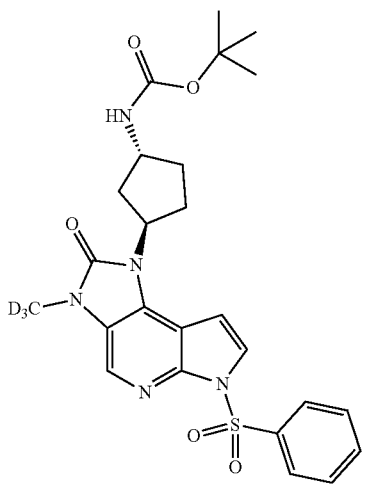 [SMILES: [2H]C([2H])([2H])n1c(=O)n([C@@H]2CC[C@@H](NC(=O)OC(C)(C)C)C2)c2c3ccn(S(=O)(=O)c4ccccc4)c3ncc21]

A mixture of tert-butyl ((1R,3R)-3-((5-amino-1-(phenylsulfonyl)-1H-pyrrolo[2,3-b]pyridin-4-yl)amino)cyclopentyl)carbamate (12.02 g, 25.5 mmol) and carbonyldiimidazole (9.76 g, 80.0 mmol) in MeCN (100 mL) was stirred at 60° C. for 1 h. The solvent was removed and the residue was dissolved in ethyl acetate, and washed sequentially with water, cold 1N HCl, water, and brine. The organic phase was dried and concentrated. The resulting residue was then dissolved in DMF (60.0 mL) before the addition of K₂CO₃ (11.05 g, 80.0 mmol) and CD₃I (11.59 g, 80.0 mmol), and the reaction mixture was then stirred at 50° C. for 2 h. The mixture was diluted with ethyl acetate and washed with water, then the organic phase was dried and concentrated. The residue was purified on silica gel 300 g, 0-100% EtOAc with 5% dichloromethane in hexanes) to provide the desired product as a yellow amorphous solid (9.36 g, 18.2 mmol, 71.4%). LC-MS calculated for $C_{25}H_{27}D_3N_5O_5S$ (M+H)⁺: m/z=515.2; found 515.2.

Step 4. tert-butyl ((1R,3R)-3-(7-bromo-3-(methyl-d₃)-2-oxo-6-(phenylsulfonyl)-3,6-dihydroimidazo[4,5-d]pyrrolo[2,3-b]pyridin-1(2H)-yl)cyclopentyl)carbamate

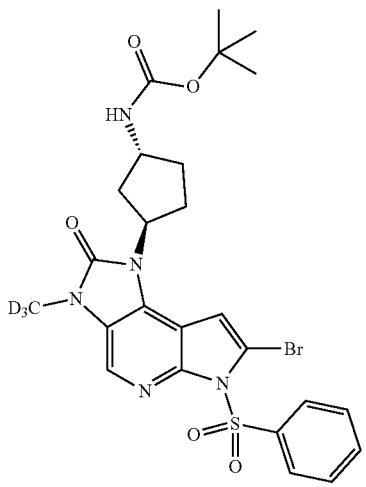 [SMILES: [2H]C([2H])([2H])n1c(=O)n([C@@H]2CC[C@@H](NC(=O)OC(C)(C)C)C2)c2c3cc(Br)n(S(=O)(=O)c4ccccc4)c3ncc21]

Lithium diisopropylamide (LDA, 2.0 M in THF/heptane/ethylbenzene, Sigma-Aldrich) (22.7 mL, 45.5 mmol) was added to a solution of tert-butyl ((1R,3R)-3-(3-(methyl-d₃)-2-oxo-6-(phenylsulfonyl)-3,6-dihydroimidazo[4,5-d]pyrrolo[2,3-b]pyridin-1(2H)-yl)cyclopentyl)carbamate (9.36 g, 18.2 mmol) in THF (200.0 mL) at −78° C. and stirred for 30 min. At this time, 1,2-dibromo-1,1,2,2-tetrachloroethane (7.09 g, 21.8 mmol) in THF (15 mL) was added to the reaction mixture. After stirring for an additional 40 min the reaction was quenched by adding saturated NH₄Cl solution. The mixture was diluted with ethyl acetate and washed with water, and the organic phase was dried and concentrated. The resulting residue was purified on silica gel (120 g, 0-100% EtOAc with 5% dichloromethane in hexanes) to provide the desired product as a yellow amorphous solid (8.90 g, 15.0 mmol. 82.4%). LC-MS calculated for $C_{25}H_{26}D_3BrN_5O_5S$ (M+H)⁺: m/z=593.1, 595.1; found 593.1, 595.1.

Step 5. tert-butyl ((1R,3R)-3-(7-(3-fluoro-1-(methyl-d₃)-1H-pyrazol-4-yl)-3-(methyl-d₃)-2-oxo-6-(phenylsulfonyl)-3,6-dihydroimidazo[4,5-d]pyrrolo[2,3-b]pyridin-1(2H)-yl)cyclopentyl)carbamate

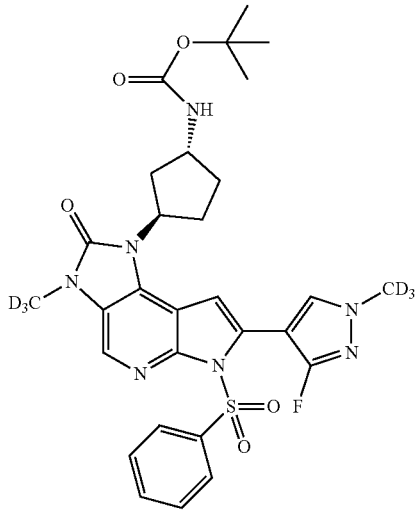 [SMILES: [2H]C([2H])([2H])n1cc(-c2cc3c(ncc4c3n([C@@H]3CC[C@@H](NC(=O)OC(C)(C)C)C3)c(=O)n4C([2H])([2H])[2H])n2S(=O)(=O)c2ccccc2)c(F)n1]

Step 6. 3-Fluoro-1-(methyl-d₃)-4-(4,4,5,5-tetramethyl-1,3,2-dioxaborolan-2-yl)-1H-pyrazole

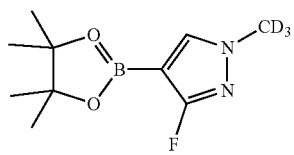

3-Fluoro-4-(4,4,5,5-tetramethyl-1,3,2-dioxaborolan-2-yl)-1H-pyrazole (10.0 g, 47.1 mmol, Pharmablock) was dissolved in THF (200.0 mL) before the addition of K₂CO₃ (11.05 g, 80.0 mmol) and CD₃I (11.59 g, 80.0 mmol), and the reaction mixture was stirred at 40° C. for 2 h. The mixture was diluted with ethyl acetate and washed with water, then the organic phase was dried and concentrated. The residue was purified on silica gel 300 g, 0-100% EtOAc with 5% dichloromethane in hexanes) to provide the desired product as a brown amorphous solid (9.36 g, 18.2 mmol, 71.4%). LC-MS calculated for $C_{10}H_{14}D_3BFN_2O_2$(M+H)⁺: m/z=230.2; found 230.2.

Step 7. tert-Butyl ((1R,3R)-3-(7-(3-fluoro-1-(methyl-d3)-1H-pyrazol-4-yl)-3-(methyl-d3)-2-oxo-6-(phenylsulfonyl)-3,6-dihydroimidazo[4,5-d]pyrrolo[2,3-b]pyridin-1(2H)-yl)cyclopentyl)carbamate

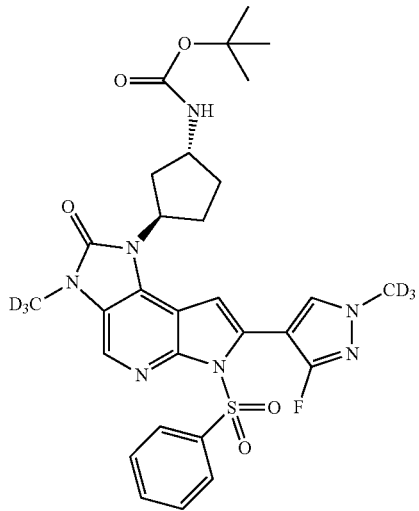 [SMILES: [2H]C([2H])([2H])n1cc(-c2cc3c(ncc4c3n([C@@H]3CC[C@@H](NC(=O)OC(C)(C)C)C3)c(=O)n4C([2H])([2H])[2H])n2S(=O)(=O)c2ccccc2)c(F)n1]

A mixture of tert-butyl ((1R,3R)-3-(7-bromo-3-(methyl-d₃)-2-oxo-6-(phenylsulfonyl)-3,6-dihydroimidazo[4,5-d]pyrrolo[2,3-b]pyridin-1(2H)-yl)cyclopentyl)carbamate (8.90 g, 15.0 mmol), 3-fluoro-1-(methyl-d₃)-4-(4,4,5,5-tetramethyl-1,3,2-dioxaborolan-2-yl)-1H-pyrazole (9.36 g, 18.2 mmol), Cs₂CO₃ (14.7 g, 45.0 mmol) and Pd(Ph₃P)₄ (3.50 g, 3.0 mmol) in dioxane (100.0 mL)/water (20.0 mL) was evacuated and backfilled with nitrogen (this process was repeated a total of three times), and then the reaction was stirred at 105° C. for 3 h. The mixture was diluted with ethyl acetate and washed with water, then the organic phase was dried and concentrated. The residue was purified on silica gel (120 g, 0-100% EtOAc with 5% dichloromethane in hexanes) to provide the desired product as a yellow amorphous solid (5.66 g, 9.2 mmol, 61.3%). LC-MS calculated for $C_{29}H_{27}D_6FN_7O_5S$ (M+H)⁺: m/z=616.3; found 616.2.

Step 8. tert-Butyl ((1R,3R)-3-(8-bromo-7-(3-fluoro-1-(methyl-d₃)-1H-pyrazol-4-yl)-3-(methyl-d₃)-2-oxo-6-(phenylsulfonyl)-3,6-dihydroimidazo[4,5-d]pyrrolo[2,3-b]pyridin-1(2H)-yl)cyclopentyl)carbamate

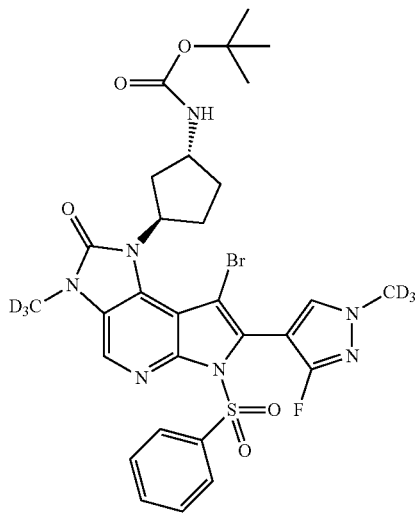 [SMILES: [2H]C([2H])([2H])n1cc(-c2c(Br)c3c(ncc4c3n([C@@H]3CC[C@@H](NC(=O)OC(C)(C)C)C3)c(=O)n4C([2H])([2H])[2H])n2S(=O)(=O)c2ccccc2)c(F)n1]

Bromine (1.61 g, 10.1 mmol) in CH₂Cl₂ (5.0 mL) was added dropwise to a solution of tert-butyl ((1R,3R)-3-(7-(3-fluoro-1-(methyl-d₃)-1H-pyrazol-4-yl)-3-(methyl-d₃)-2-oxo-6-(phenylsulfonyl)-3,6-dihydroimidazo[4,5-d]pyrrolo[2,3-b]pyridin-1(2H)-yl)cyclopentyl)carbamate (5.65 g, 9.2 mmol) in CH₂Cl₂ (80.0 mL) at 0° C. and then stirred for 10 min at the same temperature. The reaction was quenched by adding saturated NaHCO₃, and the resulting mixture was extracted with ethyl acetate. The organic phase was dried and concentrated to provide the desired product as a yellow amorphous solid (6.25 g, 9.0 mmol, 97.8%). LC-MS calculated for $C_{29}H_{26}D_6BrFN_7O_5S$ (M+H)⁺: m/z=694.2, 696.2; found 694.2, 696.2.

Step 9. Methyl ((1R,3R)-3-(8-bromo-7-(3-fluoro-1-(methyl-d₃)-1H-pyrazol-4-yl)-3-(methyl-d₃)-2-oxo-6-(phenylsulfonyl)-3,6-dihydroimidazo[4,5-d]pyrrolo[2,3-b]pyridin-1(2H)-yl)cyclopentyl)carbamate

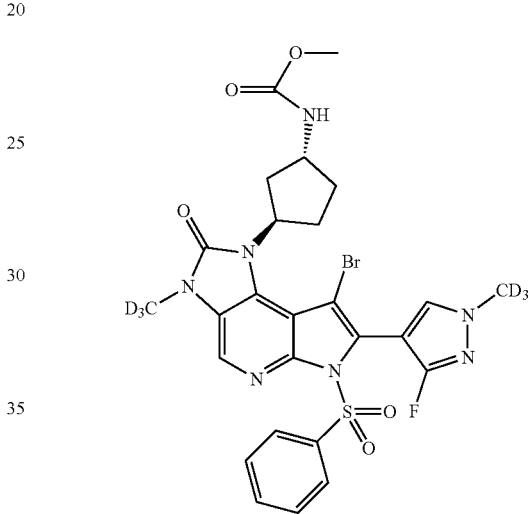

TFA (10 mL) was added to a solution of tert-butyl ((1R,3R)-3-(8-bromo-7-(3-fluoro-1-(methyl-d₃)-1H-pyrazol-4-yl)-3-(methyl-d₃)-2-oxo-6-(phenylsulfonyl)-3,6-dihydroimidazo[4,5-d]pyrrolo[2,3-b]pyridin-1(2H)-yl)cyclopentyl)carbamate (6.25 g, 9.0 mmol) in CH₂Cl₂ (10.0 mL) and then the reaction was stirred at room temperature for 10 min. The mixture was concentrated and then the residue was dissolved in ethyl acetate (40 mL) and water (20.0 mL), followed by the addition of Na₂CO₃ (4.24 g, 40.0 mmol) and methyl chloroformate (0.929 mL, 12.00 mmol) and then stirred at room temperature for 10 min. The mixture was diluted with CH₂Cl₂ and washed with water, then the organic phase was dried and concentrated. The residue was purified on silica gel (120 g, 0-100% EtOAc in CH₂Cl₂) to provide the desired product (5.65 g, 8.7 mmol, 96.2%). LC-MS calculated for $C_{26}H_{20}D_6BrFN_7O_5S$ (M+H)⁺: m/z=652.1, 654.1; found 652.1, 654.1.

Step 10. Methyl ((1R,3R)-3-(7-(3-fluoro-1-(methyl-d₃)-1H-pyrazol-4-yl)-3-(methyl-d₃)-8-(1-(methyl-d₃)-1H-indazol-5-yl)-2-oxo-3,6-dihydroimidazo[4,5-d]pyrrolo[2,3-b]pyridin-1(2H)-yl)cyclopentyl)carbamate A screw-cap vial equipped with a magnetic stir bar was charged with methyl ((1R,3R)-3-(8-bromo-7-(3-fluoro-1-(methyl-d₃)-1H-pyrazol-4-yl)-3-(methyl-d₃)-2-oxo-6-(phenylsulfonyl)-3,6-dihydroimidazo[4,5-d]pyrrolo[2,3-b]pyridin-1(2H)-yl)cyclopentyl)carbamate (15.0 mg, 0.023 mmol), (1-(methyl-d₃)-1H-indazol-5-yl)boronic acid (10.0 mg, 0.056 mmol, Abovchem), Cs₂CO₃ (15.0 mg, 0.046 mmol), Pd(Ph₃P)₄ (7.02 mg, 6.08 μmol) and dioxane (0.8 mL)/water (0.2 mL). The vial was sealed with a Teflon-lined septum, then evacuated and backfilled with nitrogen (this process was repeated a total of three times). The reaction mixture was stirred at 105° C. for 30 min. To this mixture was then added methanol (1.0 mL) and NaOH (4N, 0.20 mL) and the mixture was stirred at 80° C. for an additional 15 min to remove the protecting group. The mixture was diluted with acetonitrile, filtered and then purified using prep-LCMS (XBridge C18 column, eluting with a gradient of acetonitrile/water containing NH₄₀H, at flow rate of 60 mL/min) to give the product as amorphous solid (7.0 mg, 0.012 mmol, 53.7%). LC-MS calculated for C₂₈H₂₀D₉FN₉O₃(M+H)⁺: m/z=567.3; found 567.3. ¹H NMR δ ¹H NMR (600 MHz, DMSO) δ 11.87 (s, 1H), 8.12 (s, 1H), 8.03 (d, J=11.5 Hz, 1H), 7.77-7.65 (m, 2H), 7.46-7.32 (m, 2H), 6.66-6.23 (m, 1H), 3.89 (sext, J=8.1 Hz, 1H), 3.82-3.52 (m, 1H), 3.52-3.41 (m, 3H), 2.14-1.46 (m, 3H), 1.45-0.81 (m, 2H), 0.38--0.22 (m, 1H).

Example 7. Methyl ((1R,3R)-3-(7-(3-fluoro-1-(methyl-d3)-1H-pyrazol-4-yl)-8-(4-fluorophenyl)-3-(methyl-d3)-2-oxo-3,6-dihydroimidazo[4,5-d]pyrrolo[2,3-b]pyridin-1(2H)-yl)cyclopentyl)carbamate

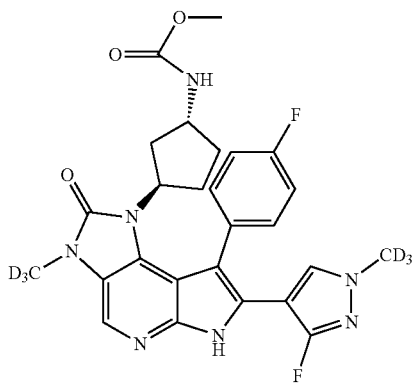 [SMILES: [2H]C([2H])([2H])n1cc(-c2[nH]c3ncc4c(c3c2-c2ccc(F)cc2)n([C@@H]2CC[C@@H](NC(=O)OC)C2)c(=O)n4C([2H])([2H])[2H])c(F)n1]

A screw-cap vial equipped with a magnetic stir bar was charged with methyl ((1R,3R)-3-(8-bromo-7-(3-fluoro-1-(methyl-d₃)-1H-pyrazol-4-yl)-3-(methyl-d₃)-2-oxo-6-(phenylsulfonyl)-3,6-dihydroimidazo[4,5-d]pyrrolo[2,3-b]pyridin-1(2H)-yl)cyclopentyl)carbamate (15.0 mg, 0.023 mmol, Example 6, step 9), 2-(4-fluorophenyl)-4,4,5,5-tetramethyl-1,3,2-dioxaborolane (10.0 mg, 0.042 mmol), Cs₂CO₃ (15.0 mg, 0.046 mmol), Pd(Ph₃P)₄ (7.02 mg, 6.08 μmol) and dioxane (0.8 mL)/water (0.2 mL). The vial was sealed with a Teflon-lined septum, then evacuated and backfilled with nitrogen (this process was repeated a total of three times). The reaction mixture was stirred at 105° C. for 30 min. To this mixture was then added methanol (1.0 mL) and NaOH (4N, 0.20 mL) and the mixture was stirred at 80° C. for an additional 15 min to remove the protecting group. The mixture was diluted with acetonitrile, filtered and then purified using prep-LCMS (XBridge C18 column, eluting with a gradient of acetonitrile/water containing NH₄₀H, at flow rate of 60 mL/min) to give the product as amorphous solid (6.5 mg, 0.012 mmol, 53.6%). LC-MS calculated for C₂₆H₂₀D₆F₂N₇O₃ (M+H)⁺: m/z=528.2; found 528.2. ¹H NMR (600 MHz, DMSO) δ 1H NMR (600 MHz, DMSO) δ 11.93 (s, 1H), 8.13 (d, J=1.0 Hz, 1H), 7.44 (d, J=1.9 Hz, 1H), 7.40 (s, 2H), 7.26 (t, J=8.6 Hz, 2H), 6.91 (d, J=6.7 Hz, 1H), 4.05 (sext, J=7.8 Hz, 1H), 3.88 (s, 1H), 3.50 (s, 3H), 2.06 (ddd, J=13.3, 8.4, 5.1 Hz, 1H), 1.96-1.80 (m, 2H), 1.46 (q, J=9.0 Hz, 1H), 1.33-1.20 (m, 1H), 0.85-0.73 (m, 1H).

Example 8. Methyl ((1R,3R)-3-(8-(1,1-dimethyl-1,3-dihydroisobenzofuran-5-yl)-7-(3-fluoro-1-(methyl-d3)-1H-pyrazol-4-yl)-3-(methyl-d3)-2-oxo-3,6-dihydroimidazo[4,5-d]pyrrolo[2,3-b]pyridin-1(2H)-yl)cyclopentyl)carbamate

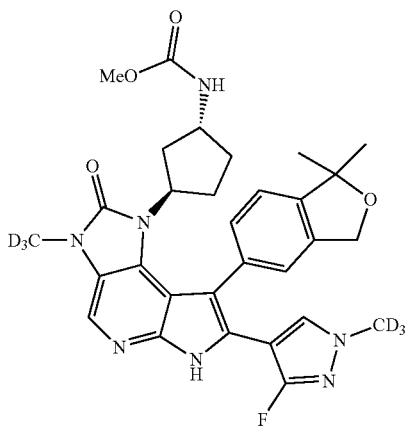 [SMILES: [2H]C([2H])([2H])n1cc(-c2[nH]c3ncc4c(c3c2-c2ccc3c(c2)COC3(C)C)n([C@@H]2CC[C@@H](NC(=O)OC)C2)c(=O)n4C([2H])([2H])[2H])c(F)n1]

A screw-cap vial equipped with a magnetic stir bar was charged with methyl ((1R,3R)-3-(8-bromo-7-(3-fluoro-1-(methyl-d₃)-1H-pyrazol-4-yl)-3-(methyl-d₃)-2-oxo-6-(phenylsulfonyl)-3,6-dihydroimidazo[4,5-d]pyrrolo[2,3-b]pyridin-1(2H)-yl)cyclopentyl)carbamate (15.0 mg, 0.023 mmol, Example 6, step 9), (1,1-dimethyl-1,3-dihydroisobenzofuran-5-yl)boronic acid (10.0 mg, 0.052 mmol, Enamine), Cs₂CO₃ (15.0 mg, 0.046 mmol), Pd(Ph₃P)₄ (7.02 mg, 6.08 μmol) and dioxane (0.8 mL)/water (0.2 mL). The vial was sealed with a Teflon-lined septum, then evacuated and backfilled with nitrogen (this process was repeated a total of three times). The reaction mixture was stirred at 105° C. for 30 min. To this mixture was then added methanol (1.0 mL) and NaOH (4N, 0.20 mL) and the mixture was stirred at 80° C. for an additional 15 min to remove the protecting group. The mixture was diluted with acetonitrile, filtered and then purified using prep-LCMS (XBridge C18 column, eluting with a gradient of acetonitrile/water containing NH₄OH, at flow rate of 60 mL/min) to give the product as amorphous solid (5.5 mg, 0.009 mmol, 41.2%). LC-MS calculated for C₃₀H₂₇D₆FN₇O₄ (M+H)⁺: m/z=580.3; found 580.3. ¹H NMR (600 MHz, DMSO) δ 11.91 (s, 1H), 8.12 (s, 1H), 7.45 (d, J=24.5 Hz, 1H), 7.33-7.20 (m, 3H), 6.97 (s, 0.5H), 6.82 (s, 0.5H), 5.13 (d, J=11.8 Hz, 0.5H), 5.00-4.89 (m, 1.5H), 4.06 (m, 1H), 3.91 (m, 1H), 3.49 (s, 3H), 2.05-1.81 (m, 3H), 1.48 (d, J=5.5 Hz, 6H), 1.38 (m, 1H), 1.21 (m, 1H), 0.66 (m, 1H).

Examples 9-21

Examples 9-21 in Table 2 were prepared according to the procedures described in Example 8, using appropriately substituted starting materials.

TABLE 2

| Ex. No. | Name | Structure | LCMS [M + H]+ | ¹H NMR |
|---|---|---|---|---|
| 9 | Methyl ((1R,3R)-3-(7-(3-fluoro-1-(methyl-d3)-1H-pyrazol-4-yl)-8-(4-(methoxy-d3)phenyl)-3-(methyl-d3)-2-oxo-3,6-dihydroimidazo[4,5-d]pyrrolo[2,3-b]pyridin-1(2H)-yl)cyclopentyl)carbamate | 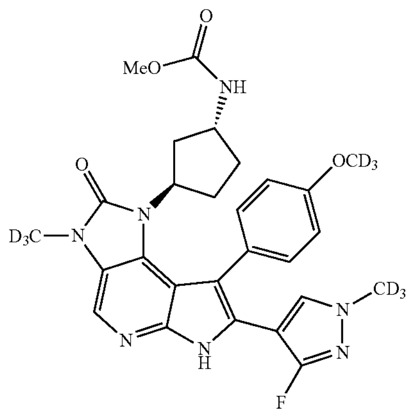 | 543.3 | ¹H NMR (600 MHz, DMSO-d₆) δ 11.83 (s, 1H), 8.11 (s, 1H), 7.39 (s, 1H), 7.32-7.22 (m, 2H), 7.06-6.97 (m, 2H), 6.83 (d, J = 5.8 Hz, 1H), 4.05 (m, 1H), 3.91 (m, 1H), 3.50 (s, 3H), 2.05 (m, 1H), 1.91 (m, 1H), 1.84 (m, 1H), 1.46 (m, 1H), 1.27 (m, 1H), 0.73 (m, 1H). |
| 10 | Methyl ((1R,3R)-3-(7-(3-fluoro-1-(methyl-d3)-1H-pyrazol-4-yl)-8-(4-(2-hydroxypropan-2-yl)phenyl)-3-(methyl-d3)-2-oxo-3,6-dihydroimidazo[4,5-d]pyrrolo[2,3-b]pyridin-1(2H)-yl)cyclopentyl)carbamate | 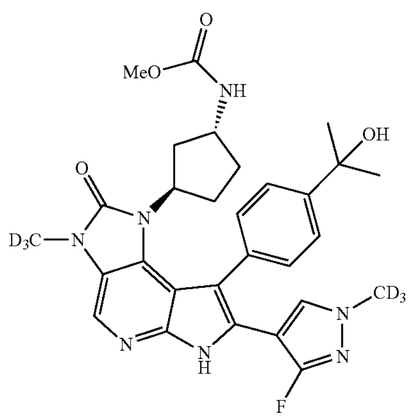 [SMILES: [2H]C([2H])([2H])n1cc(-c2[nH]c3ncc4c(c3c2-c2ccc(C(C)(C)O)cc2)n([C@@H]2CC[C@@H](NC(=O)OC)C2)c(=O)n4C([2H])([2H])[2H])c(F)n1] | 568.3 | ¹H NMR (600 MHz, DMSO-d₆) δ 11.88 (s, 1H), 8.11 (s, 1H), 7.60-7.47 (m, 2H), 7.43 (s, 1H), 7.39 (s, 1H), 7.35-7.21 (m, 2H), 6.75 (d, J = 6.9 Hz, 1H), 5.05 (s, 1H), 4.05 (m, 1H), 3.87 (m, 1H), 3.49 (s, 3H), 2.03 (m, 1H), 1.51 (d, J = 15.8 Hz, 6H), 1.38 (m, 1H), 1.18 (m, 1H), 0.69 (m, 1H). |
| 11 | Methyl ((1R,3R)-3-(8-(1,1-dimethyl-1,3-dihydroisobenzofuran-5-yl)-7-(3-fluoro-1-(methyl-d3)-1H-pyrazol-4-yl)-3-methyl-2-oxo-3,6-dihydroimidazo[4,5-d]pyrrolo[2,3-b]pyridin-1(2H)-yl)cyclopentyl)carbamate | 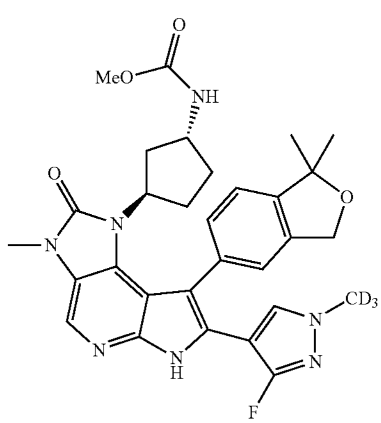 [SMILES: [2H]C([2H])([2H])n1cc(-c2[nH]c3ncc4c(c3c2-c2ccc3c(c2)COC3(C)C)n([C@@H]2CC[C@@H](NC(=O)OC)C2)c(=O)n4C)c(F)n1] | 577.3 | ¹H NMR (600 MHz, DMSO-d₆) δ 12.19 (s, 1H), 8.21 (s, 1H), 7.44 (d, J = 24.5 Hz, 1H), 7.33-7.20 (m, 3H), 6.97 (s, 0.5H), 6.81 (s, 0.5H), 5.13 (d, J = 11.8 Hz, 0.5H), 5.00-4.89 (m, 1.5H), 4.07 (m, 1H), 3.95 (m, 1H), 3.49 (s, 3H), 3.22 (s, 3H), 2.07-1.79 (m, 3H), 1.49 (d, J = 5.5 Hz, 6H), 1.38 (m, 1H), 1.21 (m, 1H), 0.66 (m, 1H). |

TABLE 2-continued

| Ex. No. | Name | Structure | LCMS [M + H]+ | 1H NMR |
|---|---|---|---|---|
| 12 | Methyl ((1R,3R)-3-(7-(1-(2,2-difluoroethyl)-3-fluoro-1H-pyrazol-4-yl)-8-(1,1-dimethyl-1,3-dihydroisobenzofuran-5-yl)-3-(methyl-d3)-2-oxo-3,6-dihydroimidazo[4,5-d]pyrrolo[2,3-b]pyridin-1(2H)-yl)cyclopentyl)carbamate | 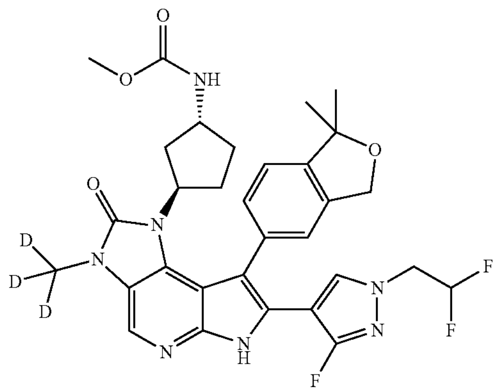 [SMILES: [2H]C([2H])([2H])n1c(=O)n([C@@H]2CC[C@@H](NC(=O)OC)C2)c2c3c(-c4ccc5c(c4)COC5(C)C)c(-c4cn(CC(F)F)nc4F)[nH]c3ncc21] | 627.3 | 1H NMR (600 MHz, DMSO) δ 12.20 (s, 1H), 8.21 (s, 1H), 7.42 (m, 1H), 7.35-7.21 (m, 3H), 6.90 (m, 1H), 6.26 (m, 1H), 5.16-4.91 (m, 2H), 4.47 (dd, J = 16.8, 13.3 Hz, 2H), 4.04 (m, 2H), 3.49 (s, 3H), 2.05 (m, 1H), 1.88 (m, 2H), 1.52-1.44 (m, 6H), 1.415 (m, 1H), 1.23 (q, J = 11.5 Hz, 1H), 0.65 (m, 1H). |
| 13 | Methyl ((1R,3R)-3-(7-(3-fluoro-1-(methyl-d3)-1H-pyrazol-4-yl)-8-(1-isopropyl-1H-indazol-5-yl)-3-(methyl-d3)-2-oxo-3,6-dihydroimidazo[4,5-d]pyrrolo[2,3-b]pyridin-1(2H)-yl)cyclopentyl)carbamate | 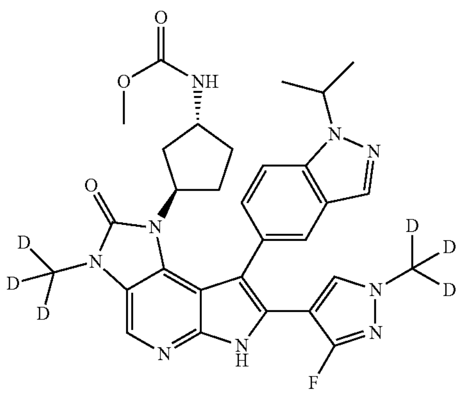 [SMILES: [2H]C([2H])([2H])n1cc(-c2[nH]c3ncc4c(c3c2-c2ccc3c(cnn3C(C)C)c2)n([C@@H]2CC[C@@H](NC(=O)OC)C2)c(=O)n4C([2H])([2H])[2H])c(F)n1] | 592.3 | 1H NMR (600 MHz, DMSO-d6) δ 12.09 (s, 1H), 8.19 (s, 1H), 8.10 (s, 0.4H), 8.06 (s, 0.6H), 7.76 (m, 1H), 7.75 (s, 0.4H), 7.72 (s, 0.6H), 7.49 (s, 1H), 7.38 (d, J = 8.6 Hz, 0.6H), 7.32 (d, J = 8.6 Hz, 0.4H), 6.67 (brs, 0.6H), 6.27 (brs, 0.4H), 5.03 (m, 1H), 3.79-3.53 (m, 2H), 3.47 (s, 1.8H), 3.44 (s, 1.2H), 2.00 (m, 0.6H), 1.95-1.86 (m, 0.8H), 1.80-1.65 (m, 1H), 1.60-1.41 (m, 6.6H), 1.35 (m, 0.4H), 1.19 (m, 0.6H), 1.06 (m, 0.6H), 0.93 (m, 0.4H), 0.11 (m, 0.4H), −0.25 (m, 0.6H) |
| 14 | Methyl ((1R,3R)-3-(8-(1-(2,2-difluoroethyl)-1H-indazol-5-yl)-7-(3-fluoro-1-(methyl-d3)-1H-pyrazol-4-yl)-3-(methyl-d3)-2-oxo-3,6-dihydroimidazo[4,5-d]pyrrolo[2,3-b]pyridin-1(2H)-yl)cyclopentyl)carbamate | 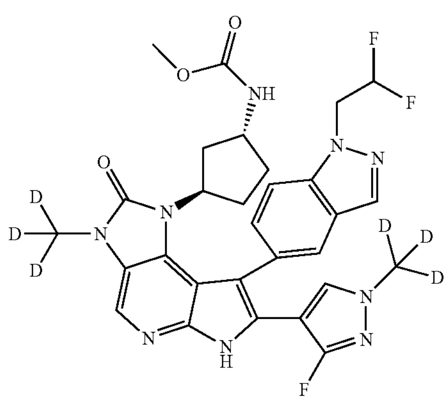 [SMILES: [2H]C([2H])([2H])n1cc(-c2[nH]c3ncc4c(c3c2-c2ccc3c(cnn3CC(F)F)c2)n([C@@H]2CC[C@@H](NC(=O)OC)C2)c(=O)n4C([2H])([2H])[2H])c(F)n1] | 614.3 | 1H NMR (600 MHz, DMSO-d6) δ 12.10 (s, 1H), 8.21-8.15 (m, 2H), 7.85-7.76 (m, 2H), 7.51-7.38 (m, 2H), 6.61-6.23 (m, 2H), 4.99 (m, 2H), 3.93-3.77 (1.6 H), 3.57-3.41 (m, 3.4H), 2.00 (m, 0.6H), 1.95-1.86 (m, 0.8), 1.79-164 (m, 1H), 1.52 (m, 0.6H), 1.38 (m, 0.4H), 1.18-1.05 (m, 1.2H), 0.90 (m, 0.4H), 0.26 (m, 0.4H), −0.18 (m, 0.6H) |

TABLE 2-continued

| Ex. No. | Name | Structure | LCMS [M + H]+ | 1H NMR |
|---|---|---|---|---|
| 15 | Methyl ((1R,3R)-3-(7-(1-(ethyl-d5)-3-fluoro-1H-pyrazol-4-yl)-3-(methyl-d3)-8-(1-(methyl-d3)-1H-indazol-5-yl)-2-oxo-3,6-dihydroimidazo[4,5-d]pyrrolo[2,3-b]pyridin-1(2H)-yl)cyclopentyl)carbamate | 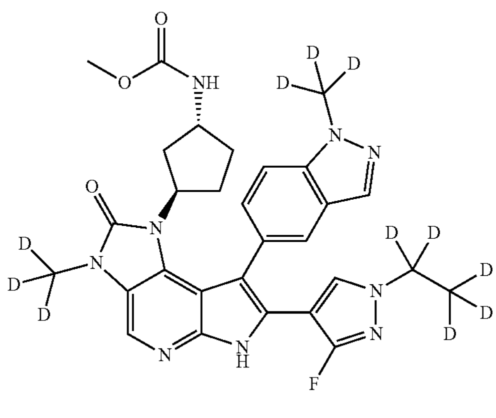 [SMILES: [2H]C([2H])([2H])n1ncc2cc(-c3c(-c4cn(C([2H])([2H])C([2H])([2H])[2H])nc4F)[nH]c4ncc5c(c34)n([C@@H]3CC[C@@H](NC(=O)OC)C3)c(=O)n5C([2H])([2H])[2H])ccc21] | 583.3 | 1H NMR (600 MHz, DMSO) δ 12.29 (s, 1H), 8.24 (s, 1H), 8.07-8.01 (m, 1H), 7.77-7.68 (m, 2H), 7.48 (d, J = 2.0 Hz, 0.6H), 7.44 (d, J = 2.0 Hz, 0.4H), 7.38 (m, 1H), 6.66 (d, J = 6.8 Hz, 0.6H), 6.32 (d, J = 6.0 Hz, 0.4H), 4.00-3.78 (m, 1.4H), 3.59 (qd, J = 8.8, 5.2 Hz, 0.6H), 3.52-3.39 (m, 3H), 2.03 (dt, J = 13.4, 7.0 Hz, 0.6H), 1.96 (m, 0.4H), 1.86 (m, 0.4H), 1.79-1.66 (m, 1H), 1.53 (dt, J = 12.5, 6.5 Hz, 0.6H), 1.45 (m, 0.4H), 1.21-1.05 (m, 1.2H), 0.86 (m, 0.4H), 0.35 (m, 0.4H), −0.15 (m, 0.6H). |
| 16 | Methyl ((1R,3R)-3-(7-(3-fluoro-1-(methyl-d3)-1H-pyrazol-4-yl)-8-(1-isopropyl-1H-indazol-5-yl)-3-methyl-2-oxo-3,6-dihydroimidazo[4,5-d]pyrrolo[2,3-b]pyridin-1(2H)-yl)cyclopentyl)carbamate | 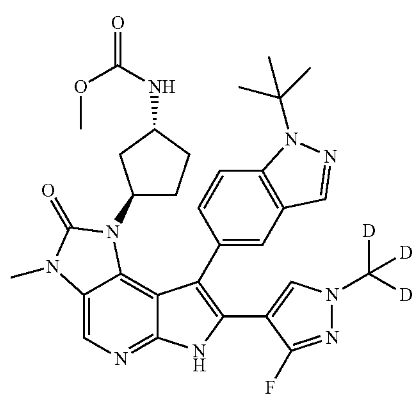 [SMILES: [2H]C([2H])([2H])n1cc(-c2[nH]c3ncc4c(c3c2-c2ccc3c(cnn3C(C)(C)C)c2)n([C@@H]2CC[C@@H](NC(=O)OC)C2)c(=O)n4C)c(F)n1] | 589.3 | |
| 17 | Methyl ((1R,3R)-3-(8-(7-fluoro-1-(methyl-d3)-1H-indazol-5-yl)-7-(3-fluoro-1-(methyl-d3)-1H-pyrazol-4-yl)-3-(methyl-d3)-2-oxo-3,6-dihydroimidazo[4,5-d]pyrrolo[2,3-b]pyridin-1(2H)-yl)cyclopentyl)carbamate | 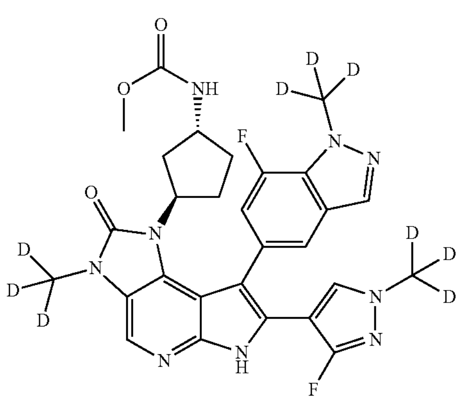 [SMILES: [2H]C([2H])([2H])n1cc(-c2[nH]c3ncc4c(c3c2-c2cc(F)c3c(cnn3C([2H])([2H])[2H])c2)n([C@@H]2CC[C@@H](NC(=O)OC)C2)c(=O)n4C([2H])([2H])[2H])c(F)n1] | 585.3 | 1H NMR (600 MHz, DMSO-d6) δ 12.32 (s, 1H), 8.25 (s, 1H), 8.12 (s, 1H), 7.61 (s, 0.6H), 7.58 (s, 0.4H), 7.49 (s, 1H), 7.27 (d, J = 12.4 Hz, 0.4H), 7.22 (d, J = 12.3 Hz, 0.6H), 6.79 (m, 0.6H), 6.51 (m, 0.4H), 3.92 (m, 1H), 3.84 (m, 0.4H), 3.70 (m, 0.6H), 3.49 (s, 1.8H), 3.44 (s, 1.2H), 2.08 (m, 1H), 2.00 (m, 0.6H), 1.93 (m, 0.4H), 1.77 (m, 1H), 1.59 (m, 0.6H), 1.53 (m, 0.4H), 1.24 (m, |

TABLE 2-continued

| Ex. No. | Name | Structure | LCMS [M + H]+ | 1H NMR |
|---|---|---|---|---|
| | | | | 1.6H), 0.92 (m, 0.4H), 0.48 (m, 0.4H), 0.09 (m, 0.6H). |
| 18 | Methyl ((1R,3R)-3-(8-(1-(2,2-difluoroethyl)-1H-indazol-5-yl)-7-(3-fluoro-1-(methyl-d3)-1H-pyrazol-4-yl)-3-methyl-2-oxo-3,6-dihydroimidazo[4,5-d]pyrrolo[2,3-b]pyridin-1(2H)-yl)cyclopentyl)carbamate | 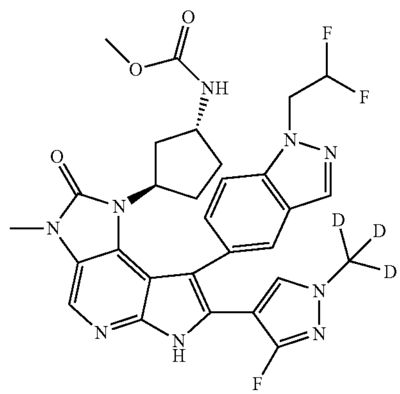 [SMILES: [2H]C([2H])([2H])n1cc(-c2[nH]c3ncc4c(c3c2-c2ccc3c(cnn3CC(F)F)c2)n([C@@H]2CC[C@@H](NC(=O)OC)C2)c(=O)n4C)c(F)n1] | 611.3 | |
| 19 | Methyl ((1R,3R)-3-(8-(1,1-dimethyl-1,3-dihydro-isobenzofuran-5-yl)-7-(1-(ethyl-d5)-3-fluoro-1H-pyrazol-4-yl)-3-(methyl-d3)-2-oxo-3,6-dihydroimidazo[4,5-d]pyrrolo[2,3-b]pyridin-1(2H)-yl)cyclopentyl)carbamate | 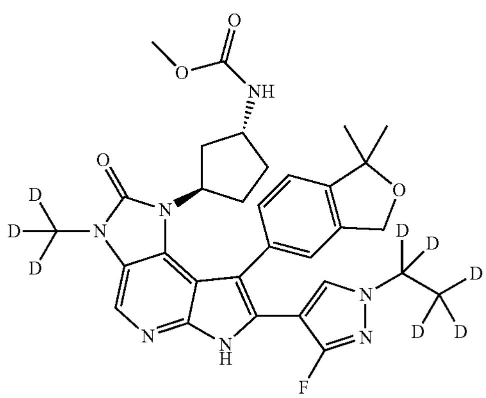 [SMILES: [2H]C([2H])([2H])n1c(=O)n([C@@H]2CC[C@@H](NC(=O)OC)C2)c2c3c(-c4ccc5c(c4)COC5(C)C)c(-c4cn(C([2H])([2H])C([2H])([2H])[2H])nc4F)[nH]c3ncc21] | 596.3 | |
| 20 | Methyl ((1R,3R)-3-(8-(1,1-dimethyl-1,3-dihydro-isobenzofuran-5-yl)-7-(1-ethyl-3-fluoro-1H-pyrazol-4-yl)-3-(methyl-d3)-2-oxo-3,6-dihydroimidazo[4,5-d]pyrrolo[2,3-b]pyridin-1(2H)-yl)cyclopentyl)carbamate | 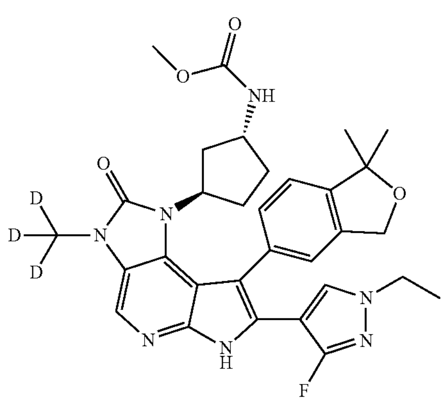 [SMILES: [2H]C([2H])([2H])n1c(=O)n([C@@H]2CC[C@@H](NC(=O)OC)C2)c2c3c(-c4ccc5c(c4)COC5(C)C)c(-c4cn(CC)nc4F)[nH]c3ncc21] | 591.3 | |

TABLE 2-continued

| Ex. No. | Name | Structure | LCMS [M + H]+ | 1H NMR |
|---|---|---|---|---|
| 21 | Methyl ((1R,3R)-3-(7-(3-fluoro-1-(propan-2-yl-d7)-1H-pyrazol-4-yl)-3-(methyl-d3)-8-(1-(methyl-d3)-1H-indazol-5-yl)-2-oxo-3,6-dihydroimidazo[4,5-d]pyrrolo[2,3-b]pyridin-1(2H)-yl)cyclopentyl)carbamate | 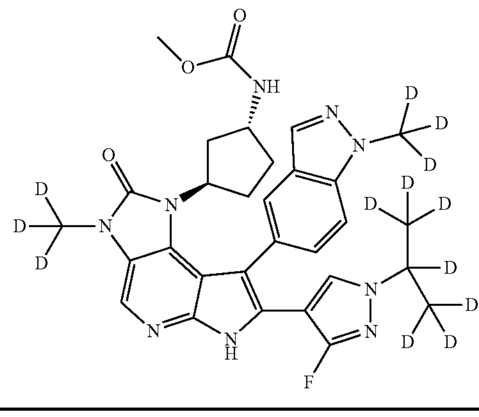 | 599.3 | |

Example A. JAK2 LanthaScreen JH1 Binding Assay

JAK2 JH1 binding assay utilizes catalytic domain (JH1, amino acids 826-1132) of human JAK2 expressed as N-terminal FLAG-tagged, biotinylated protein in a baculovirus expression system (Carna Biosciences, Product #08-445-20N). The assay was conducted in black 384-well polystyrene plates in a final reaction volume of 20 μL. JAK2 JH1 (1.5 nM) was incubated with compounds (100 nL serially diluted in DMSO) in the presence of 50 nM fluorescent JAK2-JH1 tracer and 0.5 nM Streptavidin-Tb cryptate (Cisbio Part #610SATLB) in assay buffer (50 mM Tris, pH=7.5, 10 mM MgCl$_2$, 0.01% Brij-35, 0.1% BSA, 1 mM EGTA, 5% Glycerol and 5 mM DTT). Non-specific binding was accessed in the presence of 2 mM ATP. After incubation for 2 hours at 25° C., LanthaScreen signals were read on a PHERAstar FS plate reader (BMG LABTECH). Data was analyzed with IDBS XLfit and GraphPad Prism 5.0 software using a four parameter dose response curve to determine IC50 for each compound.

Example B. JAK2 LanthaScreen JH2-V617F Binding Assay

JAK2 JH2-V617F binding assay utilizes pseudo-kinase domain (JH2, amino-acids 536-812 with 3 surface mutations W659A, W777A, F794H) of human V617F mutant JAK2 expressed as C-terminal His-Avi-tagged, biotinylated protein in a baculovirus expression system (BPS Bioscience, Catalog #79498). The assay was conducted in black 384-well polystyrene plates in a final reaction volume of 20 μL. JAK2 JH2-V617F (0.26 nM) was incubated with compounds (100 nL serially diluted in DMSO) in the presence of 50 nM Fluorescent JAK2-JH2 Tracer (MedChem Express Catalog #HY-102055) and 0.25 nM Streptavidin-Tb cryptate (Cisbio Part #610SATLB) in assay buffer (50 mM Tris, pH=7.5, 10 mM MgCl$_2$, 0.01% Brij-35, 0.1% BSA, 1 mM EGTA, 5% Glycerol and 5 mM DTT). Non-specific binding was accessed in the presence of 2 mM ATP. After incubation for 1 hour at 25° C., LanthaScreen signals were read on a PHERAstar FS plate reader (BMG LABTECH). Data was analyzed with IDBS XLfit and GraphPad Prism 5.0 software using a four parameter dose response curve to determine IC50 for each compound.

Example C. FLT3 Enzymatic Assay

The kinase assays were carried out at room temperature in assay buffer (HEPES 50 mM, pH 7.0, NaN$_3$ 0.02%, BSA 0.01%, Orthovanadate 0.1 mM, DTT 1 mM, MgCl$_2$ 10 mM) in a final volume of 10 μL. Testing compounds were prepared by serial dilution in DMSO and transferred to the plate wells by ECHO liquid handler (Labcyte) with 0.5% DMSO in the final assay. The FLT3/TK Substrate-biotin mixture is prepared in the assay buffer with 1000 nM TK Substrate-biotin and SEB reagent 125 nM. 5 μL mixture was added to polystyrene 384-well small volume black plate (Greiner Bio-One). Reactions were initiated by the addition of 5 μL ATP in assay buffer. The final 10 μL kinase reaction consists of 0.011 nM FLT3, 1 mM ATP, 500 nM TK Substrate-biotin and SEB reagent 62.5 nM in assay buffer. Reactions were incubated for 90 min and terminated by addition of 10 μL of detection reagent containing 125 nM Streptavidin-XL665, TK Antibody-Cryptate in HTRF® Detection buffer (HEPES 50 mM, pH 7.0, BSA 0.1%, KF 0.8 M, EDTA 20 mM). The plates were then sealed and centrifuged at 1800 rpm for 2 minutes. After 60 minutes incubation at room temperature, the product activity was determined by measuring the fluorescence at 620 nm and 665 nm on Pherastar microplate reader (BMG Labtech). A ratio is calculated (665/620 nm) for each well. Wells with DMSO only were served as the positive controls and wells containing no ATP were used as negative controls. IC$_{50}$ determination was performed by fitting the curve of percent control activity versus the log of the compound concentration using the GraphPad Prism 7.0 software.

Example D. KIT Enzymatic Assay

The kinase assays were carried out at room temperature in assay buffer (HEPES 50 mM, pH 7.0, NaN$_3$ 0.02%, BSA 0.01%, Orthovanadate 0.1 mM, DTT 1 mM, MgCl$_2$ 10 mM) in a final volume of 10 μL. Testing compounds were prepared by serial dilution in DMSO and transferred to the plate wells by ECHO liquid handler (Labcyte) with 0.5% DMSO in the final assay. The KIT/TK Substrate-biotin mixture is prepared in the assay buffer with 1000 nM TK Substrate-biotin and SEB reagent 125 nM. 5 μL mixture was added to polystyrene 384-well small volume black plate (Greiner Bio-One). Reactions were initiated by the addition of 5 μL ATP in assay buffer. The final 10 μL kinase reaction consists of 0.12 nM KIT, 1 mM ATP, 500 nM TK Substrate-biotin and SEB reagent 62.5 nM in assay buffer. Reactions were incubated for 90 min and terminated by addition of 10 μL of detection reagent containing 125 nM Streptavidin-XL665, TK Antibody-Cryptate in HTRF® Detection buffer (HEPES 50 mM, pH 7.0, BSA 0.1%, KF 0.8 M, EDTA 20 mM). The plates were then sealed and centrifuged at 1800 rpm for 2 minutes. After 60 minutes incubation at room temperature, the product activity was determined by measuring the fluorescence at 620 nm and 665 nm on Pherastar microplate reader (BMG Labtech). A ratio is calculated (665/620 nm) for each well. Wells with DMSO only were served as the positive controls and wells containing no ATP were used as negative controls. $IC_{50}$ determination was performed by fitting the curve of percent control activity versus the log of the compound concentration using the GraphPad Prism 7.0 software.

The compounds of the disclosure and comparative examples were tested in one or more of the assays described in Examples A-D, and the resulting data are shown in Table A. Selectivity against tyrosine kinases such as FLT3 and KIT are desirable. Clinical studies have shown that inhibitors of KIT and FLT3 are myelosuppressive, most likely due to the roles that these kinases play in the hematopoietic system. Both KIT and FLT3 are expressed predominantly in hematopoietic stem and progenitor cells. Murine genetic models have shown that KIT is essential for hematopoiesis due to the reliance on hematopoietic stem cells on KIT for survival. Likewise mouse genetic studies have shown that FLT3 knockout mice have deficiencies in abilities to repopulate B and T cells. Combined knockout of KIT and FLT3 results in lethality in mice. The compounds of the current disclosure exhibited greater selectivity against receptor tyrosine kinases such as FLT3 and KIT when compared with the comparative examples. Without being bound by theory, it is believed that Comparative Example D would exhibit FLT3 and KIT IC50s similar to Comparative Examples A, B, C, and E.

TABLE A

| Example No. | JH2 V617F Bind $IC_{50}$ (nM) | JH1 Bind $IC_{50}$ (nM) | FLT3 $IC_{50}$ (nM) | KIT $IC_{50}$ (nM) | Selectivity FLT3/ JH2 V617F | Selectivity KIT/ JH2 V617F |
|---|---|---|---|---|---|---|
| Comparative Example A | + | +++++ | ††† | ††† | * | * |
| Comparative Example B | + | +++++ | ††† | †††† | * | ** |
| Comparative Example C | + | ++ | † | †† | * | * |
| Comparative Example D | + | +++ | NT | NT | NT | NT |
| Comparative Example E | + | +++++ | ††† | †††† | * | *** |
| 1 | + | +++++ | ††††† | ††††† | **** | ***** |
| 2 | + | +++++ | ††††† | ††††† | **** | **** |
| 3 | + | +++++ | ††††† | †††† | **** | **** |
| 4 | + | +++++ | ††††† | ††††† | ***** | ****** |
| 5 | + | +++++ | †††† | ††††† | ***** | ****** |
| 6 | + | +++++ | †††† | ††† | ***** | **** |
| 7 | + | +++++ | ††††† | ††† | **** | ** |
| 8 | + | +++++ | ††††† | †††† | ****** | ****** |
| 9 | + | +++++ | ††† | ††† | ***** | *** |
| 10 | + | +++++ | ††† | ††† | **** | *** |
| 11 | + | +++++ | ††††† | ††††† | ****** | ****** |
| 12 | + | +++++ | ††††† | ††††† | ****** | ****** |
| 13 | + | +++++ | ††††† | ††† | ****** | **** |
| 14 | + | +++++ | †††† | ††† | ****** | ***** |
| 15 | + | +++++ | ††† | ††† | ***** | **** |
| 16 | + | +++++ | †††† | †††† | ***** | ****** |
| 17 | + | +++++ | †††† | †††† | ****** | ****** |
| 18 | + | +++++ | ††† | †††† | ****** | ****** |
| 19 | + | +++++ | ††††† | ††††† | ****** | ****** |
| 20 | + | +++++ | ††††† | ††††† | ****** | ****** |
| 21 | + | +++++ | †††† | †††† | ****** | ****** |

NT refers to "not tested"
+ refers to $IC_{50}$ of ≤10 nM
++ refers to $IC_{50}$ of >10 nM to ≤100 nM
+++ refers to $IC_{50}$ of >100 nM to ≤500 nM
++++ refers to $IC_{50}$ of >500 nM to ≤1000 nM
+++++ refers to $IC_{50}$ of >1000 nM
† refers to $IC_{50}$ of ≤25 nM
†† refers to $IC_{50}$ of >25 nM to ≤250 nM
††† refers to $IC_{50}$ of >250 nM to ≤1250 nM
†††† refers to $IC_{50}$ of >1250 nM to ≤2500 nM
††††† refers to $IC_{50}$ of >2500 nM
* refers to selectivity of ≤500-fold
** refers to selectivity of >500-fold to ≤1500-fold
*** refers to selectivity of >1500-fold to ≤1750-fold
**** refers to selectivity of >1750-fold to ≤5000-fold
***** refers to selectivity of >5000-fold to ≤12500-fold
****** refers to selectivity of >12500-fold Example E. STAT5 (Tyr694) Phosphorylation Cell Based Assay SET-2 cells was purchased from DSMZ (Germany). RPMI1640 medium, Fetal Bovine Serum and 384-white sold flat-bottom small volume plate were purchased from Thermo Fisher Scientific (Waltham, MA). Phospho-STAT5 (Tyr694) HTRF kit was purchased from Perkin Elmer (Waltham, MA).

SET-2 cells were cultured in RPMI media with 20% FBS at 37° C. in humidified incubator supplied with 5% $CO_2$. On the day of assay, the cells were centrifuged to remove the culture media and resuspended with prewarmed RPMI with 10% FBS. Testing compounds were prepared by serial dilution in DMSO and 50 nL/well test compounds were transferred to the 384 white low volume cell culture plate (Greiner Bio-one) by ECHO liquid handler (Labcyte). The cells were then dispensed with Multidrop (Thermo Fisher, Waltham, MA) at 10 μL/well (7×10$^6$ cells/mL) with 0.5% DMSO in the final assay. After the treated cells were incubated for 2 hours at 37° C./5% $CO_2$ incubator, 4 μL/well supplemented lysis buffer (100× blocking buffer diluted 25 fold in 4× lysis buffer, Perkin Elmer) were added and incubated at room temperature for 90 min on orbital shaker at 600 rpm. Phospho-STAT5 Cryptate antibody and Phospho-STAT5 d2 antibody (1:1 vol/vol) were premixed and diluted 20 fold with in the detection buffer (Perkin Elmer). 4 μL of the premixed antibody solution were added to each well followed with 24 hours incubation at room temperature on orbital shaker at 600 rpm. The product activity was determined by measuring the fluorescence at 620 nm and 665 nm on Pherastar microplate reader (BMG Labtech). A ratio is calculated (665/620) for each well. Wells with DMSO only served as the positive controls and wells containing high concentration of control compound were used as negative controls. $IC_{50}$ determination was performed by fitting the curve of percent control activity versus the log of the compound concentration using the GraphPad Prism 7.0 software.

Example F. pSTAT5 SET-2 Whole Blood MSD Assay

SET-2 cells shipped from ABS, RPMI1640 medium, Fetal Bovine Serum from Gibco, Phospho-STAT5a,b Whole Cell Lysate Kit from Mesoscale, Retronectin (Recombinant Human Fibronectin Fragment) from TaKaRa, 96 well cell culture plate flat bottom from Corning, lysis buffer from Cell Signaling Technology, and sterile PBS from Gibco. Whole Blood from by BioIVT.

SET-2 cells were cultured in RPMI media with 20% FBS at 37° C. humidified incubator supplied with 5% $CO_2$. On the day of the assay, 40 uL per well of diluted retronectin working solution was added to sterile 96-well clear flat bottom tissue culture plates (1:200 dilution of retronectin in sterile PBS) and incubated at 37 C for 1 hour. After 1 hour, the retronectin working solution was aspirated and SET-2 cells were seeded at 100,000/well in RPMI+20% FBS. Cells were incubated overnight at 37° C. and 5% $CO_2$. The next day, the medium was removed and 40 µL of diluted compounds in serum-free RPMI and whole blood was added to the cells for a 2 hour incubation at 37° C. and 5% $CO_2$. The compound starting concentration is 20 µM and 2.5 fold serial diluted down to 0.21 nM. The whole blood and compound mixture was then aspirated off using the BlueCat plate washer and washed 1× with PBS. Cells were lysed by adding 40 µL of 3× complete lysis buffer and shaken at room temperature for 45-60 minutes (complete lysis buffer consists of Cell Signaling Technology lysis buffer diluted to 3× and supplemented with Mesoscale's protease inhibitor, phosphatase I inhibitor, and phosphatase II inhibitor). The pSTAT5 MSD plates were blocked by adding 150 µL of Blocker A solution per well to the MSD plates and incubated at room temperature with shaking at 400 rpm for one hour or longer. After blocking, plates were washed 3× with 300 µL/well of lX Tris Wash Buffer. After lysis, added 25 µL per well of lysed sample was added to MSD plate and incubated with shaking at 4° C. wrapped in foil overnight. The next day, plates were washed again and 25 µL/well of diluted 1× Detection Antibody Solution, wrapped in foil, and incubated at room temperature with shaking at 400 rpm for 1 hour. Plates were then washed again and lastly, 150 µL/well of 1× Read Buffer T was added to all wells. Plates were analyzed on MSD Discovery within 5 minutes. Inhibition of pSTAT5 signaling was calculated against a control as inhibitory concentration for 50% inhibition ($IC_{50}$). Data analysis was performed in GraphPad Prism using a 4-parameter fit and data was reported as Average±SD.

Example G. In Vitro Intrinsic Clearance Protocol

For in vitro metabolic stability experiments, test compounds were incubated with human liver microsomes at 37° C. The incubation mixture contained test compounds (1 µM), NADPH (2 mM), and human liver microsomes (0.5 mg protein/mL) in 100 mM phosphate buffer (pH 7.4). The mixture was pre-incubated for 2 min at 37° C. before the addition of NADPH. Reactions were commenced upon the addition of NADPH and quenched with ice-cold methanol at 0, 10, 20, and 30 min. Terminated incubation mixtures were analyzed using LC-MS/MS system. The analytical system consisted of a Shimadzu LC-30AD binary pump system and SIL-30AC autosampler (Shimadzu Scientific Instruments, Columbia, MD) coupled with a Sciex Triple Quad 6500+ mass spectrometer from Applied Biosystems (Foster City, CA). Chromatographic separation of test compounds and internal standard was achieved using a Hypersil Gold C18 column (50×2.1 mm, 5 µM, 175 Å) from ThermoFisher Scientific (Waltham, MA). Mobile phase A consisted of 0.1% formic acid in water, and mobile phase B consisted of 0.1% formic acid in acetonitrile. The total LC-MS/MS runtime was 2.75 minutes with a flow rate of 0.75 mL/min. Peak area integrations and peak area ratio calculations were performed using Analyst software (version 1.6.3) from Applied Biosystems.

The in vitro intrinsic clearance, $CL_{int,\ in\ vitro}$, was calculated from the $t_{1/2}$ of test compound disappearance as $CL_{int,\ in\ vitro}=(0.693/t_{1/2})\times(1/C_{protein})$, where $C_{protein}$ is the protein concentration during the incubation, and $t_{1/2}$ was determined by the slope (k) of the log-linear regression analysis of the concentration versus time profiles; thus, $t_{1/2}$=ln 2/k. The $CL_{int,\ in\ vitro}$ values were scaled to the in vivo values for human by using physiologically based scaling factors, hepatic microsomal protein concentrations (45 mg protein/g liver), and liver weights (21 g/kg body weight). The equation $CL_{int}=CL_{int,\ in\ vitro}\times$(mg protein/g liver weight)×(g liver weight/kg body weight) was used. The in vivo hepatic clearance ($CL_H$) was then calculated by using $CL_{int}$ and hepatic blood flow, Q (20 mL·min$^{-1}$·kg$^{-1}$ in humans) in the well-stirred liver model disregarding all binding from $CL_H=(Q\times CL_{int})/(Q+CL_{int})$. The hepatic extraction ratio was calculated as $CL_H$ divided by Q.

Example H. In Vivo Pharmacokinetics

Test compounds were administered to male Sprague Dawley rats or male and female Cynomolgus monkeys intravenously or via oral gavage. For intravenous (IV) dosing, test compounds were dosed at 1 mg/kg using a formulation of 10% dimethylacetamide (DMAC), 10% propylene glycol (PG) in acidified saline via IV bolus for rat or 10 min IV infusion for monkey. For oral (PO) dosing, test compounds were dosed at 3.0 mg/kg using 5% DMAC in 0.5% methylcellulose in citrate buffer (pH~2.5). Blood samples were collected at predose and various time points up to 24 hours postdose. All blood samples were collected using EDTA as the anticoagulant and centrifuged to obtain plasma samples. The plasma concentrations of test compounds were determined by LC-MS/MS methods. The measured plasma concentrations were used to calculate PK parameters by standard noncompartmental methods using Phoenix® WinNonlin software program (version 8.0, Pharsight Corporation) or similar software. In rats and monkeys, cassette dosing of test compounds were conducted to obtain preliminary PK parameters. In vivo pharmacokinetic experiments with male beagle dogs may be performed under the conditions described above.

The compounds of the disclosure and comparative examples were tested in one or more of the assays described in Examples E-H, and the resulting data are shown in Table B. The compounds of the current disclosure demonstrated improved intrinsic clearance and oral exposure in cynomolgus monkeys. Without being bound by theory, it is believed that Comparative Examples C-D would exhibit SET2 whole blood (WB) $IC_{50}$ values and Rat AUC values similar to the $IC_{50}$s measured for Comparative Examples A, B, and E, and that Comparative Examples C-E would exhibit Cyno AUC values similar to Comparative Examples A-B (see e.g., intrinsic clearance values).

TABLE B

| Example No. | SET2 IC$_{50}$ (nM) | SET2 WB IC$_{50}$ (nM) | h-IntCL (L/h/kg) | RAT PO AUC (nM * h) | CYNO PO AUC (nM * h) |
| --- | --- | --- | --- | --- | --- |
| Comparative Example A | ↓↓↓ | ↑↑↑↑ | ‡‡‡ | ††† (mouse) | † |
| Comparative Example B | ↓↓↓ | ↑↑↑↑ | ‡‡ | ††† | † |
| Comparative Example C | ↓ | NT | ‡‡‡ | NT | NT |
| Comparative Example D | ↓ | NT | ‡‡‡ | NT | NT |
| Comparative Example E | ↓↓ | ↑↑↑↑↑ | ‡‡‡ | ††† (mouse) | NT |
| 1 | ↓↓↓ | ↑↑ | ‡‡ | ††† | ††† |
| 2 | ↓↓ | ↑↑ | ‡‡ | ††† | ††† |
| 3 | ↓↓ | ↑↑↑ | ‡‡ | ††† | ††† |
| 4 | ↓↓ | ↑ | ‡ | ††† | ††† |
| 5 | ↓ | ↑ | ‡ | †† | ††† |
| 6 | ↓ | ↑ | ‡‡ | †† | ††† |
| 7 | ↓↓ | ↑↑ | ‡ | ††† | ††† |
| 8 | ↓ | ↑ | ‡ | ††† | † |
| 9 | ↓ | ↑↑ | ‡‡ | ††† | ††† |
| 10 | ↓ | ↑ | ‡‡ | ††† | †† |
| 11 | ↓ | ↑ | ‡‡ | NT | NT |
| 12 | ↓ | ↑ | ‡‡ | NT | NT |
| 13 | ↓ | ↑ | ‡‡ | †† | NT |
| 14 | ↓ | ↑ | ‡‡ | †† | NT |
| 15 | ↓ | ↑ | ‡‡ | †† | NT |
| 16 | ↓ | ↑ | ‡‡ | NT | NT |
| 17 | ↓ | ↑ | ‡‡ | NT | NT |
| 18 | ↓ | ↑ | ‡‡ | NT | NT |
| 19 | ↓ | ↑ | ‡‡ | NT | NT |
| 20 | ↓ | ↑ | ‡‡ | NT | NT |
| 21 | ↓ | ↑ | ‡‡ | NT | NT |

NT refers to "not tested"

↓ refers to IC$_{50}$ of ≤300 nM
↓↓ refers to IC$_{50}$ of >300 nM to ≤800 nM
↓↓↓ refers to IC$_{50}$ of >800 nM
↑ refers to IC$_{50}$ of ≤2500 nM
↑↑ refers to IC$_{50}$ of >2500 nM to ≤5000 nM
↑↑↑ refers to IC$_{50}$ of >5000 nM to ≤7500 nM
↑↑↑↑ refers to IC$_{50}$ of >7500 nM
‡ refers to h-IntCL of <0.7 L/h/kg
‡‡ refers to h-IntCL of ≥0.7 L/h/kg to ≤1 L/h/kg
‡‡‡ refers to h-IntCL of >1 L/h/kg
† refers to AUC of ≤500 nM * h
†† refers to AUC of >500 nM * h to ≤1500 nM * h
††† refers to AUC of >1500 nM * h

Example I. TRKA Enzymatic Assay

The kinase assays were carried out at 24° C. temperature in assay buffer (HEPES 50 mM, pH 7.0, NaN$_3$ 0.02%, BSA 0.01%, Orthovanadate 0.1 mM, DTT 1 mM, MgCl$_2$ 10 mM) in a final volume of 10 μL. Testing compounds were prepared by serial dilution in DMSO and transferred to the plate wells by ECHO liquid handler (Labcyte) with 0.5% DMSO in the final assay. The TRKA/TK Substrate-biotin mixture is prepared in the assay buffer with 1000 nM TK Substrate-biotin and SEB reagent 125 nM. 5 μL mixture was added to polystyrene 384-well small volume black plate (Greiner Bio-One). Reactions were initiated by the addition of 5 μL ATP in assay buffer. The final 10 μL kinase reaction consists of 0.58 nM TRKA, 1 mM ATP, 500 nM TK Substrate-biotin and SEB reagent 62.5 nM in assay buffer. Reactions were incubated for 90 min and terminated by addition of 10 μL of detection reagent containing 125 nM Streptavidin-XL665, TK Antibody-Cryptate in HTRF® Detection buffer (SEPES 50 mM, pH 7.0, BSA 0.1%, KF 0.8 M, EDTA 20 mM). After 60 minutes incubation at room temperature, the product activity was determined by measuring the fluorescence at 620 nm and 665 nm on Pherastar microplate reader (BMG Labtech). A ratio is calculated (665/620 nm) for each well. Wells with DMSO only were served as the positive controls and wells containing no ATP were used as negative controls. IC$_{50}$ determination was performed by fitting the curve of percent control activity versus the log of the compound concentration using the Gene data.

TABLE C

| Example No. | JH2 V617F Bind IC$_{50}$ (nM) | JH1 Bind IC$_{50}$ (nM) | TRKA IC$_{50}$ (nM) | Selectivity TRKA/ JH2 V617F |
| --- | --- | --- | --- | --- |
| Comparative Example A | + | +++++ | †††† | ** |
| Comparative Example B | + | +++++ | ††††† | ** |
| Comparative Example C | + | ++ | † | * |
| Comparative Example D | + | +++ | NT | NT |
| Comparative Example E | + | +++++ | ††† | ** |
| 1 | + | +++++ | †††† | ** |
| 2 | + | +++++ | ††††† | **** |
| 3 | + | +++++ | †††† | **** |
| 4 | + | +++++ | ††††† | ***** |
| 5 | + | +++++ | ††††† | ****** |
| 6 | + | +++++ | ††††† | ****** |
| 7 | + | +++++ | ††††† | ***** |
| 8 | + | +++++ | ††††† | ****** |
| 9 | + | +++++ | †††† | ***** |
| 10 | + | +++++ | ††††† | ****** |
| 11 | + | +++++ | ††††† | ****** |
| 12 | + | +++++ | ††††† | ****** |
| 13 | + | +++++ | ††††† | ****** |
| 14 | + | +++++ | ††††† | ****** |
| 15 | + | +++++ | †††† | ****** |
| 16 | + | +++++ | ††††† | ****** |
| 17 | + | +++++ | ††††† | ****** |
| 18 | + | +++++ | ††††† | ****** |
| 19 | + | +++++ | ††††† | ****** |
| 20 | + | +++++ | ††††† | ****** |
| 21 | + | +++++ | ††††† | ****** |

NT refers to "not tested"
+ refers to IC$_{50}$ of ≤10 nM
++ refers to IC$_{50}$ of >10 nM to ≤100 nM
+++ refers to IC$_{50}$ of >100 nM to ≤500 nM
++++ refers to IC$_{50}$ of >500 nM to ≤1000 nM
+++++ refers to IC$_{50}$ of >1000 nM
† refers to IC$_{50}$ of ≤25 nM
†† refers to IC$_{50}$ of >25 nM to ≤250 nM
††† refers to IC$_{50}$ of >250 nM to ≤1250 nM
†††† refers to IC$_{50}$ of >1250 nM to ≤2500 nM
††††† refers to IC$_{50}$ of >2500 nM
* refers to selectivity of ≤500-fold
** refers to selectivity of >500-fold to ≤1500-fold
*** refers to selectivity of >1500-fold to ≤1750-fold
**** refers to selectivity of >1750-fold to ≤5000-fold
***** refers to selectivity of >5000-fold to ≤12500-fold
****** refers to selectivity of >12500-fold Various modifications of the invention, in addition to those described herein, will be apparent to those skilled in the art from the foregoing description. Such modifications are also intended to fall within the scope of the appended claims. Each reference, including all patent, patent applications, and publications, cited in the present application is incorporated herein by reference in its entirety.

What is claimed is:

1. A compound, which is methyl ((1R,3R)-3-(7-(3-fluoro-1-(methyl-d₃)-1H-pyrazol-4-yl)-8-(4-fluorophenyl)-3-(methyl-d₃)-2-oxo-3,6-dihydroimidazo[4,5-d]pyrrolo[2,3-b]pyridin-1(2)-yl)cyclopentyl)carbamate, or a pharmaceutically acceptable salt thereof.

2. A compound, which is methyl ((1R,3R)-3-(8-(1,1-dimethyl-1,3-dihydroisobenzofuran-5-yl)-7-(3-fluoro-1-(methyl-d3)-1H-pyrazol-4-yl)-3-(methyl-d3)-2-oxo-3,6-dihydroimidazo[4,5-d]pyrrolo[2,3-b]pyridin-1(2H)-yl)cyclopentyl)carbamate, or a pharmaceutically acceptable salt thereof.

3. A pharmaceutical composition, comprising the compound of claim 1, or a pharmaceutically acceptable salt thereof, and a pharmaceutically acceptable carrier.

4. A pharmaceutical composition, comprising the compound of claim 2, or a pharmaceutically acceptable salt thereof, and a pharmaceutically acceptable carrier.

5. A compound, which is methyl ((1R,3R)-3-(8-(4-fluorophenyl)-7-(3-methoxy-1-methyl-1H-pyrazol-4-yl)-3-methyl-2-oxo-3,6-dihydroimidazo[4,5-d]pyrrolo[2,3-b]pyridin-1(2H)-yl)cyclopentyl)carbamate, or a pharmaceutically acceptable salt thereof.

6. A pharmaceutical composition, comprising the compound of claim 5, or a pharmaceutically acceptable salt thereof, and a pharmaceutically acceptable carrier.

7. The compound of claim 1, which is methyl ((1R,3R)-3-(7-(3-fluoro-1-(methyl-d₃)-1H-pyrazol-4-yl)-8-(4-fluorophenyl)-3-(methyl-d₃)-2-oxo-3,6-dihydroimidazo[4,5-d]pyrrolo[2,3-b]pyridin-1(2H)-yl)cyclopentyl)carbamate.

8. A pharmaceutical composition, comprising the compound of claim 7, and a pharmaceutically acceptable carrier.

9. The compound of claim 2, which is methyl ((1R,3R)-3-(8-(1,1-dimethyl-1,3-dihydroisobenzofuran-5-yl)-7-(3-fluoro-1-(methyl-d3)-1H-pyrazol-4-yl)-3-(methyl-d3)-2-oxo-3,6-dihydroimidazo[4,5-d]pyrrolo[2,3-b]pyridin-1(2H)-yl)cyclopentyl)carbamate.

10. A pharmaceutical composition, comprising the compound of claim 9, and a pharmaceutically acceptable carrier.

11. The compound of claim 5, which is methyl ((1R,3R)-3-(8-(4-fluorophenyl)-7-(3-methoxy-1-methyl-1H-pyrazol-4-yl)-3-methyl-2-oxo-3,6-dihydroimidazo[4,5-d]pyrrolo[2,3-b]pyridin-1(2H)-yl)cyclopentyl)carbamate.

12. A pharmaceutical composition, comprising the compound of claim 11, and a pharmaceutically acceptable carrier.

* * * * *